US008872001B2

(12) United States Patent
Broglie et al.

(10) Patent No.: US 8,872,001 B2
(45) Date of Patent: Oct. 28, 2014

(54) COMPOSITIONS AND METHODS FOR INSECTICIDAL CONTROL OF STINKBUGS

(75) Inventors: Karen E. Broglie, Landenberg, PA (US); David C. Cerf, Palo Alto, CA (US); Rafael Herrmann, Wilmington, DE (US); Albert L. Lu, Newark, DE (US); Brian McGonigle, Wilmington, DE (US); James K. Presnail, Avondale, PA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 351 days.

(21) Appl. No.: 13/152,795

(22) Filed: Jun. 3, 2011

(65) Prior Publication Data

US 2011/0301223 A1 Dec. 8, 2011

Related U.S. Application Data

(60) Provisional application No. 61/351,405, filed on Jun. 4, 2010.

(51) Int. Cl.

| | |
|---|---|
| ***C12N 15/113*** | (2010.01) |
| ***C12N 15/05*** | (2006.01) |
| ***C12N 15/14*** | (2006.01) |
| ***A01H 5/00*** | (2006.01) |
| ***A01N 57/16*** | (2006.01) |
| ***A01N 65/00*** | (2009.01) |
| ***C12N 15/82*** | (2006.01) |

(52) U.S. Cl.

CPC ............ *C12N 15/8286* (2013.01); *A01N 57/16* (2013.01); *A01N 65/00* (2013.01); *C12N 2310/531* (2013.01); *C12N 15/113* (2013.01); *C12N 2310/14* (2013.01); *C12N 15/8218* (2013.01)

USPC ....... 800/301; 536/24.5; 435/320.1; 435/419; 435/415; 800/298

(58) Field of Classification Search

None

See application file for complete search history.

(56) References Cited

U.S. PATENT DOCUMENTS

| | | | | |
|---|---|---|---|---|
| 7,560,542 | B2 * | 7/2009 | Andersen et al. | 536/23.6 |
| 7,745,391 | B2 * | 6/2010 | Mintz et al. | 514/19.3 |
| 8,067,671 | B2 * | 11/2011 | Boukharov et al. | 800/285 |
| 8,080,413 | B2 * | 12/2011 | Li | 435/320.1 |
| 8,143,476 | B2 * | 3/2012 | Meyer et al. | 800/278 |
| 2003/0150017 | A1 | 8/2003 | Mesa et al. | |
| 2005/0095199 | A1 | 5/2005 | Whyard et al. | |
| 2006/0021087 | A1 | 1/2006 | Baum et al. | |
| 2006/0075515 | A1 | 4/2006 | Luethy et al. | |
| 2006/0200878 | A1 | 9/2006 | Lutfiyya et al. | |
| 2006/0272049 | A1 | 11/2006 | Waterhouse et al. | |
| 2007/0199100 | A1 | 8/2007 | Michaeli et al. | |
| 2009/0188008 | A1 | 7/2009 | Lassner | |
| 2009/0192116 | A1 | 7/2009 | Herrmann et al. | |
| 2009/0192117 | A1 | 7/2009 | Herrmann et al. | |
| 2009/0265818 | A1 | 10/2009 | Herrmann et al. | |

FOREIGN PATENT DOCUMENTS

| | | | |
|---|---|---|---|
| EP | 1 818 405 | A3 | 8/2007 |
| WO | WO 01/34815 | A1 | 5/2001 |
| WO | WO 01/37654 | A2 | 5/2001 |
| WO | WO 02/00904 | A2 | 1/2002 |
| WO | WO 03/052110 | A2 | 6/2003 |
| WO | WO 2005/049841 | A1 | 6/2005 |
| WO | WO 2005/077116 | A2 | 8/2005 |
| WO | WO 2005/110068 | A2 | 11/2005 |
| WO | WO 2006/044480 | A2 | 4/2006 |
| WO | WO 2006/045590 | A2 | 5/2006 |
| WO | WO 2006/047495 | A2 | 5/2006 |
| WO | WO 2007/003023 | A2 | 1/2007 |
| WO | WO 2007/087153 | A2 | 8/2007 |
| WO | WO 2007/095469 | A2 | 8/2007 |

OTHER PUBLICATIONS

Thomas et al, 2001, Plant J., 25:417-425.*

Jagadeeswaran, G., et al., "Deep sequencing of small RNA libraries reveals dynamic regulation of conserved and novel microRNA-stars during silkworm development," *BMC Genomics*, 2010, vol. 11(52), pp. 1-18.

Sindhu, A., et al., "Effective and specific *in planta* RNAi in cyst nematodes: expression interference of four parasitism genes reduces parasitic success," *Journal of Experimental Botany*, 2009, vol. 60(1), pp. 315-324.

Tomoyasu, Y., et al., "Exploring systemic RNA interference in insects: a genome-wide survey for RNAi genes in *Tribolium*," *Genome Biology*, 2008, vol. 9(1), pp. R10-R10.22.

(Continued)

*Primary Examiner* — David H Kruse

*Assistant Examiner* — Jason Deveau Rosen

(74) *Attorney, Agent, or Firm* — Pioneer Hi-Bred Int'l, Inc.

(57) ABSTRACT

Methods and compositions are provided which employ a silencing element that, when ingested by a pest, such as a Pentatomidae plant pest or a *N. viridula, Acrosternum hilare, Piezodorus guildini*, and/or *Halymorpha halys* plant pest, decrease the expression of a target sequence in the pest. In specific embodiments, the decrease in expression of the target sequence controls the pest and thereby the methods and compositions are capable of limiting damage to a plant. The present invention provides various target polynucleotides set forth in any one of SEQ ID NOS: 1-292 or 302-304 or active variants and fragments thereof, wherein a decrease in expression of one or more the sequences in the target pest controls the pest (i.e., has insecticidal activity). Further provided are silencing elements which when ingested by the pest decrease the level of the target polypeptide and thereby control the pest. In specific embodiment, the pest is Pentatomidae. Plants, plant part, bacteria and other host cells comprising the silencing elements or an active variant or fragment thereof of the invention are also provided.

36 Claims, 2 Drawing Sheets

(56) References Cited

OTHER PUBLICATIONS

Zhang, Y., et al., "Insect-Specific microRNA Involved in the Development of the Silkworm Bombyx mori," *PLoS ONE*, 2009, vol. 4(3), e4677, pp. 1-7.

Agrawal, N., et al., "siRNA-Directed Silencing of Transgene Expressed in Cultured Insect Cells", Biochemical and Biophysical Research Communications, 2004, pp. 428-434, vol. 320, No. 2, Elsevier Science Publishers Ltd., United Kingdom.

Atkinson, H. J., et al., "Engineering Plants for Nematode Resistance," Ann. Rev. Phytopathol, 2003, pp. 615-639, vol. 41.

Boutla, A., et al., "Induction of RNA Interference in Caenorhabditis Elegans by RNAs Derived From Plants Exhibiting Post-Transcriptional Gene Silencing", Nucleic Acids Research, 2002, pp. 1688-1694, vol. 30, No. 7.

* cited by examiner

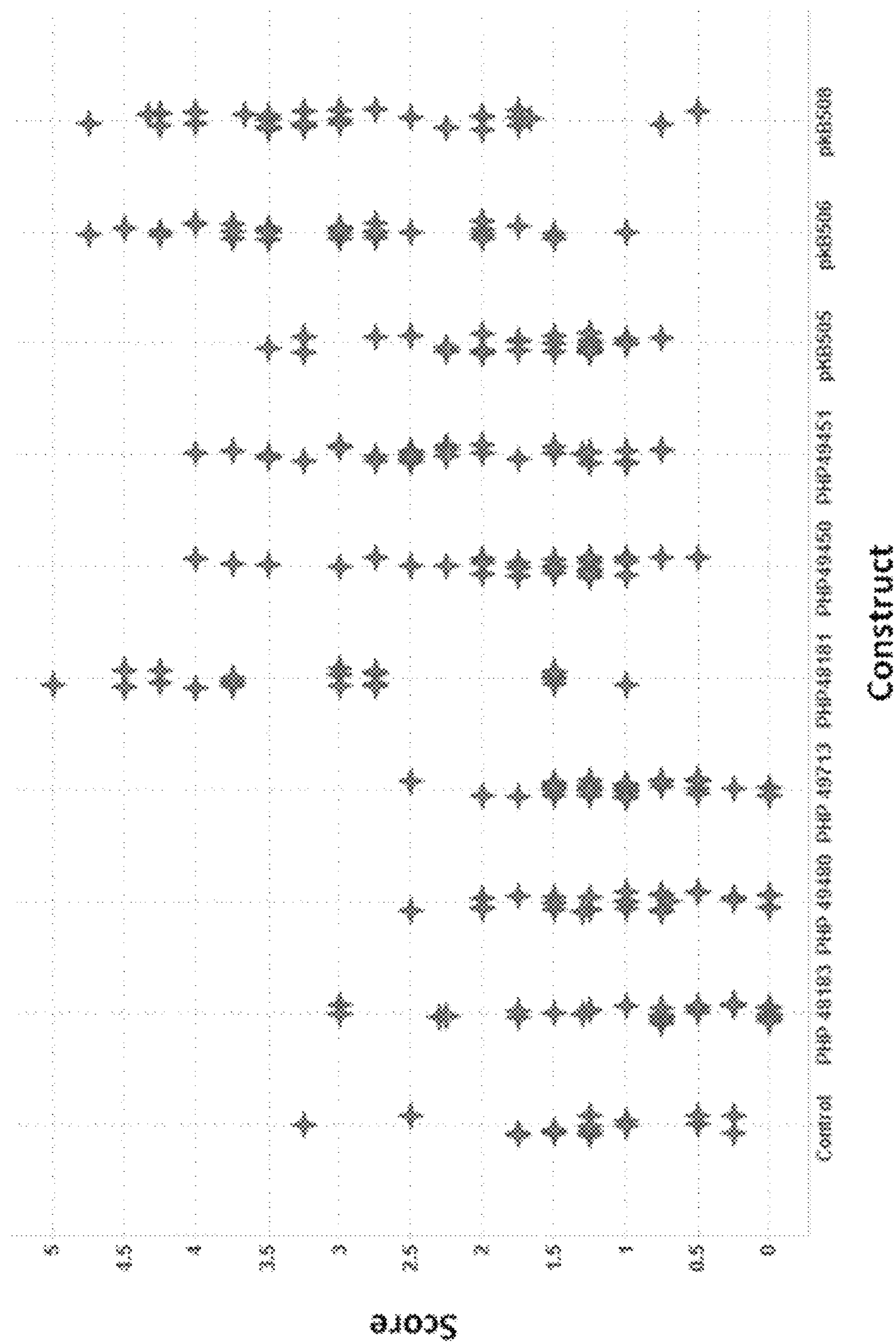
Figure 1. 2nd instar SGSB feeding assays on soybean embryo tissue containing HP constructs
Score
5
4.5
4
3.5
3
2.5
2
1.5
1
0.5
0
Construct
Control Figure 2. 2nd instar SGSB feeding assays on soybean embryo tissue containing amiRNA constructs
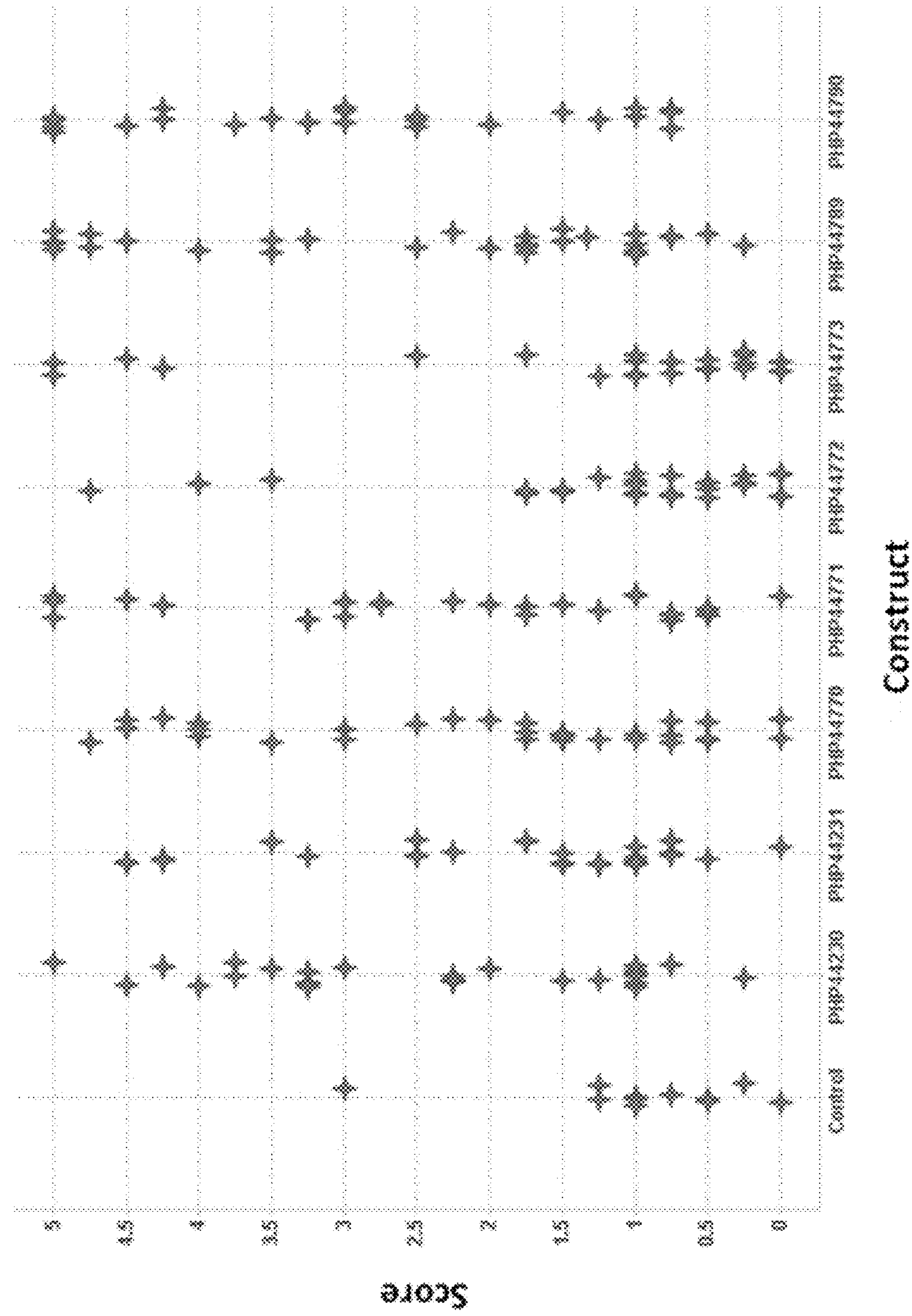

COMPOSITIONS AND METHODS FOR INSECTICIDAL CONTROL OF STINKBUGS

CROSS-REFERENCE TO RELATED APPLICATION

This application claims the benefit of U.S. Provisional Application Ser. No. 61/351,405, filed Jun. 4, 2010, which is herein incorporated by reference.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 402360SEQLIST.txt, a creation date of Jun. 2, 2011 and a size of 195 KB. The sequence listing filed via EFS-Web is part of the specification and is hereby incorporated in its entirety by reference herein.

FIELD OF THE INVENTION

The present invention relates generally to methods of molecular biology and gene silencing to control pests.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including *Lepidoptera, Diptera, Coleoptera, Hemiptera*, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life. Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences.

Previous control of stinkbugs relied on broad spectrum insecticides. With the adoption of transgenic controls for major lepidopteran pests in several crops, these insecticides are no longer used and stinkbugs have become a major secondary pest. No successful use of transgenic control of stinkbugs has been described or adopted. This may be due in part to the extra oral digestion employed by stinkbugs where digestive enzymes are injected into the host plant prior to feeding. This makes it difficult to find proteins that survive long enough to manifest activity against these insects. RNAi may overcome that feeding behavior by relying on double stranded RNAs rather than proteins. Thus, there is an immediate need for alternative methods to control pests.

BRIEF SUMMARY OF THE INVENTION

Methods and compositions are provided which employ a silencing element that, when ingested by a pest, such as a Pentatomidae plant pest including for example, a *N. viridula* (southern green stink bug), *Acrosternum hilare* (green stinkbug), *Piezodorus guildini* (redbanded stinkbug), and/or *Halymorpha halys* (Brown marmorated stinkbug). plant pest, is capable of decreasing the expression of a target sequence in the pest. In specific embodiments, the decrease in expression of the target sequence controls the pest and thereby the methods and compositions are capable of limiting damage to a plant. The present invention provides various target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303 or 304 or active variants or fragments thereof, wherein a decrease in expression of one or more the sequences in the target pest controls the pest (i.e., has insecticidal activity). Further provided are silencing elements, which when ingested by the pest, decrease the level of expression of one or more of the target polynucleotides. Plants, plant parts, plant cells, bacteria and other host cells comprising the silencing elements or an active variant or fragment thereof are also provided.

In another embodiment, a method for controlling a pest, such as a Pentatomidae plant pest, such as, for example, a *N. viridula, Acrosternum hilare, Piezodorus guildini*, and/or *Halymorpha halys* plant pest, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part a silencing element of the invention. When the plant expressing the silencing element is ingested by the pest, the level of the target sequence is decreased and the pest is controlled.

BRIEF DESCRIPTION OF THE DRAWINGS

FIG. 1 shows the Southern Green Stinkbug feeding assay results with soybean embryo tissue transformed with hairpin RNA silencing contructs.

FIG. 2 shows the Southern Green Stinkbug feeding assay results with soybean embryo tissue transformed with amiRNA silencing constructs.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Frequently, RNAi discovery methods rely on evaluation of known classes of sensitive genes (transcription factors, housekeeping genes etc.). In contrast, the target polynucleotide set forth herein were identified based solely on high throughput screens of a library of over 1000 expressed sequence tags from *N. viridula*. This screen allowed for the discovery of many novel sequences, many of which have extremely low or no homology to known sequences. This method provided the advantage of having no built in bias to genes that are frequently highly conserved across taxa. As a result, many novel targets for RNAi as well as known genes not previously shown to be sensitive to RNAi have been identified.

As such, methods and compositions are provided which employ a silencing element that, when ingested by a pest, such as a Pentatomidae plant pest or, for example, a *N. viridula, Acrosternum hilare, Piezodorus guildini*, and/or *Halymorpha halys* plant pest, is capable of decreasing the expression of a target sequence in the pest. In specific embodiments, the decrease in expression of the target sequence controls the pest and thereby the methods and compositions are capable of limiting damage to a plant or plant part. The present invention provides target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303, or 304. or active variants and fragments thereof. Silencing elements designed in view of these target polynucleotides are provided which, when ingested by the pest, decrease the expression of one or more of the target sequences and thereby controls the pest (i.e., has insecticidal activity).

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to control pests, particularly, Pentatomidae plant pest or a *N. viridula, Acrosternum hilare, Piezodorus guildini*, and/or *Halymorpha halys* plant pest.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also Baum et al. (2007) *Nature Biotech* 11:1322-1326 and WO 2007/035650 which proved both whole plant feeding assays and corn root feeding assays. Both of these references are herein incorporated by reference in their entirety. See, also the examples below.

The invention is drawn to compositions and methods for protecting plants from a plant pest, such as Pentatomidae plant pests or *N. viridula, Acrosternum hilare, Piezodorus guildini*, and/or *Halymorpha halys* plant pests or inducing resistance in a plant to a plant pest, such as Pentatomidae plant pests or *N. viridula, Acrosternum hilare, Piezodorus guildini*, and/or *Halymorpha halys* plant pests. As used herein "Pentatomidae plant pest" is used to refer to any member of the Pentatomidae family. Accordingly, the compositions and methods are also useful in protecting plants against any Pentatomidae plant pest including representative genera and species such as, but not limited to, *Acrocorisellus* (*A. serraticollis*), *Acrosternum* (*A. adelpha, A. hilare, A. herbidum, A. scutellatum*), *Agonoscelis* (*A. nubila*), *Alcaeorrhynchus* (*A. grandis, A. phymatophorus*), *Amaurochrous* (*A. brevitylus*), *Apateticus* (*A. anatarius, A. bracteatus, A. cynicus, A. lineolatus, A. marginiventris*), *Apoecilus, Arma* (*A. custos*), *Arvelius, Bagrada, Banasa* (*B. calva, B. dimiata, B. grisea, B. induta, B. sordida*), *Brochymena* (*B. affinis, B. cariosa, B. haedula, B. hoppingi, B. sulcata*), *Carbula* (*C. obtusangula, C. sinica*), *Chinavia, Chlorochroa* (*C. belfragii, C. kanei, C. norlandi, C. senilis, C. viridicata*), *Chlorocoris* (*C. distinctus,*

*C. flaviviridis, C. hebetatus, C. subrugosus, C. tau*), *Codophila* (*C. remota, C. sulcata, C. varius*), *Coenus* (*C. delius, C. inermis, C. tarsalis*), *Cosmopepla* (*C. bimaculata, C. binotata, C. carnifex, C. decorata, C. intergressus*), *Dalpada* (*D. oculata*), *Dendrocoris* (*D. arizonesis, D. fruticicola, D. humeralis, D. parapini, D. reticulatus*), *Dolycoris* (*D. baccarum* (sloe bug)), *Dybowskyia* (*D. reticulata*), *Edessa, Erthesina* (*E. fullo*), *Eurydema* (*E. dominulus, E. gebleri* (shield bug), *E. pulchra, E. rugosa*), *Euschistus* (*E. biformis, E. integer, E. quadrator, E. servus, E. tristigma*), *Euthyrhynchus* (*E. floridanus, E. macronemis*), *Gonopsis* (*G. coccinea*), *Graphosoma* (*G. lineatum* (stink bug), *G. rubrolineatum*), *Halyomorpha* (*H. halys* (brown marmorated stink bug)), *Halys* (*H. sindillus, H. sulcatus*), *Holcostethus* (*H. abbreviatus, H. fulvipes, H. limbolarius, H. piceus, H. sphacelatus*), *Homalogonia* (*H. obtusa*), *Hymenarcys* (*H. aequalis, H. crassa, H. nervosa, H. perpuncata, H. reticulata*), *Lelia* (*L. decempunctata*), *Lineostethus, Loxa* (*L. flavicollis, L. viridis*), *Mecidea* (*M. indicia, M. major, M. minor*), *Megarrhamphus* (*M. hastatus*), *Menecles* (*M. insertus, M. portacrus*), *Mormidea* (*M. cubrosa, M. lugens, M. pama, M. pictiventris, M. ypsilon*), *Moromorpha* (*M. tetra*), *Murgantia* (*M. angularis, M. tessellata, M. varicolor, M. violascens*), *Neottiglossa* (*N. californica, N. cavifrons, N. coronaciliata, N. sulcifrons, N. undata*), *Nezara* (*N. smaragdulus, N. viridula* (southern green stink bug)), *Oebalus* (*O. grisescens, O. insularis, O. mexicanus, O. pugnax, O. typhoeus*), *Oechalia* (*O. schellenbergii* (spined predatory shield bug)), *Okeanos* (*O. quelpartensis*), *Oplomus* (*O. catena, O. dichrous, O. tripustulatus*), *Palomena* (*P. prasina* (green shield bug)), *Parabrochymena, Pentatoma* (*P. angulata, P. illuminata, P. japonica, P. kunmingensis, P. metallifera, P. parataibaiensis, P. rufipes, P. semiannulata, P. viridicornuta*), *Perillus* (*P. bioculatus, P. confluens, P. strigipes*), *Picromerus* (*P. griseus*), *Piezodorus* (*P. degeeri, P. guildinii, P. lituratus* (gorse shield bug)), *Pinthaeus* (*P. humeralis*), *Plautia* (*P. crossota, P. stali* (brown-winged green bug)), *Podisus* (*P. maculiventris*), *Priassus* (*P. testaceus*), *Prionosoma, Proxys* (*P. albopunctulatus, P. punctulatus, P. victor*), *Rhaphigaster* (*R. nebulosa*), *Scotinophara* (*S. horvathi*), *Stiretrus* (*S. anchorago, S. fimbriatus*), *Thyanta* (*T. accerra, T. calceata, T. casta, T. perditor, T. pseudocasta*), *Trichopepla* (*T. aurora, T. dubia, T. pilipes, T. semivittata, T. vandykei*), *Tylospilus*, and *Zicrona*.

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance, the target sequence can be essential for growth and development. While the target sequence can be expressed in any tissue of the pest, in specific embodiments, the sequences targeted for suppression in the pest are expressed in cells of the gut tissue of the pest, cells in the midgut of the pest, and cells lining the gut lumen or the midgut. Such target sequences can be involved in, for example, gut cell metabolism, growth or differentiation. Non-limiting examples of target sequences of the invention include a polynucleotide set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303, or 304. As exemplified elsewhere herein, decreasing the level of expression of one or more of these target sequences in a Pentatomidae plant pest or a *N. viridula, Acrosternum hilare, Piezodorus guildini*, and/or *Halymorpha halys* plant pest controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprise one or more silencing elements to the same or different target polynucleotides. The silencing element can be produced in vivo (i.e., in a host cell such as a plant or microorganism) or in vitro.

In specific embodiments, the target sequence is not endogenous to the plant. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a siRNA, an amiRNA, a miRNA, or a hairpin suppression element. Non-limiting examples of silencing elements that can be employed to decrease expression of these target Pentatomidae plant pest sequences or *N. viridula, Acrosternum hilare, Piezodorus guildini*, and/or *Halymorpha halys* plant pest sequences comprise fragments and variants of the sense or antisense sequence or consists of the sense or antisense sequence of the sequence set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303, or 304 or a biologically active variant or fragment thereof. Additional sequences that can be employed as silencing elements include, for example, SEQ ID NOS: 284, 285, 286, 287, 288, 289, 290, 291, 292, 293, 294, 295, 296, 297, 298, 299, 300, 301, 305, 306, 307, 308, 309, 310, 311, 312, 321, 322, 323, 324, 325, 326, 327, 328, 329, 330, 331, 332, 333, 334, 335, or 336 or active variants or fragments thereof. The silencing element can further comprise additional sequences that advantageously effect transcription and/or the stability of a resulting transcript. For example, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end. As discussed in further detail below, enhancer suppressor elements can also be employed in conjunction with the silencing elements disclosed herein.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 16, 17, 18 19, 20, 22, 25, 30, 50, 100, 150, 200, 250, 300, 350, 400, 450, 500, 600, 700, 900, 1000, 1100, 1200, 1300 nucleotides or longer of the target polynucleotides set forth in any of SEQ ID NO:1-292 or 302-304. In other embodiments, the sense suppression element can be, for example, about 15-25, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides set forth in any of SEQ ID NO: 1-292 or 302-304.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 20, 22, 25, 50, 100, 200, 300, 400, 450 nucleotides or greater of the sequence set forth in any of SEQ ID NO: 1-292 or 302-304 may be used. Methods for using antisense suppression to inhibit the expression of endogenous genes in plants are described, for example, in Liu et at (2002) *Plant Physiol.* 129:1732-1743 and U.S. Pat. Nos. 5,759,829 and 5,942,657, each of which is herein incorporated by reference.

iii. Double Stranded RNA Suppression Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672;

Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional dsRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In another embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 400, 300, 200, 100, 50, 40, 30, 25, 22, 20, 19, 18, 17, 16, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides, about 600 nt, about 700 nt, about 800 nt, about 900 nt, about 1000 nt, about 1100 nt, about 1200 nt, 1300 nt, 1400 nt, 1500 nt, 1600 nt, 1700 nt, 1800 nt, 1900 nt, 2000 nt or longer. In other embodiments, the length of the first and/or the third segment comprises at least 10-19 nucleotides; 19-35 nucleotides; 30-45 nucleotides; 40-50 nucleotides; 50-100 nucleotides; 100-300 nucleotides; about 500-700 nucleotides; about 700-900 nucleotides; about 900-1100 nucleotides; about 1300-1500 nucleotides; about 1500-1700 nucleotides; about 1700-1900 nucleotides; about 1900-2100 nucleotides; about 2100-2300 nucleotides; or about 2300-2500 nucleotides. See, for example, International Publication No. WO 0200904. In specific embodiments, the first and the third segment comprise at least 19 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 19-35 nucleotides, about 25-50 nucleotides, about 19 to 75 nucleotides, about 40-90 nucleotides about 15-100 nucleotides 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides or longer. In other embodiments, the length of the first and/or the third segment comprises at least 10-19 nucleotides, 19-35 nucleotides, 30-45 nucleotides, 40-50 nucleotides, 50-100 nucleotides, or about 100-300 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129: 1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments, a domain of the silencing element shares sufficient homology to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem.* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J* 19(19):5194-5201.

While the various target sequences disclosed herein can be used to design any silencing element that encodes a hairpin suppression construct, non-limiting examples of such hairpin constructs are set forth in SEQ ID NO: 293 which targets SEQ ID NO: 278; SEQ ID NOS: 294, 295 and 296 which target SEQ ID NO: 279; SEQ ID NOS: 297 and 298 which target SEQ ID NO:280; SEQ ID NO:299 which targets SEQ ID NO:281; SEQ ID NO: 300 which targets SEQ ID NO: 282; and SEQ ID NO: 301 which targets SEQ ID NO: 283; or active variants or fragments thereof.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). "MicroRNAs" or "miRNAs" are regulatory agents comprising about 19 to about 24 nucleotides (nt) in length, which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 21 nucleotide sequence that is complementary to the target polynucleotide of interest. The miRNA can be an "artificial miRNA" or "amiRNA" which comprises a miRNA sequence that is synthetically designed to silence a target sequence.

When expressing an miRNA, the final (mature) miRNA is present in a duplex in a precursor backbone structure, the two strands being referred to as the miRNA (the strand that will eventually basepair with the target) and miRNA* (star sequence). This final miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18:2237-2242 and Guo et al. (2005) *Plant Cell* 17:1376-1386).

The silencing element for miRNA interference comprises a miRNA precursor backbone. The miRNA precursor backbone comprises a DNA sequence having the miRNA and star sequences. When expressed as an RNA, the structure of the miRNA precursor backbone is such as to allow for the formation of a hairpin RNA structure that can be processed into a miRNA. In some embodiments, the miRNA precursor backbone comprises a genomic miRNA precursor sequence, wherein said sequence comprises a native precursor in which an heterologous (artificial) miRNA and star sequence are inserted.

As used herein, a "star sequence" is the sequence within a miRNA precursor backbone that is complementary to the miRNA and forms a duplex with the miRNA to form the stem structure of a hairpin RNA. In some embodiments, the star sequence can comprise less than 100% complementarity to the miRNA sequence. Alternatively, the star sequence can comprise at least 99%, 98%, 97%, 96%, 95%, 90%, 85%, 80% or lower sequence complementarity to the miRNA sequence as long as the star sequence has sufficient complementarity to the miRNA sequence to form a double stranded structure. In still further embodiments, the star sequence comprises a sequence having 1, 2, 3, 4, 5 or more mismatches with the miRNA sequence and still has sufficient complementarity to form a double stranded structure with the miRNA sequence resulting in production of miRNA and suppression of the target sequence.

The miRNA precursor backbones can be from any plant. In some embodiments, the miRNA precursor backbone is from a monocot. In other embodiments, the miRNA precursor backbone is from a dicot. In further embodiments, the backbone is from maize or soybean. MicroRNA precursor backbones have been described previously. For example, US20090155910A1 (WO 2009/079532) discloses the following soybean miRNA precursor backbones: 156c, 159, 166b, 168c, 396b and 398b, and US20090155909A1 (WO 2009/079548) discloses the following maize miRNA precursor backbones: 159c, 164h, 168a, 169r, and 396h. Each of these references is incorporated by reference in their entirety.

Thus, the miRNA precursor backbone can be altered to allow for efficient insertion of heterologous miRNA and star sequences within the miRNA precursor backbone. In such instances, the miRNA segment and the star segment of the miRNA precursor backbone are replaced with the heterologous miRNA and the heterologous star sequences, designed to target any sequence of interest, using a PCR technique and cloned into an expression construct. It is recognized that there could be alterations to the position at which the artificial miRNA and star sequences are inserted into the backbone. Detailed methods for inserting the miRNA and star sequence into the miRNA precursor backbone are described elsewhere herein (see, Example 8) and are also described in, for example, US Patent Applications 20090155909A1 and US20090155910A1, herein incorporated by reference in their entirety.

When designing a miRNA sequence and star sequence, various design choices can be made. See, for example, Schwab R, et al. (2005) *Dev Cell* 8: 517-27. In non-limiting embodiments, the miRNA sequences disclosed herein can have a "U" at the 5'-end, a "C" or "G" at the $19^{th}$ nucleotide position, and an "A" or "U" at the 10th nucleotide position. In other embodiments, the miRNA design is such that the miRNA have a high free delta-G as calculated using the ZipFold algorithm (Markham, N. R. & Zuker, M. (2005) *Nucleic Acids Res.* 33: W577-W581.) Optionally, a one base pair change can be added within the 5' portion of the miRNA so that the sequence differs from the target sequence by one nucleotide.

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, US Application Publication 2007-0130653, entitled "Methods and Compositions for Gene Silencing", herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

While the various target sequences disclosed herein can be used to design any silencing element that encodes a miRNA, non-limiting examples of such miRNA constructs include SEQ ID NOS: 311, 312, 327, 328, 335 or 336 which target SEQ ID NO: 304; SEQ ID NOS: 307, 308, 323, 324, 331 or 332 which target SEQ ID NO: 278; SEQ ID NOS: 309, 310, 325, 326, 333 or 334 which target SEQ ID NO: 303; and SEQ ID NOS: 305, 306, 321, 322, 329 or 330 which target SEQ ID NO: 302; or active variants or fragments thereof.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 16, about 17, about 18, about 19, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide employed in the invention. Alternatively, fragments of a nucleotide sequence may range from 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NOS: 1-304 or 321-336. Methods to assay for the activity of a desired silencing element are described elsewhere herein.

Encompassed herein are fragments of the various target sequences (i.e. SEQ ID NOS: 1-292 and 302-304) which are useful as silencing elements and fragments of the various silencing elements provided herein (i.e. SEQ ID NOS:293-301 or 321-336). Thus, fragments of a nucleotide sequence that are useful as silencing elements may range from at least about 10, about 15, about 16, about 17, about 18, about 19, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide sequences of SEQ ID NOS: 1-304 or 321-336. Alternatively, fragments of a nucleotide sequence that are useful as silencing elements may range from 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NOS: 1-304 or 321-336. Methods to assay for the activity of a desired silencing element are described elsewhere herein. Various, non-limiting examples of fragments of SEQ ID NOS: 1-292 or 302-304 are provided herein and include, for example, SEQ ID NOS: 284-292 or 305-312.

"Variants" is intended to mean substantially similar sequences. Thus, further provided are variants of the various sequences set forth in SEQ ID NOS: 1-336. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as a silencing element will retain the ability to reduce expression of the target polynucleotide and, in some embodiments, thereby control a pest of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A method is further provided for identifying a silencing element from the target polynucleotides set froth in SEQ ID NO: 1-292 or 302-304. Such methods comprise obtaining a candidate fragment of any one of SEQ ID NO: 1-292 or 302-304 which is of sufficient length to act as a silencing element and thereby reduce the expression of the target polynucleotide and/or control a desired pest; expressing said candidate polynucleotide fragment in an appropriate expression cassette to produce a candidate silencing element and determining is said candidate polynucleotide fragment has the activity of a silencing element and thereby reduce the expression of the target polynucleotide and/or controls a desired pest. Methods of identifying such candidate fragments based on the desired pathway for suppression are known. For example, various bioinformatics programs can be employed to identify the region of the target polynucleotides that could be exploited to generate a silencing element. See, for example, Elbahir et al. (2001) *Genes and Development* 15:188-200, Schwartz et al. (2003) *Cell* 115:199-208, Khvorova et al. (2003) *Cell* 115:209-216. See also, siRNA at Whitehead (jura.wi.mit.edu/bioc/siRNAext/) which calculates the binding energies for both sense and antisense siRNAs. See, also genscript.com/ss1-bin/app/rnai?op=known; Block-iT™ RNAi designer from Invitrogen and GenScript siRNA Construct Builder.

V. DNA Constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element or in specific embodiments employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. In other embodiment, the double stranded RNA is expressed from a suppression cassette. Such a cassette can comprise two convergent promoters that drive transcription of an operably linked silencing element. "Convergent promoters" refers to promoters that are oriented on either terminus of the operably linked silencing element such that each promoter drives transcription of the silencing element in opposite directions, yielding two transcripts. In such embodiments, the convergent promoters allow for the transcription of the sense and anti-sense strand and thus allow for the formation of a dsRNA.

The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026); soybean elongation factor 1A (ACUP01009998), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

In one embodiment, the various silencing elements disclosed herein are expressed using a seed-preferred promoter. "Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); Kunitz trypsin inhibitor 3 (kti3) (Genbank accession AF233296); glycinin-1 genes (Genbank accession AB353075.1); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-preferred promoters include, but are not limited to, bean β-phaseolin, napin, β-conglycinin alpha (Genbank accession GU723691), soybean lectin, cruciferin, and the like. For monocots, seed-preferred promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol.*

*Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes* (Kiyokawa et al. (1994) *Plant Physiology* 104:801-02; Pandolfini et al. (2003) *BioMedCentral* (BMC) *Biotechnology* 3:7, (biomedcentral.com/1472-6750/3/7); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or *Commelina* yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultrl; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Chemy promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11):1779-86), Rice (RSs1) (Shi, T. Wang et al. (1994). *J. Exp. Bot.* 45(274): 623-631) and maize sucrose synthese-1 promoters (Yang, N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196(3):564-70, At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element can be provided as an external composition such as a spray or powder to the plant, plant part, seed, a pest, or an area of cultivation. In another example, a plant is transformed with a DNA construct or expression cassette for expression of at least one silencing element. In either composition, the silencing element, when ingested by an insect, can reduce the level of a target pest sequence and thereby control the pest (i.e., a Pentatomidae plant pest including a *N. viridula, Acrosternum hilare, Piezodorus guildini*, and/or *Halymorpha halys*. It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory*

*Manual* (3rd ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutant before application.

The compositions (including the transformed microorganisms) can be applied to the environment of an insect pest (such as a Pentatomidae plant pest or a *N. viridula, Acrosternum hilare, Piezodorus guildini*, and/or *Halymorpha halys* plant pest) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

The methods of the invention involve introducing a polynucleotide into a plant. In one embodiment, a plant cell is provided having stably incorporated into its genome a heterologous polynucleotide comprising any of the various silencing elements provided herein. It is recognized that the silencing element, when ingested by a Pentatomidae plant pest, can reduce the level of expression of any of the target sequences described herein (i.e. SEQ ID NOS: 1-292 or 302-304). "Introducing" is intended to mean presenting to the plant the polynucleotide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, U.S. Pat. No. 5,932,782; Tomes et al. (1995) in *Plant Cell, Tissue, and Organ Culture: Fundamental* Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the silencing element sequences of the invention can be provided to a plant using a variety of transient transformation methods. Such transient transformation methods include, but are not limited to, the introduction of the protein or variants and fragments thereof directly into the plant or the introduction of the transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), *macadamia* (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In specific embodiments, the plants/plant cells and/or seeds comprising an expression construct comprise a silencing element directed to a target sequence provided herein (i.e. SEQ ID NOS: 1-292 or 302-304) operably linked to a seed-preferred promoter.

VIII. Methods of Use

The methods of the invention comprise methods for controlling a pest (i.e., a Pentatomidae plant pest, such as, *N. viridula, Acrosternum hilare, Piezodorus guildini*, and/or *Halymorpha halys* plant pest). The method comprises feeding to a pest a composition comprising a silencing element of the invention, wherein said silencing element, when ingested by a pest (i.e., a Pentatomidae plant pest including *N. viridula, Acrosternum hilare, Piezodorus guildini*, and/or *Halymorpha halys*), reduces the level of a target polynucleotide of the pest and thereby controls the pest. The pest can be fed the silencing element in a variety of ways. For example, in one embodiment, the polynucleotide comprising the silencing element is introduced into a plant. As the Pentatomidae plant pest or *N. viridula, Acrosternum hilare, Piezodorus guildini*, and/or *Halymorpha halys* plant pest feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In one embodiment, the silencing element is operably linked to a seed-preferred promoter. In specific embodiments, the silencing element expressed in the roots, stalk or stem, leaf including pedicel, xylem and phloem, fruit or reproductive tissue, silk, flowers and all parts therein or any combination thereof.

In another method, a composition comprising at least one silencing element of the invention is applied to a plant. In such embodiments, the silencing element can be formulated in an agronomically suitable and/or environmentally acceptable carrier, which is preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. application Ser. No. 12/351,093, entitled "Compositions and Methods for the Suppression of Target Polynucleotides", filed Jan. 9, 2009 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a polynucleotide set forth in SEQ ID NO: 1-292, or 302-304 or an active variant or fragment thereof.

It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the invention have an improved loading of RNAi into the phloem of the plant than would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

Non-limiting examples of methods and compositions are disclosed herein. An example of methods and compositions comprise an isolated polynucleotide comprising a nucleotide sequence selected from the group consisting of: (a) the nucleotide sequence comprising any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof; (b) the nucleotide sequence comprising at least 90% sequence identity to any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof, wherein said polynucleotide encodes a silencing element having insecticidal activity against a Pentatomidae plant pest; (c) the nucleotide sequence comprising at least 19 consecutive nucleotides of any one of SEQ ID NOS: 279, 302, 281, 304, 280, 283, 282, 303, 278, 284, 285, 286, 287, 288, 289, 290, 291, 292, 17, 30, 34, 14, 18 or 263 or a complement thereof, wherein said polynucleotide encodes a silencing element having insecticidal activity against a Pentatomidae plant pest; and, (d) the nucleotide sequence that hybridizes under stringent conditions to the full length complement of the nucleotide sequence of a), wherein said stringent conditions comprise hybridization in 50% formamide, 1 M NaCl, 1% SDS at 37° C., and a wash in 0.1×SSC at 60° C. to 65° C., wherein said polynucleotide encodes a silencing element having insecticidal activity against a Pentatomidae plant pest. A Pentatomidae plant pest may be a *N. viridula* plant pest.

An example of methods and compositions comprise an expression cassette comprising a heterologous polynucleotide disclosed herein operably linked to a seed-preferred promoter. An expression cassette may express a polynucleotide disclosed herein as a double stranded RNA. An expression cassette comprising a heterologous polynucleotide disclosed herein, wherein said polynucleotide comprises a silencing element which is expressed as a hairpin RNA. An expression cassette may comprise a silencing element that comprises, in the following order, a first segment, a second segment, and a third segment, wherein a) said first segment comprises at least about 19 nucleotides having at least 90% sequence complementarity to a target sequence set forth in SEQ ID NOS: 279, 302, 281, 304, 280, 283, 282, 303, 278, 284, 285, 286, 287, 288, 289, 290, 291, 292, 17, 30, 34, 14, 18 or 263; b) said second segment comprises a loop of sufficient length to allow the silencing element to be transcribed as a hairpin RNA; and, c) said third segment comprises at least about 19 nucleotides having at least 85% complementarity to the first segment. A target sequence for an expression cassette may comprises the sequences set forth any one of SEQ ID NOS: 284, 285, 286, 287, 288, 289, 290, 291, 292, 337, 338, 339, 340, 341, 342, 343 or 344 or a sequence having at least 90% sequence identity to SEQ ID NOS: 284, 285, 286, 287, 288, 289, 290, 291, 292, 337, 338, 339, 340, 341, 342, 343 or 344. An expression cassette may comprise any one of SEQ ID NOS: 293, 294, 295, 296, 297, 298, 299, 300, 301, 321, 322, 323, 324, 325, 326, 327 or 328.

An expression cassette, wherein said may comprise a polynucleotide that is flanked by a first operably linked convergent promoter at one terminus of the polynucleotide and a second operably linked convergent promoter at the opposing terminus of the polynucleotide, wherein the first and the second convergent promoters are capable of driving expression of the polynucleotide.

An example of methods and compositions comprises a host cell comprising a heterologous expression cassette disclosed herein.

An example of methods and compositions comprises a plant cell having stably incorporated into its genome a heterologous polynucleotide comprising a silencing element operably linked to a seed-preferred promoter, wherein said silencing element, when ingested by a Pentatomidae plant pest, reduces the level of expression of any one of the target sequences set forth in SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 in said Pentatomidae plant pest and thereby controls the Pentatomidae plant pest. A plant cell may comprise a silencing element comprising a) a fragment of at least 19 consecutive nucleotides of SEQ ID NOS: 279, 302, 281, 304, 280, 283, 282, 303, 278, 284, 285, 286, 287, 288, 289, 290, 291, 292, 17, 30, 34, 14, 18 or 263 or a complement thereof; or, b) the nucleotide sequence comprising at least 90% sequence identity to any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof, wherein said silencing element, when ingested by a Pentatomidae plant pest, reduces the level of a target sequence in said Pentatomidae plant pest and thereby controls the Pentatomidae plant pest. For such a plant cell the Pentatomidae plant pest may be a *N. viridula* plant pest. In a plant cell of any one of embodiment 11, 12 or 13, wherein said silencing element comprises the sequences set forth in any one of SEQ ID NOS: 284, 285, 286, 287, 288, 289, 290, 291, 292, 305, 306, 307, 308, 309, 310, 311, 312, 17, 30, 34, 337, 338, 339, 340, 341, 342, 343 or 344 or a complement thereof. A plant cell may comprise an expression cassette disclosed herein. A plant cell may comprise a silencing element that expresses a double stranded RNA. A plant cell may comprise a silencing element that expresses a hairpin RNA. Such a plant cell comprises said polynucleotide comprising the silencing element comprises, in the following order, a first segment, a second segment, and a third segment, wherein a) said first segment comprises at least about 19 nucleotides having at least 90% sequence complementarity to a target sequence set forth in SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328; b) said second segment comprises a loop of sufficient length to allow the silencing element to be transcribed as a hairpin RNA; and, c) said third segment comprises at least about 19 nucleotides having at least 85% complementarity to the first segment.

An example of methods and compositions comprise a plant cell that is from a monocot. A monocot may be maize, barley, millet, wheat or rice. An example of methods and compositions comprise a plant cell that is from a dicot. A dicot may be soybean, canola, alfalfa, sunflower, safflower, tobacco, *Arabidopsis*, or cotton.

An example of methods and compositions comprise a plant or plant part comprising a plant cell disclosed herein. An example of methods and compositions comprise a transgenic seed from a plant disclosed herein, wherein said transgenic seed comprises said heterologous polynucleotide comprising said silencing element.

An example of methods and compositions comprise a method of controlling a Pentatomidae plant pest comprising feeding to a Pentatomidae plant pest a composition comprising a silencing element, wherein said silencing element, when ingested by said Pentatomidae plant pest, reduces the level of expression of any one of the target Pentatomidae plant pest sequences set forth in SEQ ID NOS: 279, 302, 281, 304, 280, 283, 282, 303, 278, 284, 285, 286, 287, 288, 289, 290, 291, 292, 17, 30, 34, 14, 18 or 263 and thereby controls the Pentatomidae plant pest. In a method, said silencing element comprises a) a fragment of at least 19 consecutive nucleotides of SEQ ID NOS: 279, 302, 281, 304, 280, 283, 282, 303, 278, 284, 285, 286, 287, 288, 289, 290, 291, 292, 17, 30, 34, 14, 18 or 263 or a complement thereof; or, b) the nucleotide sequence comprising at least 90% sequence identity to any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof, wherein said silencing element, when ingested by a Pentatomidae plant pest, reduces the level of a target sequence in said Pentatomidae plant pest and thereby controls the Pentatomidae plant pest. In a method, a Pentatomidae plant pest comprises a *N. viridula* plant pest. In a method, said silencing element comprises the sequence set forth in any one of SEQ ID NOS: 284, 285, 286, 287, 288, 289, 290, 291, 292, 305, 306, 307, 308, 309,310, 311, 312, 17,30, 34, 337, 338, 339, 340, 341, 342, 343 or 344 or a complement thereof. In a method, said composition comprises a plant or plant part having stably incorporated into its genome a polynucleotide comprising said silencing element, wherein said silencing element is operably linked to a seed-preferred promoter. In a method, said silencing element comprises a) a polynucleotide comprising the sense or antisense sequence of the sequence set forth in SEQ ID NOS: 284, 285, 286, 287, 288, 289, 290, 291, 292, 17, 30, 34, 14, 18, 263, 337, 338, 339, 340, 341, 342, 343, 344, 305, 306, 307, 308, 309, 310, 311 or 312 or a complement thereof; or, b) a polynucleotide comprising the sense or antisense sequence of a sequence having at least 95% sequence identity to the sequence set forth in SEQ ID NOS: 284, 285, 286, 287, 288, 289, 290, 291, 292, 17, 30, 34, 14, 18, 263, 337, 338, 339, 340, 341, 342, 343, 344, 305, 306, 307, 308, 309, 310, 311 or 312 or a complement thereof. In a method, said silencing element expresses a double stranded RNA. In a method, said silencing element comprises a hairpin RNA. In a method, said polynucleotide comprising the silencing element comprises, in the following order, a first segment, a second segment, and a third segment, wherein a) said first segment comprises at least about 20 nucleotides having at least 90% sequence complementarity to the target polynucleotide; b) said second segment comprises a loop of sufficient length to allow the silencing element to be transcribed as a hairpin RNA; and, c) said third segment comprises at least about 20 nucleotides having at least 85% complementarity to the first segment. In a method, said silencing element is flanked by a first operably linked convergent promoter at one terminus of the silencing element and a second operably linked convergent promoter at the opposing terminus of the polynucleotide, wherein the first and the second convergent promoters are capable of driving expression of the silencing element. In a method, said plant is a monocot. In a method, said monocot is maize, barley, millet, wheat or rice. In a method, said plant is a dicot. In a method, said plant is soybean, canola, alfalfa, sunflower, safflower, tobacco, *Arabidopsis*, or cotton.

The following examples are offered by way of illustration and not by way of limitation.

EXPERIMENTAL

Example 1

In Vitro Transcription dsRNA Screening Method

A high throughput survey of candidate genes from the stinkbug *Nezara viridula* was performed for their potential utility as a target for RNAi leading to mortality (insecticidal activity of RNAi). A library of over 1000 expressed sequence tags was subjected to in vitro transcription and individual samples tested against 2nd instar nymphs of *N. viridula*. The insects were fed the sample in an insect assay format. After 6 days, the number of dead nymphs was recorded. Table 1 provides the blast homology (Gene ID) of the various silencing elements (clone name) disclosed herein and also provides bioassay data demonstrating the insecticidal activity of the various sequences when fed to *N. viridula*.

TABLE 1

| clone name | Gene ID | 6 day score #dead/10 |
|---|---|---|
| inv1c.pk008.f8.f | no hits | 10 |
| inv1c.pk003.n13.f | conserved hypothetical protein | 10 |
| inv1c.pk003.o24.f | conserved hypothetical protein | 7 |
| inv1c.pk004.a3.f | cathepsin L1 precursor | 9 |
| inv1c.pk004.a23.f | no hits | 9 |
| inv1c.pk004.b4.f | forked protein | 8 |
| inv1c.pk004.b6.f | ribosomal protein L24e | 9 |
| inv1c.pk004.b17.f | no hits | 8 |
| inv1c.pk004.b23.f | nonspecific lipid transfer protein/sterol carrier protein | 9 |
| inv1c.pk004.c11.f | soldier specific protein | 7 |
| inv1c.pk004.c12.f | no hits | 10 |
| inv1c.pk004.d4.f | no hits | 8 |
| inv1c.pk004.d16.f | oligomycin sensitivity conferral protein//ATP synthase | 10 |
| inv1c.pk004.d17.f | no hits | 10 |
| inv1c.pk004.d19.f | no hits | 7 |
| inv1c.pk004.d20.f | no hits | 9 |
| inv1c.pk004.e6.f | mitochondrial protein PTCD3 | 10 |
| inv1c.pk004.e11.f | adapter molecule Crk | 10 |
| inv1c.pk004.e24.f | cytochrome P450 | 10 |
| inv1c.pk004.f2.f | no hits | 8 |
| inv1c.pk004.f10.f | no hits | 7 |
| inv1c.pk004.f12.f | no hits | 8 |
| inv1c.pk004.f17.f | similar to dipteran sequences | 7 |
| inv1c.pk004.f24.f | no hits | 8 |
| inv1c.pk004.g13.f | no hits | 8 |
| inv1c.pk004.g20.f | vertebrate homology | 9 |
| inv1c.pk004.g22.f | no hits | 10 |
| inv1c.pk004.g23.f | no hits | 8 |
| inv1c.pk004.h18.f | salivary protein | 10 |
| inv1c.pk004.h20.f | lin-52 homolog | 8 |

TABLE 1-continued

| clone name | Gene ID | 6 day score #dead/10 |
|---|---|---|
| inv1c.pk004.h21.f | cyclin t | 10 |
| inv1c.pk004.h23.f | similar to complement component 1 q subcomponent binding protein-like protein | 9 |
| inv1c.pk004.h24.f | similar to prefoldin subunit | 10 |
| inv1c.pk004.i1.f | hsp70 | 10 |
| inv1c.pk004.i4.f | serine/threonine kinase | 9 |
| inv1c.pk004.i7.f | no hits | 9 |
| inv1c.pk004.i14.f | cytochrome P450 | 10 |
| inv1c.pk005.f6.f | U6 snRNA-associated Sm-like protein | 7 |
| inv1c.pk005.f8.f | NADH dehydrogenase subunit 2 | 10 |
| inv1c.pk005.f20.f | apolipprotein D | 7 |
| inv1c.pk005.h1.f | similar to Gag protein | 10 |
| inv1c.pk005.i21.f | no hits | 8 |
| inv1c.pk005.j11.f | no hits | 8 |
| inv1c.pk005.j17.f | *Homo sapiens* 3 BAC RP11-666A9 | 9 |
| inv1c.pk005.k12.f | no hits | 7 |
| inv1c.pk005.l13.f | no hits | 10 |
| inv1c.pk005.m5.f | no hits | 10 |
| inv1c.pk005.m16.f | similar to translation initiation factor 3, subunit S8 | 8 |
| inv1c.pk006.j24.f | no hits | 9 |
| inv1c.pk006.k4.f | no hits | 7 |
| inv1c.pk006.k18.f | acyl-CoA binding protein | 7 |
| inv1c.pk006.k20.f | E3 ubiquitin ligase/zinc finger protein | 9 |
| inv1c.pk006.k21.f | no hits | 8 |
| inv1c.pk006.l7.f | nervana 3/similar to sodium/potassium-dependent atpase beta-2 subunit | 7 |
| inv1c.pk006.m2.f | no hits | 10 |
| inv1c.pk006.m13.f | no hits | 10 |
| inv1c.pk006.o14.f | no hits | 10 |
| inv1c.pk006.p4.f | ubiquinol-cytochrome c reductase complex 11 kDa protein | 10 |
| inv1c.pk006.p8.f | similar to ATPase inhibitor-like protein | 10 |
| inv1c.pk006.p11.f | 40S ribosomal protein S7 | 9 |
| inv1c.pk006.p14.f | similar to *Drosophila* and pea aphid sequences | 10 |
| inv1c.pk007.a5.f | homology to insect sequences (*Nasonia*, *Tribolium*, *Drosophila* | 8 |
| inv1c.pk007.b6.f | no hits | 9 |
| inv1c.pk007.c6.f | no hits | 10 |
| inv1c.pk007.c9.f | conserved hypothetical protein | 10 |
| inv1c.pk007.d17.f | putative ferritin | 10 |
| inv1c.pk007.e5.f | fatty acyl-CoA elongase | 10 |
| inv1c.pk007.e21.f | aldehyde dehydrogenase | 9 |
| inv1c.pk007.f1.f | no hits | 10 |
| inv1c.pk007.f9.f | beta-tubulin | 10 |
| inv1c.pk007.f12.f | no hits | 10 |
| inv1c.pk007.f19.f | mitochondrial import receptor subunit tom40 [*Aedes aegypti*] | 10 |
| inv1c.pk007.f24.f | no hits | 9 |
| inv1c.pk007.g6.f | no hits | 10 |
| inv1c.pk007.g17.f | putative odorant-binding protein precursor | 10 |
| inv1c.pk007.h7.f | no hits | 7 |
| inv1c.pk007.h11.f | no hits | 8 |
| inv1c.pk007.h19.f | no hits | 7 |
| inv1c.pk007.i7.f | transposase | 10 |
| inv1c.pk007.i16.f | venom prophenoloxidase-activating protease | 10 |
| inv1c.pk007.j14.f | no hits | 10 |
| inv1c.pk007.j19.f | no hits | 10 |
| inv1c.pk007.j21.f | conserved hypothetical protein | 9 |
| inv1c.pk007.j23.f | succinate dehydrogenase, cytochrome B small subunit | 7 |
| inv1c.pk007.j24.f | no hits | 8 |
| inv1c.pk007.k17.f | conserved hypothetical protein | 9 |
| inv1c.pk007.l5.f | no hits | 9 |
| inv1c.pk007.l8.f | transmembrane protein, putative | 9 |
| inv1c.pk007.l11.f | no hits | 10 |
| inv1c.pk007.m6.f | conserved hypothetical protein | 10 |
| inv1c.pk007.m21.f | no hits | 9 |
| inv1c.pk007.o14.f | proteasome beta subunit | 7 |
| inv1c.pk007.p17.f | no hits | 7 |
| inv1c.pk008.c8.f | ribosomal protein L35Ae | 7 |

TABLE 1-continued

| clone name | Gene ID | 6 day score #dead/10 |
|---|---|---|
| inv1c.pk008.c15.f | similar to prohibitin | 8 |
| inv1c.pk008.c17.f | no hits | 7 |
| inv1c.pk008.d1.f | conserved hypothetical protein | 9 |
| inv1c.pk008.d3.f | conserved hypothetical protein | 7 |
| inv1c.pk008.e11.f | no hits | 10 |
| inv1c.pk008.e15.f | no hits | 10 |
| inv1c.pk008.f3.f | conserved hypothetical protein | 9 |
| inv1c.pk008.f5.f | no hits | 8 |
| inv1c.pk008.f8.f | no hits | 10 |
| inv1c.pk008.f23.f | no hits | 10 |
| inv1c.pk008.g7.f | no hits | 7 |
| inv1c.pk008.g22.f | no hits | 7 |
| inv1c.pk008.h23.f | putative ribosomal protein S26 | 10 |
| inv1c.pk008.h24.f | similar to mevalonate kinase | 10 |
| inv1c.pk008.i10.f | no hits | 9 |
| inv1c.pk008.i21.f | putative accessory gland protein | 9 |
| inv1c.pk008.j20.f | similar to eukaryotic translation initiation factor 3 subunit 2 beta | 8 |
| inv1c.pk008.k24.f | no hits | 7 |
| inv1c.pk008.l11.f | similar to phosphatase and actin regulator | 9 |
| inv1c.pk008.p18.f | no hits | 9 |
| inv1c.pk009.b14.f | no hits | 8 |
| inv1c.pk009.b21.f | ribosomal protein S20 | 7 |
| inv1c.pk009.e9.f | no hits | 9 |
| inv1c.pk009.e10.f | similar to sarco(endo)plasmic reticulum-type calcium ATPase | 7 |
| inv1c.pk009.e17.f | similar to serine/threonine protein kinase death domain protein, pelle-like | 9 |
| inv1c.pk009.f12.f | no hits | 10 |
| inv1c.pk009.f17.f | no hits | 7 |
| inv1c.pk009.f19.f | no hits | 9 |
| inv1c.pk009.g2.f | no hits | 8 |
| inv1c.pk009.g21.f | no hits | 8 |
| inv1c.pk009.h21.f | no hits | 10 |
| inv1c.pk009.i13.f | no hits | 10 |
| inv1c.pk009.i24.f | no hits | 7 |
| inv1c.pk009.k4.f | no hits | 8 |
| inv1c.pk009.k8.f | conserved hypothetical protein | 10 |
| inv1c.pk010.a13.f | no hits | 7 |
| inv1c.pk010.a16.f | arginyl-tRNA synthetase | 7 |
| inv1c.pk010.b7.f | similar to tar RNA binding protein | 10 |
| inv1c.pk010.e5.f | no hits | 7 |
| inv1c.pk010.n9.f | no hits | 7 |
| inv1c.pk010.n24.f | no hits | 10 |
| inv1c.pk010.p16.f | cytochrome c oxidase subunit II | 7 |
| inv1c.pk010.p20.f | no hits | 8 |
| inv1c.pk011.a20.f | no hits | 7 |
| inv1c.pk011.b11.f | no hits | 7 |

Sequences displaying insecticidal activity are advanced to confirmation and further evaluation of activity against other stinkbug pests. The assay is scored for activity 6 days post infestation. The possible scores are dead, severely stunted (little or now growth but alive), stunted (growth to second instar but not equivalent to controls), or no activity. Samples demonstrating mortality or severe stunting are advanced to confirmation.

Following confirmation, a simple dose response assay is performed with *N. viridula*. Samples for dose response assays is produced in the same manner with the following modification; samples is further purified using column purification prior to enzymatic treatment. Samples is also normalized to 0.5 ug/ul and all samples are evaluated by gel electrophoresis. Dose response assays is performed with the following rates; 50, 25, 12, 6, 3, and 1.5 ppm

Example 2

Sequences Having Insecticidal Activity

DNA sequences which encode double stranded RNAs which were shown to have insecticidal activity against *N. viridula* using the assay described in Example 1 are set forth in SEQ ID NOS: 1-139.

Example 3

Transformation of Maize

Immature maize embryos from greenhouse donor plants are bombarded with a plasmid containing the silencing element of the invention operably linked to either a tissue specific, tissue selective, or constitutive promoter and the selectable marker gene PAT (Wohlleben et al. (1988) *Gene* 70:25-37), which confers resistance to the herbicide Bialaphos. In one embodiment, the promoter employed is a seed-preferred promoter. In one embodiment, the constructs will express a long double stranded RNA or a miRNA of the target sequence set forth in SEQ ID NOS: 1-292 or 302-304 or a fragment thereof. In specific embodiments, the target sequence comprises the sequences set forth in SEQ ID NOS: 278, 279, 280, 281, 282, 283, 302, 303 or 304. Such a construct can be linked to a promoter active in maize. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to either the tissue specific, tissue selective, or constitutive promoter is made. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity.

Plants are monitored and scored for the appropriate marker, such as the control of a Pentatomidae plant pest, such as a *N. viridula* plant pest. For example, Ro maize plants are fed to *N. viridula* 2nd instar nymphs. Contamination and larval quality are monitored. Larval mass and survivorship are recorded for analysis. A one-way ANOVA analysis and a Dunnett's test is performed on the larval mass data to look for statistical significance compared to an untransformed negative control maize plant diet. *N. viridula* $2^{nd}$ instar nymph stunting is measured after feeding on two events and compared to growth of larvae fed on negative control plants.

In other assays, transgenic corn plants (Ro) generated are planted into 10-inch pots containing Metromix soil after reaching an appropriate size. After allowing the *N. viridula* $2^{nd}$ instar nymphs to feed on the plant, plants are removed from the soil and washed so that the relevant plant parts can be evaluated for larval feeding. Plant damage is rated using routine methods to score the level of damage.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/12,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 4

*Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Such a construct can, for example, express a long double stranded RNA or a miRNA of the target sequence set forth in SEQ ID NOS: 1-292 or 302-304. In one embodiment, the promoter employed is a seed-preferred promoter. In specific embodiments, the target sequence comprises the sequence set forth in SEQ ID NOS: 278, 279, 280, 281, 282, 283, 302, 303 or 304. Such a construct can be linked to the dMMB promoter. Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants. Assays for insecticidal activity can be performed as described above in Example 3.

Example 5

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 g/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with a plasmid containing the silencing element of the invention operably linked to either a tissue specific, tissue selective, or constitutive promoter by the method of particle gun bombardment (Klein et al. (1987) *Nature,* 327:70). In one embodiment, the promoter employed is a seed-preferred promoter. In one embodiment, the constructs will express a long double stranded RNA or a miRNA of the target sequence set forth in SEQ ID NOS: 1-292 or 302-304 or a fragment thereof. In specific embodiments, the target sequence comprises the sequences set forth in SEQ ID NOS: 278, 279, 280, 281, 282, 283, 302, 303 or 304.

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing silencing element of interest are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 μl 2.5M $CaCl_2$ and 20 μl of 0.1 M spermidine. The mixture is shaken 3 min on level 3 of a vortex shaker and spun for 10 sec in a bench microfuge. After a wash with 400 μl 100% ethanol the pellet is suspended by sonication in 40 μl of 100% ethanol. Five μl of DNA suspension is dispensed to each flying disk of the Biolistic PDS1000/HE instrument disk. Each 5 μl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the appropriate marker or the ability of the plant, when injected with the silencing elements, to control the Pentatomidae plant pest or the *N. viridula* plant pest.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |

-continued

| Stock # | | 1000 ml | 500 ml |
|---|---|---|---|
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat#21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide

Example 6

Expression of Silencing Elements Comprising siRNAs

SiRNAs were generated to target the cDNA sequence set forth in SEQ ID NOS: 140, 143, 146, 149, 152, 155, 158, 161, 164, 167, 170, 173, 176, 179, 182, 185, 188, 191, 194, 197, 200, 203, 206, 209, 212, 215, 218, 221, 224, 227, 230, 233, 236, 239, 242, 245, 248, 251, 254, 257, 260, 263, 266, 269, 273, and 276. Table 2 provides the clone name of the silencing element and the closest homology for the target sequence (gene name). Table 3 provides the clone name, the target cDNA, the sense and antisense siRNA sequence, and the respective SEQ ID NOS. Table 4 provides the bioassays for each of the siRNAs shown in Table 3.

TABLE 2

| Query Sequence Title (ID) | gene name |
|---|---|
| inv1c.pk003.j16.f | conserved protein of unknown function |
| inv1c.pk003.j16.f | conserved protein of unknown function |
| inv1c.pk004.b7.f | cathepsin L |
| inv1c.pk004.b7.f | cathepsin L |
| inv1c.pk004.b7.f | cathepsin L |
| inv1c.pk004.b7.f | cathepsin L |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.f4.f | reverse transcriptase |
| inv1c.pk004.f4.f | reverse transcriptase |
| inv1c.pk004.f4.f | reverse transcriptase |
| inv1c.pk004.j14.f | sugar transporter |
| inv1c.pk004.k9.f | glutathione s transferase |
| inv1c.pk004.k9.f | glutathione s transferase |
| inv1c.pk004.k9.f | glutathione s transferase |
| inv1c.pk005.a24.f | cathepsin L-like protease |
| inv1c.pk005.a24.f | cathepsin L-like protease |
| inv1c.pk005.b16.f | synapsin |
| inv1c.pk005.b16.f | synapsin |
| inv1c.pk005.b16.f | synapsin |
| inv1c.pk005.b16.f | synapsin |
| inv1c.pk005.b16.f | synapsin |
| inv1c.pk005.f20.f | Apolipoprotein D precursor |
| inv1c.pk005.f20.f | Apolipoprotein D precursor |
| inv1c.pk005.f20.f | Apolipoprotein D precursor |
| inv1c.pk005.f20.f | Apolipoprotein D precursor |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h23.f | chitin synthase 1 |
| inv1c.pk005.j19.f | conserved hypothetical protein |
| inv1c.pk005.j19.f | conserved hypothetical protein |
| inv1c.pk005.k24.f | cathepsin B |
| inv1c.pk005.k24.f | cathepsin B |

TABLE 3

| siRNA number | Query Sequence Title (ID) | No. Bases | Target Location | Approx. Target Location (thirds) | Target cDNA Sequence | % CG | Sense Strand siRNA | Antisense siRNA Sequence | SEQ ID NOS Target cDNA/ sense siRNA/ antisense siRNA |
|---|---|---|---|---|---|---|---|---|---|
| 1 | inv1c.pk003.j16.f | 656 | 227 | 2 | AATCAAGGTGTGGA CTGAAAATT | 34.8 | UCAAGGUGUG GACUGAAAA | UUUUCAGUCCA CACCUUGA | 140/141/142 |
| 2 | inv1c.pk003.j16.f | 656 | 490 | 3 | AATTGGTTGCTACAT ATTCTCTT | 30.4 | UUGGUUGCUA CAUAUUCUC | GAGAAUAUGUA GCAACCAA | 143/144/145 |
| 3 | inv1c.pk004.b7.f | 603 | 150 | 1 | AAGAACGTCTTAGG ATGCATATT | 34.8 | GAACGUCUUA GGAUGCAUA | UAUGCAUCCUA AGACGUUC | 146/147/148 |

TABLE 3-continued

| siRNA number | Query Sequence Title (ID) | No. Bases | Target Location | Approx. Target Location (thirds) | Target cDNA Sequence | % CG | Sense Strand siRNA | Antisense siRNA Sequence | SEQ ID NOS Target cDNA/ sense siRNA/ antisense siRNA |
|---|---|---|---|---|---|---|---|---|---|
| 4 | inv1c.pk004.b7.f | 603 | 317 | 2 | AAGCAAGCACCTAC CTTCACATT | 43.5 | GCAAGCACCU ACCUUCACA | UGUGAAGGUAG GUGCUUGC | 149/150/151 |
| 5 | inv1c.pk004.b7.f | 603 | 412 | 3 | AAACCAAGGTAGCT GTGGATCTT | 43.5 | ACCAAGGUAG CUGUGGAUC | GAUCCACAGCU ACCUUGGU | 152/153/154 |
| 6 | inv1c.pk004.b7.f | 603 | 545 | 3 | AATAATGGATGTGG TGGCGGATT | 43.5 | UAAUGGAUGU GGUGGCGGA | UCCGCCAC- CACA UCCAUUA | 155/156/157 |
| 7 | inv1c.pk004.c4.f | 688 | 133 | 1 | AAAAGGATACCACT TTGGACTTT | 34.8 | AAGGAUACCA CUUUGGACU | AGUCCAAAGUG GUAUCCUU | 158/159/160 |
| 8 | inv1c.pk004.c4.f | 688 | 134 | 1 | AAAGGATACCACTT TGGACTTTT | 34.8 | AGGAUACCAC UUUGGACUU | AAGUCCAAAGU GGUAUCCU | 161/162/163 |
| 9 | inv1c.pk004.c4.f | 688 | 171 | 1 | AAACCAAGACCCAG ACTGGAGTT | 47.8 | ACCAAGACCC AGACUGGAG | CUCCAGUCUGG GUCUUGGU | 164/165/166 |
| 10 | inv1c.pk004.c4.f | 688 | 176 | 1 | AAGACCCAGACTGG AGTTGAATT | 43.5 | GACCCAGACU GGAGUUGAA | UUCAACUCCAG UCUGGGUC | 167/168/169 |
| 11 | inv1c.pk004.c4.f | 688 | 218 | 1 | AACCAAGAAACTGG GAAAGTGTT | 39.1 | CCAAGAAACU GGGAAAGUG | CACUUUCCCAG UUUCUUGG | 170/171/172 |
| 12 | inv1c.pk004.c4.f | 688 | 226 | 1 | AACTGGGAAAGTGT TCGGAAATT | 29.1 | CUGGGAAAGU GUUCGGAAA | UUUCCGAACAC UUUCCCAG | 173/174/175 |
| 13 | inv1c.pk004.c4.f | 688 | 322 | 2 | AACTGAAATTGCCCT CACTGATT | 39.1 | CUGAAAUUGC CCUCACUGA | UCAGUGAGGGC AAUUUCAG | 176/177/178 |
| 14 | inv1c.pk004.c4.f | 688 | 359 | 2 | AAGCTTTCTTGTGAT ACCTCATT | 34.8 | GCUUUCUUGU GAUACCUCA | UGAGGUAUCAC AAGAAAGC | 179/180/181 |
| 15 | inv1c.pk004.c4.f | 688 | 431 | 2 | AATGATACGTGTGCT TTGAACTT | 34.8 | UGAUACGUGU GCUUUGAAC | GUUCAAAGCAC ACGUAUCA | 182/183/184 |
| 16 | inv1c.pk004.c4.f | 688 | 619 | 3 | AAGCATTAATGATG GACGTGTTT | 34.8 | GCAUUAAUGA UGGACGUGU | ACACGUCCAUC AUUAAUGC | 185/186/187 |
| 17 | inv1c.pk004.f4.f | 696 | 368 | 2 | AAAACTTTCTCAAA GAACCAGTTT | 30.4 | AACUUUCUCA AAGAACCAG | CUGGUUCUUUG AGAAAGUU | 188/189/190 |
| 18 | inv1c.pk004.f4.f | 696 | 379 | 2 | AAAGAACCAGTTCC AAATGCATT | 34.8 | AGAACCAGUU CCAAAUGCA | UGCAUUUGGAA CUGGUUCU | 191/192/193 |
| 19 | inv1c.pk004.f4.f | 696 | 394 | 2 | AATGCATTCCCTTCA ATCTCATT | 34.8 | UGCAUUCCCU UCAAUCUCA | UGAGAUUGAAG GGAAUGCA | 194/195/196 |
| 20 | inv1c.pk004.j14.f | 687 | 533 | 3 | AACCTCTCCTCGTCT GGAGTCTT | 52.2 | CCUCUCCUCG UCUGGAGUC | GACUCCAGACG AGGAGAGG | 197/198/199 |
| 21 | inv1c.pk004.k9.f | 663 | 212 | 1 | AAAGAATTCACCTG GTCCTACTT | 39.1 | AGAAUUCACC UGGUCCUAC | GUAGGACCAGG UGAAUUCU | 200/201/202 |
| 22 | inv1c.pk004.k9.f | 663 | 531 | 3 | AATTCTGGAAGAAA TGGACCATT | 34.8 | UUCUGGAAGA AAUGGACCA | UGGUCCAUUUC UUCCAGAA | 203/204/205 |
| 23 | inv1c.pk004.k9.f | 663 | 641 | 3 | AACGTCTAGAAATG GTGAGAGTT | 39.1 | CGUCUAGAAA UGGUGAGAG | CUCUCACCAUU UCUAGACG | 206/207/208 |
| 24 | inv1c.pk005.a24.f | 443 | 198 | 2 | AATAAGAAACACGA AGCAGGCTT | 39.1 | UAAGAAACAC GAAGCAGGC | GCCUGCUUCGU GUUUCUUA | 209/210/211 |
| 25 | inv1c.pk005.a24.f | 443 | 271 | 2 | AAATGAAGAGCCAT TTAGGCTTT | 34.8 | AUGAAGAGCC AUUUAGGCU | AGCCUAAAUGG CUCUUCAU | 212/213/214 |
| 26 | inv1c.pk005.b16.f | 680 | 17 | 1 | AACTTCGAACCATCT CCCCGGTT | 52.2 | CUUCGAACCA UGUCCCCGG | CCGGGGAGAUG GUUCGAAG | 215/216/217 |
| 27 | inv1c.pk005.b16.f | 680 | 119 | 1 | AAGCTTCCTTCACTA CAAATGTT | 34.8 | GCUUCCUUCA CUACAAAUG | CAUUUGUAGUG AAGGAAGC | 218/219/220 |

TABLE 3-continued

| siRNA number | Query Sequence Title (ID) | No. Bases | Target Location | Approx. Target Location (thirds) | Target cDNA Sequence | % CG | Sense Strand siRNA | Antisense siRNA Sequence | SEQ ID NOS Target cDNA/ sense siRNA/ antisense siRNA |
|---|---|---|---|---|---|---|---|---|---|
| 28 | /inv1c.pk005.b16.f | 680 | 156 | 1 | AAGGTTCAGCTCCG GGGATCTTT | 52.2 | GGUUCAGCUC CGGGGAUCU | AGAUCCCCGGA GCUGAACC | 221/222/223 |
| 29 | inv1c.pk005.b16.f | 680 | 540 | 3 | AATCGACGACCAAA ATACTGATT | 34.8 | UCGACGACCA AAAUACUGA | UCAGUAUUUUG GUCGUCGA | 224/225/226 |
| 30 | inv1c.pk005.b16.f | 680 | 569 | 3 | AATACTTCAGAGTA CGGCGTATT | 39.1 | UACUUCAGAG UACGGCGUA | UACGCCGUACU CUGAAGUA | 227/228/229 |
| 31 | inv1c.pk005.f20.f | 662 | 46 | 1 | AAAATGAGAGCTAC GTACTGCTT | 39.1 | AAUGAGAGCU ACGUACUGC | GCAGUACGUAG CUCUCAUU | 230/231/232 |
| 32 | inv1c.pk005.f20.f | 662 | 316 | 2 | AAATACCATTACAC AGGACATTT | 30.4 | AUACCAUUAC ACAGGACAU | AUGUCCUGUGU AAUGGUAU | 233/234/235 |
| 33 | inv1c.pk005.f20.f | 662 | 387 | 2 | AAGTGTTGCTGGAA CATCAAGTT | 39.1 | GUGUUGCUGG AACAUCAAG | CUUGAUGUUCC AGCAACAC | 236/237/238 |
| 34 | inv1c.pk005.f20.f | 662 | 605 | 3 | AATGCCCAGCAGAA ACCAACCTT | 47.8 | UGCCCCAGCAG AAACCAACC | GGUUGGUUUCU GCUGGGCA | 239/240/241 |
| 35 | inv1c.pk005.h1.f | 628 | 143 | 1 | AAATACCACAGCCA GCAATAATT | 34.8 | AUACCACAGC CAGCAAUAA | UUAUUGCUGGC UGUGGUAU | 242/243/244 |
| 36 | inv1c.pk005.h1.f | 628 | 144 | 1 | AATACCACAGCCAG CAATAATTT | 34.8 | UACCACAGGC AGCAAUAAU | AUUAUUGCUGG CUCUGGUA | 245/246/247 |
| 37 | inv1c.pk005.h1.f | 628 | 192 | 1 | AAGCCTCCGGTACCT CAAGGTTT | 52.2 | GCCUCCGGUA CCUCAAGGU | ACCUUGAGGUA CCGGAGGC | 248/249/250 |
| 38 | inv1c.pk005.h1.f | 628 | 288 | 2 | AATCTTATCGGACA AACCAGTTT | 34.8 | UCUUAUCGGA CAAACCAGU | ACUGGUUUGUC CGAUAAGA | 251/252/253 |
| 39 | inv1c.pk005.h1.f | 628 | 556 | 3 | AAAAATATCCATTG CCACTGTTT | 30.4 | AAAUCUCCAU UGCCACUGU | ACAGUGGCAAU GGAUAUUU | 254/255/256 |
| 40 | inv1c.pk005.h1.f | 628 | 557 | 3 | AAAATATCCATTGCC ACTGTTTT | 30.4 | AAUAUCCAUU GCCACUGUU | AACAGUGGCAA UGGAUAUU | 257/258/259 |
| 41 | inv1c.pk005.h1.f | 628 | 558 | 3 | AAATATCCATTGCCA CTGTTTTT | 30.4 | AUAUCCAUUG CCACUGUUU | AAACAGUGGCA AUCCAUAU | 260/261/262 |
| 42 | inv1c.pk005.h23.f | 647 | 301 | 2 | AAGGATGGGATGTG TTCCGAGTT | 47.8 | GGAUGGGAUG UGUUCCGAG | CUCGGAACACA UCCCAUCC | 263/264/265 |
| 43 | inv1c.pk005.j19.f | 597 | 172 | 1 | AAGATGGGGGGATG ATGTACGTT | 47.8 | GAUGGGGGGA UGAUGUACG | CGUACAUCAUC CCCCCAUC | 266/267/268 |
| 44 | inv1c.pk005.j19.f | 597 | 377 | 2 | AAGAACATCCACAG GAGAACCTT | 43.5 | GAACAUCCAC AGGAGAACC | GGUUCUCCUGU GGAUGUUC | 269/270/271 |
| 45 | inv1c.pk005.k24.f | 593 | 27 | 1 | AAGACTCTATTAATA TCCAGCTT | 30.4 | GACUCUAUUA AUAUCCAGC | GCUGGAUAUUA AUAGAGUC | 272/273/274 |
| 46 | inv1c.pk005.k24.f | 593 | 132 | 1 | AAATGGAAAGCTGG GCAGAACTT | 43.5 | AUGGAAAGCU GGGCAGAAC | GUUCUGCCCAG CUUUCCAU | 275/276/277 |

(Note:
the sense RNA primer sequence and the antisense RNA primer sequences shown in table 3 were generated having 2 thymine residues at the 3' end.)

TABLE 4

| siRNA number | Query Sequence Title (ID) | Bioassay-1 100 ppm (4 day score) | Bioassay-1 100 ppm (5 day score) | Bioassay-2 100 ppm (5 day score) | Comment | Bioassay-3 100 ppm (5 day score) | Bioassay-4 25 ppm 5 day | Bioassay-5 25 ppm | Bioassay-6 50 ppm |
|---|---|---|---|---|---|---|---|---|---|
| 1 | inv1c.pk003.j16.f | 3/9 | | 10/10 | | 8/10 | ND | | |
| 2 | inv1c.pk003.j16.f | 4/11 | | 10/10 | | 1/10 | ND | | |
| 3 | inv1c.pk004.b7.f | 11/12 | | 10/10 | | ND | ND | | |
| 4 | inv1c.pk004.b7.f | 7/11 | | 10/10 | | | 0/10 | | |
| 5 | inv1c.pk004.b7.f | 6/9 | | 9/10 | | | 0/10 | | |

TABLE 4-continued

| siRNA number | Query Sequence Title (ID) | Bioassay-1 100 ppm (4 day score) | Bioassay-1 100 ppm (5 day score) | Bioassay-2 100 ppm (5 day score) | Comment | Bioassay-3 100 ppm (5 day score) | Bioassay-4 25 ppm 5 day | Bioassay-5 25 ppm | Bioassay-6 50 ppm |
|---|---|---|---|---|---|---|---|---|---|
| 6 | inv1c.pk004.b7.f | 5/11 | | 3/10 | | | | | |
| 7 | inv1c.pk004.c4.f | 3/9 | | 1/10 | | | | | |
| 8 | inv1c.pk004.c4.f | 3/10 | | 0/10 | | | | | |
| 9 | inv1c.pk004.c4.f | 4/10 | | 4/10 (5 stunted) | | | 0/10 | | |
| 10 | inv1c.pk004.c4.f | 3/10 | | 5/10 (3 stunted) | | | 1/10 | | |
| 11 | inv1c.pk004.c4.f | 4/10 | | 2/10 | | | | | |
| 12 | inv1c.pk004.c4.f | 5/9 | | 0/10 | | | | | |
| 13 | inv1c.pk004.c4.f | 7/10 | | 1/10 | | | | | |
| 14 | inv1c.pk004.c4.f | 4/10 | | 2/10 | | | | | |
| 15 | inv1c.pk004.c4.f | 5/9 | | 1/10 | | | | | |
| 16 | inv1c.pk004.c4.f | 6/10 | | 0/10 | | | | | |
| 17 | inv1c.pk004.f4.f | 5/10 | | 3/10 (2 stunted) | | | | | |
| 18 | inv1c.pk004.f4.f | 2/11 | | 3/10 (2 stunted) | | | | | |
| 19 | inv1c.pk004.f4.f | 6/9 | | 0/10 | | | | | |
| 20 | inv1c.pk004.j14.f | 6/10 | | 0/10 | | | | | |
| 21 | inv1c.pk004.k9.f | | 10/10 | | | 0/10 | | | |
| 22 | inv1c.pk004.k9.f | | 6/11 | | | 1/10 | | | |
| 23 | inv1c.pk004.k9.f | | 3/10 | | | 2/10 | | | |
| 24 | inv1c.pk005.a24.f | | 10/10 | 0/10 | | | | | |
| 25 | inv1c.pk005.a24.f | | | 0/10 | | | | | |
| 26 | inv1c.pk005.b16.f | | | 0/10 | Significant growth in survivors | | | | |
| 27 | inv1c.pk005.b16.f | | | 5/10 | Significant growth in survivors | | | | |
| 28 | inv1c.pk005.b16.f | | | 5/10 | Significant growth in survivors | | | | |
| 29 | inv1c.pk005.b16.f | | | 4/10 | Significant growth in survivors | | | | |
| 30 | inv1c.pk005.b16.f | | | 0/10 | | | | | |
| 31 | inv1c.pk005.f20.f | | | 9/10 | No growth | | 1/10 | | |
| 32 | inv1c.pk005.f20.f | | | 10/10 | Some growth before death | | 1/10 | | |
| 33 | inv1c.pk005.f20.f | | | 10/10 | Growth before death | | 2/10 (survivors stunted) | 4/10 | 8/10 |
| 34 | inv1c.pk005.f20.f | | | 4/10 | Growth before death | | | | |
| 35 | inv1c.pk005.h1.f | | | 7/10 | Growth before death | | 1/10 (some stunting) | | |
| 36 | inv1c.pk005.h1.f | | | 10/10 | some growth before death | | 1/10 | | |
| 37 | inv1c.pk005.h1.f | | | 10/10 | Growth before death | | 0/10 | | |
| 38 | inv1c.pk005.h1.f | | | 10/10 | no growth | | 1/10 | | |
| 39 | inv1c.pk005.h1.f | | | 1/10 | | | | | |
| 40 | inv1c.pk005.h1.f | | | 8/10 | little growth | | 0/10 | | |
| 41 | inv1c.pk005.h1f | | | 6/10 | some growth | | | | |
| 42 | inv1c.pk005.h23.f | | | 7/10 | No growth | | 0/10 | | |
| 43 | inv1c.pk005.j19.f | | | 10/10 | No growth | | 2/10 | | |
| 44 | inv1c.pk005.j19.f | | | | | | 1/10 | | |
| 45 | inv1c.pk005.k24.f | | | | | | 0/10 | | |
| 46 | inv1c.pk005.k24.f | | | | | | 0/10 | 5/10 | |

Example 7

Constructs Expressing siRNAs siRNAs designed to target the cDNA sequence set forth in SEQ ID NOS: 140, 143, 146, 149, 152, 155, 158, 161, 164, 167, 170, 173, 176, 179, 182, 185, 188, 191, 194, 197, 200, 203, 206, 209, 212, 215, 218, 221, 224, 227, 230, 233, 236, 239, 242, 245, 248, 251, 254, 257, 260, 263, 266, 269, 272, and 275 can be engineered to be expressed in planta. The construct can comprise, for example, the maize ubiquitin promoter/5'UTR/1$^{st}$ intron operably linked to a sequence comprising SEQ ID NO: 141 which is operably linked to the ADH1 intron followed by the sequence comprising SEQ ID NO: 142. It is recognized that any of the siRNA described in Example 6 can be generated employing a similar construct design.

Example 8

Generation of Silencing Constructs for In Vivo Testing Experiments

The activity of 9 dsRNAs listed in Table 1, was confirmed on repeated testing and the target genes advanced for further evaluation in in planta assays. For this purpose, 2 different types of constructs were assembled. In one, 2 SGSB target gene fragments, separated by a spiceosomal intron, were assembled in opposite orientations with respect to each other to produce a hairpin RNA. In planta produced hairpin RNAs are expected to be processed to yield siRNAs which upon uptake into insects, mediate RNAi inhibition of SGSB target gene expression. In the second, small 21-mer SGSB gene sequences are incorporated into a micro RNA backbone to produce an artificial pre-miRNA. Processing of the pre-miRNA in vivo releases the 21-nt miRNA that targets the SGSB gene for silencing. Hairpin constructs for in vivo expression and testing of dsRNAs were assembled via Gateway technology using procedures and practices well known to those skilled in the art of molecular biology. Target gene fragments were generated by PCR using gene specific sense and antisense primers containing Gateway attB4 (CAACTTTGTATAGAAAAGTTG (SEQ ID NO: 345)) and attB3 (CAACTTTGTATAATAAAGTTG (SEQ ID NO: 346)) sequences, respectively. The amplified DNA fragments were recombined into the pDONR vector, PHP36164 containing attP4-attP3 sites in a reaction catalyzed by BP Clonase. The resultant entry clones containing target gene fragments flanked by attL 4 and attL3 sites were then used to generate an expression construct by performing 2 sequential LR recombination reactions, first with the vector pKB499 and then with the vector PHP25224. The former destination vector contains the 193 bp intron2 fragment of the potato LS1 gene flanked by attR4-R3 sites at the 5' end and attR3-R4 sites at the 3' end. LR recombination yields a hairpin segment comprised of sense and antisense target gene fragments separated by an intron loop. In planta expression is regulated by placement of the appropriate regulatory elements, promoter sequences upstream and termination sequences downstream, of the hairpin segment. In this particular example, promoter sequences are provided by a 1946 bp soybean ubiquitin promoter-5' UTR-Intron1 fragment and termination sequences are provided by an 888 bp 3' fragment of the *Arabidopsis* ubiquitin10 gene. Other promoter sequences providing constitutive or appropriate tissue specific expression may additionally be used. The final plant expression construct is produced by a second LR reaction in which the entire hairpin cassette is moved into a vector (PHP25224) which provides a plant selectable marker (herbicide resistant acetolactate synthase gene) for stable transformation experiments. In Table 5, the 9 entries correspond to hairpin constructs that were assembled and tested in soybean embryos for efficacy against Southern Green Stinkbug (SGSB).

TABLE 5

Hairpin constructs for SGSB target gene silencing

| Gene ID | SEQ length (bp) | SEQ ID NO | Fragment Location | Fragment SEQ ID NO | Construct | Construct SEQ ID NO (without promoter) |
|---|---|---|---|---|---|---|
| inv1c.pk004.e6.f:fis | 1054 | 278 | 2-537 | 284 | PHP49713 | 293 |
| inv1c.pk004.h20.f:fis | 861 | 279 | 72-677 | 285 | PHP48181 | 294 |
| inv1c.pk004.h20.f:fis | 861 | 279 | 72-834 | 286 | pKB505 | 295 |
| inv1c.pk004.h20.f:fis | 861 | 279 | 72-439 | 287 | pKB506 | 296 |
| inv1c.pk004.i1.f:fis | 992 | 280 | 27-511 | 288 | PHP48183 | 297 |
| inv1c.pk004.i1.f:fis | 992 | 280 | 488-938 | 289 | pKB508 | 298 |
| inv1c.pk008.m9.f:fis | 858 | 281 | 2-800 | 290 | PHP49450 | 299 |
| inv1c.pk011.f6.f:fis | 792 | 282 | 19-594 | 291 | PHP49451 | 300 |
| inv1c.pk010.g13.f:fis | 643 | 283 | 4-785 | 292 | PHP49480 | 301 |

Silencing constructs encoding artificial microRNAs (amiRNAs) that would have the ability to silence Southern Green Stinkbug genes were designed largely according to rules described in Schwab R, et al. (2005) *Dev Cell* 8: 517-27. To summarize, microRNA sequences are 21 nucleotides in length, start at their 5'-end with a "U", display 5' instability relative to their star sequence which is achieved by including a C or G at position 19, and their 10th nucleotide is either an "A" or an "U". An additional requirement for artificial microRNA design was that the amiRNA have a high free delta-G as calculated using the ZipFold algorithm (Markham, N. R. & Zuker, M. (2005) *Nucleic Acids Res.* 33: W577-W581.) Optionally, a one base pair change was added to the 5' portion of the amiRNA so that the sequence differed from the target sequence by one nucleotide. The amiRNAs that were used to silence SGSB genes are given in Table 6.

TABLE 6 amiRNA Sequences

| amiRNA precursor | GENE ID | Target SEQ ID NO | amiRNA Sequence | amiRNA SEQ ID NO |
|---|---|---|---|---|
| Nv-MCS Frg1 | inv1c.pk005.h23.f | 302 | taagtaccatgtccaacgcca | 305 |
| Nv-MCS Frg2 | inv1c.pk005.h23.f | 302 | tattacaataactgaccaccc | 306 |
| Nv-MMitpro2 | inv1c.pk004.e6.f:fis | 278 | tcctactacatatttccaccc | 307 |

TABLE 6-continued

| amiRNA Sequences | | | | |
|---|---|---|---|---|
| amiRNA precursor | GENE ID | Target SEQ ID NO | amiRNA Sequence | amiRNA SEQ ID NO |
| Nv-MitprotCD3 | inv1c.pk004.e6.f:fis | 278 | tattccttctatcttctccca | 308 |
| Nv-Madapmol2 | inv1c.pk004.e11.f:fis | 303 | taaagtatattaataattctt | 309 |
| Nv-MadadapCRK1 | inv1c.pk004.e11.f:fis | 303 | ttactatcttcccttacacaa | 310 |
| Nv-MNH1A | inv1c.pk004.d17.f:fis | 304 | tacgaagagataacacaagat | 311 |
| Nv-MNH1B | inv1c.pk004.d17.f:fis | 304 | taacaaaacaaaaaaaaactg | 312 |

"Star sequences" are those that base pair with the amiRNA sequences in the precursor RNA, to form imperfect stem structures. To form a perfect stem structure the star sequence would be the exact reverse complement of the amiRNA. The soybean precursor sequence miR159 as described in Zhang, B. at al. (2008) *Planta* 229:161-182 was folded with MFold (M. Zuker (2003) *Nucleic Acids Res.* 31: 3406-15; and D. H. Mathews, J. et al. (1999) *J. Mol. Biol.* 288: 911-940). The miRNA sequence was then replaced with the amiRNA sequence and the endogenous star sequence was replaced with the exact reverse complement of the amiRNA. Changes in the artificial star sequence were introduced so that the structure of the stem would remain the same as the endogenous structure. The altered sequence was then folded with mfold and the original and altered structures were compared by eye. If necessary, further alternations to the artificial star sequence were introduced to maintain the original structure. The DNA sequences corresponding to the artificial star sequences that were used to silence the desired target genes are shown in Table 7.

TABLE 7

| amiRNA Star Sequences | | | |
|---|---|---|---|
| amiRNA precursor | GENE ID | amiRNA Sequence | SEQ ID NO |
| Nv-MCS Frg1-Star | inv1c.pk005.h23.f | tggcgttggactaggtacttt | 313 |
| Nv-MCS Frg2-Star | inv1c.pk005.h23.f | gggtggtcagtatttgtaatt | 314 |
| Nv-MMitpro2-Star | inv1c.pk004.e6.f:fis | gggtggaaataattagtaggt | 315 |
| Nv-MitprotCD3-Star | inv1c.pk004.e6.f:fis | tgggagaagatcaaaggaatt | 316 |
| Nv-Madapmol2-Star | inv1c.pk004.e11.f:fis | aagaattattataatactttt | 317 |
| Nv-MadadapCRK1-Star | inv1c.pk004.e11.f:fis | ttgtgtaagggttgatagtat | 318 |
| Nv-MNH1A-Star | inv1c.pk004.d17.f:fis | atcttgtgttaaatcttcgtt | 319 |
| Nv-MNH1B-Star | inv1c.pk004.d17.f:fis | cagtttttttttgcttttgttt | 320 |

The soybean genomic miRNA precursor gene, miR159, was converted to amiRNA precursors by DNA synthesis (Genscript; Piscataway, N.J.). DNA fragments were synthesized with flanking AvrII and HpaI sites and were cloned by restriction enzyme digestion followed by DNA ligation downstream of the GmUbiquitin promoter-5'UTR-Intron1 fragment in the UBQ-Kozack OXOXalt7 vector. LR recombination reaction between this intermediate and the vector QC479i produced the eight final plant expression constructs given in Table 8.

TABLE 8

| amiRNA Precursors and Expression Constructs | | | | | | |
|---|---|---|---|---|---|---|
| GENE ID | amiRNA precursor length | amiRNA precursor SEQ ID NO | Target Sequence | Target Sequence SEQ ID NO | Expression Construct | Construct SEQ ID NO (with promoter) |
| inv1c.pk005.h23.f | 976 bp | 321 | tggcgttggacatggtactta | 337 | PHP44230 | 329 |
| inv1c.pk005.h23.f | 977 bp | 322 | gggtggtcagttattgtaata | 338 | PHP44231 | 330 |

TABLE 8-continued amiRNA Precursors and Expression Constructs

| GENE ID | amiRNA precursor length | amiRNA precursor SEQ ID NO | Target Sequence | Target Sequence SEQ ID NO | Expression Construct | Construct SEQ ID NO (with promoter) |
|---|---|---|---|---|---|---|
| inv1c.pk004.e6.f:fis | 966 bp | 323 | gggtggaaatatgtagtagga | 339 | PHP44770 | 331 |
| inv1c.pk004.e6.f:fis | 966 bp | 324 | tgggagaagatagaaggaata | 340 | PHP44771 | 332 |
| inv1c.pk004.e11.f:fis | 966 bp | 325 | aagaattattaatatacttta | 341 | PHP44772 | 333 |
| inv1c.pk004.e11.f:fis | 966 bp | 326 | ttgtgtaagggaagatagtaa | 342 | PHP44773 | 334 |
| inv1c.pk004.d17.f:fis | 966 bp | 327 | atcttgtgttatctcttcgta | 343 | PHP44789 | 335 |
| inv1c.pk004.d17.f:fis | 966 bp | 328 | cagtttttttttgttttgtta | 344 | PHP44790 | 336 |

The SEQ ID NOS for the various target genes advanced for further evaluation in in planta assays are summarized in Table 9.

TABLE 9

| Clone | Target SEQ ID NO | Fragments of Target Sequences SEQ ID NO | Silencing Constructs for Target Sequence SEQ ID NO | Sequences Encoding Silencing Elements for Target Sequence SEQ ID NO |
|---|---|---|---|---|
| inv1c.pk004.d17.f:fis | 304 | 14, 343, 344 | 335 (amiRNA precursor sequence with promoter)<br>336 (amiRNA precursor sequence with promoter) | 311 (miRNA)<br>312 (miRNA)<br>327 (miRNA precursor sequence)<br>328 (miRNA precursor sequence) |
| inv1c.pk004.e6.f:fis | 278 | 17, 284, 339, 340 | 293 (hairpin RNA construct without promoter)<br>331(amiRNA precursor sequence with promoter)<br>332 (amiRNA precursor sequence with promoter) | 284 (hairpin RNA)<br>307 (miRNA)<br>308 (miRNA)<br>323 (miRNA precursor sequence)<br>324 (miRNA precursor sequence) |
| inv1c.pk004.e11.f:fis | 303 | 18, 341, 342 | 333 (amiRNA precursor sequence with promoter)<br>334 (amiRNA precursor sequence with promoter) | 309 (miRNA)<br>310 (miRNA)<br>325 (miRNA precursor sequence)<br>326 (miRNA precursor sequence) |
| inv1c.pk004.h20.f:fis | 279 | 30, 285, 286, 287 | 294 (hairpin RNA construct without promoter)<br>295 (hairpin RNA construct without promoter)<br>296 (hairpin RNA construct without promoter) | 285 (hairpin RNA)<br>286 (hairpin RNA)<br>287 (hairpin RNA) |
| inv1c.pk004.i1.f:fis | 280 | 34, 288, 289 | 297 (hairpin RNA construct without promoter)<br>298 (hairpin RNA construct without promoter) | 288 (hairpin RNA)<br>289 (hairpin RNA) |
| inv1c.pk005.h23.f | 302 | 263, 337, 338 | 329 (amiRNA precursor sequence with promoter)<br>330 (amiRNA precursor sequence with promoter) | 264 (sense siRNA, RNA sequence)<br>265 (anti-sense siRNA, RNA sequence)<br>305 (miRNA)<br>306 (miRNA)<br>321 (miRNA precursor sequence)<br>322 (miRNA precursor sequence) |
| inv1c.pk008.m9.f:fis | 281 | 290 | 299 (hairpin RNA construct without promoter) | 290 (hairpin RNA) |
| inv1c.pk010.g13.f:fis | 283 | 292 | 301 (hairpin RNA construct without promoter) | 292 (hairpin RNA) |
| inv1c.pk011.f6.f:fis | 282 | 291 | 300 (hairpin RNA construct without promoter) | 291 (hairpin RNA) |

Example 9

Transformation of Somatic Soybean Embryo Cultures

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 hr day/night photoperiod at light intensity of 60-85 μE/m2/s. Cultures were sub-cultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids described in Example 8 by the method of particle gun bombardment (Klein et al., *Nature,* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time secondary embryos were cut and placed into SB 196 liquid media for 7 days.

Preparation of DNA for Bombardment:

Either an intact plasmid or a DNA plasmid fragment containing the genes of interest and the selectable marker gene may be used for bombardment. In the present example, pDNAs were isolated from bacterial transformants using a Qiagen mini-prep kit. DNA concentrations were determined by UV absorbance. Each silencing construct and hygromycin selectable marker plasmid (PHP18956) were combined in a 9:1 weight ratio to give a 1 ug/ul DNA solution.

A 50 μL, aliquot of sterile distilled water containing 1 mg of gold particles was added to 5 μL, of a 1 μg/μL DNA solution (intact silencing and selectable marker plasmids as described above), 50 μL, 2.5M $CaCl_2$ and 20 μL, of 0.1 M spermidine. The mixture was pulsed 5 times on level 4 of a vortex shaker and spun for 5 sec in a bench microfuge. After a wash with 150 μL, of 100% ethanol, the pellet was suspended by sonication in 85 ul of 100% ethanol. Five μL, of DNA suspension was dispensed to each flying disk of the Biolistic PDS1000/HE instrument disk. Each 5 μL, aliquot contained approximately 0.058 mg gold particles per bombardment (i.e., per disk).

Tissue Preparation and Bombardment with DNA:

Approximately 100-150 mg of 7 day old embryonic suspension cultures were placed in an empty, sterile 60×15 mm petri dish and the dish was placed inside of an empty 150×25 mm Petri dish. Tissue was bombarded 1 shot per plate with membrane rupture pressure set at 650 PSI and the chamber was evacuated to a vacuum of 27-28 inches of mercury. Tissue was placed approximately 2.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six to eight days post-bombardment, the SB196 is exchanged with fresh SB196 containing 30 mg/L hygromycin. The selection media was refreshed bi-weekly. Four to six weeks post-selection, green, transformed tissue was observed growing from untransformed, necrotic embryogenic clusters. Isolated, green tissue was removed and inoculated into multi-well plates to generate new, clonally propagated, transformed embryogenic suspension cultures.

Embryo Maturation:

Transformed embryogenic clusters were cultured for 1-3 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 μE/m$^2$s. Embryo clusters were then removed to SB228 (SHaM) liquid media, 35 ml in 250 ml Erlenmeyer flask, for 2-3 weeks. Tissue cultured in SB228 was maintained on a rotary shaker, 130 rpm, 26° C. with cool white fluorescent lights on 16:8 hr day/night photoperiod at light intensity of 60-85 μE/m2/s. After this time, embryos were harvested and used in stinkbug feeding assays.

Media Recipes:

| SB 196 - FN Lite Liquid Proliferation Medium, pH 5.8 (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium, pH5.7 (per liter)

1 package MS salts (Gibco/BRL—Cat. No. 11117-066)
1 mL B5 vitamins 1000× stock
31.5 g glucose
2 mL 2,4-D (20 mg/L final concentration)
8 g TC agar SB199 Solid Medium (per liter)

1 package MS salts (Gibco/BRL—Cat. No. 11117-066)
1 mL B5 vitamins 1000× stock
30 g Sucrose
4 ml 2,4-D (40 mg/L final concentration)
pH 7.0
2 gm Gelrite SB 71-4 Solid Medium (per Liter)

1 bottle Gamborg's B5 salts w/sucrose (Gibco/BRL—Cat. No. 21153-036)
pH 5.7
5 g TC agar 2,4-D Stock Obtain premade from Phytotech Cat. No. D 295—concentration 1 mg/mL B5 Vitamins Stock (per 100 mL)

Store aliquots at −20° C.
10 g myo-inositol
100 mg nicotinic acid
100 mg pyridoxine HCl
1 g thiamine If the solution does not dissolve quickly enough, apply a low level of heat via the hot stir plate.

| SB 228 - Soybean Histodifferentiation & Maturation (SHaM) (per liter) | |
|---|---|
| DDI H2O | 600 ml |
| FN-Lite Macro Salts for SHaM 10X | 100 ml |
| MS Micro Salts 1000x | 1 ml |
| MS FeEDTA 100x | 10 ml |
| CaCl 100x | 6.82 ml |
| B5 Vitamins 1000x | 1 ml |
| L-Methionine | 0.149 g |
| Sucrose | 30 g |
| Sorbitol | 30 g |

Adjust volume to 900 ml
pH 5.8
Autoclave
Add to cooled media (≤30 C):
*Glutamine (Final conc. 30 mM) 4% 110 ml
*Note: Final volume will be 1010 ml after glutamine addition.

FN-lite Macro for SHAM 10×—Stock #1 (per Liter)

| | |
|---|---|
| $(NH_4)2SO_4$ (Ammonium Sulfate) | 4.63 g |
| $KNO_3$ (Potassium Nitrate) | 28.3 g |
| $MgSO_4$*$7H_20$ (Magnesium Sulfate Heptahydrate) | 3.7 g |
| $KH_2PO_4$ (Potassium Phosphate, Monobasic) | 1.85 g |

Bring to volume
Autoclave

MS Micro 1000×—Stock #2 (per 1 Liter)

| | |
|---|---|
| $H_3BO_3$ (Boric Acid) | 6.2 g |
| $MnSO_4$*$H_2O$ (Manganese Sulfate Monohydrate) | 16.9 g |
| ZnSO4*7H20 (Zinc Sulfate Heptahydrate) | 8.6 g |
| $Na_2MoO_4$*2H20 (Sodium Molybdate Dihydrate) | 0.25 g |
| $CuSO_4$*$5H_20$ (Copper Sulfate Pentahydrate) | 0.025 g |
| $CoCl_2$*$6H_20$ (Cobalt Chloride Hexahydrate) | 0.025 g |
| KI (Potassium Iodide) | 0.8300 g |

Bring to volume
Autoclave

FeEDTA 100×—Stock #3 (per Liter)

| | |
|---|---|
| $Na_2EDTA$* (Sodium EDTA) | 3.73 g |
| $FeSO_4$*$7H_20$ (Iron Sulfate Heptahydrate) | 2.78 g |

*EDTA must be completely dissolved before adding iron
Bring to Volume

Solution is photosensitive. Bottle(s) should be wrapped in foil to omit light.

Autoclave

Ca 100×—Stock #4 (per Liter)

| | |
|---|---|
| $CaCl_2$*$2H_20$ (Calcium Chloride Dihydrate) | 44 g |

Bring to Volume
Autoclave

B5 Vitamin 1000×—Stock #5 (per Liter)

| | |
|---|---|
| Thiamine*HCl | 10 g |
| Nicotinic Acid | 1 g |
| Pyridoxine*HCl | 1 g |
| Myo-Inositol | 100 g |

Bring to Volume
Store frozen

4% Glutamine—Stock #6 (per Liter)

| | |
|---|---|
| DDI water heated to 30° C. | 900 ml |
| L-Glutamine | 40 g |

Gradually add while stirring and applying low heat.
Do not exceed 35° C.
Bring to Volume
Filter Sterilize
Store frozen*
*Note:
Warm thawed stock in 31° C. bath to fully dissolve crystals It is recognized that the experiments set forth in example 9 can be employed with silencing elements operably linked to a seed-preferred promoter, such as, for example, those provided by the b-conglycinin-alpha (Genbank accession GU723691), Kunitz trypsin inhibitor 3 (AF233296), or the glycinin-1 (AB353075.1) genes.

Example 10

Assay of Transgenic Soybean Embryos for Efficacy Against Southern Green Stinkbug Cultures of SHaM maturated embryos, as described in Example 9, were harvested by filtration and used in feeding bioassays with $2^{nd}$ instar southern green stinkbugs. A typical soy embryo transformation experiment yielded 20 to 30 independent events that were each evaluated in 4 replicate assays. Each assay was set up in a 35 mm petri dish that contained a moistened Whatman filter disc and a H2O soaked cotton pellet along with 450-500 mg of soy embryo tissue. Embryo samples were infested with 5-$2^{nd}$ instar SGSBs, and the petri plate was covered and incubated at 27 C, 65% RH for 4 days. At this time, the sample was replenished with fresh tissue and the incubation was continued for 4 additional days at which time, the assays were scored for insect stunting and mortality.

FIGS. 1 and 2 show the results of insect feeding assays performed using embryo tissue transformed with the silencing construct DNAs listed in Tables 5 and 8. Each symbol corresponds to insect mortality scores averaged over the 4 replicate assays for each event. Controls correspond to feeding assays conducted using non-transgenic soybean embryo tissue. For all of the constructs, several transgenic events could be found which gave insect mortality scores greater than the controls. For some constructs, more than 50% of the events produced insect mortality at a rate significantly greater than controls. Variation in apparent efficacy from event to event is to be expected due to variation in construct expression with random integration of the construct DNA in the soybean genome.

Example 11

Assay of Transgenic Soybean Plants for Efficacy Against Southern Green Stinkbug

Silencing constructs can be stably expressed in insect feeding tissue for efficacy testing of transgenic plants against southern green stinkbug. The DNA constructs described in Example 8 can be used for this purpose. These consist of trait gene hairpin or miRNA gene cassettes both of which are constitutively regulated by a soybean ubiquitin promoter-5'UTR-Intron1 fragment. Similar constructs can be built using other constitutive promoters as provided for example by soybean elongation factor 1 alpha (ACUP01009998) or *arabidopsis* ubiquitin (L05399.1) genes. Alternatively, tissue specific expression and in some embodiments seed-preferred promoters can be produced by the use of seed storage protein promoters including those provided by the beta-conglycinin-alpha (Genbank accession GU723691), Kunitz trypsin inhibitor 3 (AF233296), or the glycinin-1 (AB353075.1) genes. To produce seed specific hairpin constructs (i.e. long dsRNA constructs and miRNA constructs), entry clones, generated as described in Example 8 above, are combined in an LR clonase reaction with a variant of the destination vector, pKB499, modified to contain a seed storage protein promoter in place of the Gm-Ubiquitin promoter. This first LR reaction generates the promoter-hairpin-terminator cassette. The final plant expression construct is produced by a second LR reaction in which the entire hairpin cassette is moved into a vector (PHP25224) which provides a plant selectable marker gene (herbicide resistant acetolactate synthase) for stable transformation experiments. For assembly of tissue specific miRNA constructs, the procedure outlined in Example 8 would be followed with final cloning of the artificial miR159 segment into a suitable plant expression vector that provides regulatory sequences of any one of the above seed storage protein promoters.

For biolistic transformation of soybean embryos as described in Example 5, a single DNA fragment containing both the trait gene and the plant selectable marker gene is prepared by restriction enzyme digestion followed by gel purification of restricted pDNA. In the case of both constitutive and tissue specific silencing constructs, 10 μg of plasmid DNA is used in 0.15 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 3 hrs. The resulting DNA fragments are separated by gel electrophoresis on 1% agarose gel and the DNA fragment containing the trait gene-selectable marker gene cassettes are cut from the agarose gel. DNA is purified from the agarose using Qiagen's Quick Spin extraction method following the manufacturer's suggested protocol. Gold particles are coated with purified DNA fragments and used for biolistic introduction of DNA into soybean embryo cultures using the procedure outlined in Example 5.

First generation transgenic plants can be assayed for insecticidal activity in individual plant cages. When the plant has started to produce green pods approximately 1-2 inches in length, plants are removed to individual bug tent cages (BioQuip, CA). The cage is infested with 50 newly emerged second instar southern green stinkbugs (*Nezara viridula*). The nymphs are allowed to feed for 1 week at which time a count of surviving insects is performed. Counts are facilitated by using an aspirating device with removable vials and caps to collect insects and a hand held counting device to count each insect as it is aspirated. Counts can later be verified by freezing the sample and counting again under magnification where a measure of growth can also be performed on collected insects. Fully grown insects equivalent to controls are given a score of 0. Insects demonstrating 20-60% stunting are given a score of 1. Insects demonstrating 60-100% stunting (size equivalent to original infested insects) are given a score of 2 and dead insects are scored 3. Selected plants demonstrating high insecticidal activity are recovered from the tents, treated with Marathon insecticide, and returned to growth chambers or greenhouses to complete the reproductive phase and seed production.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A polynucleotide operably linked to a heterologous regulatory sequence comprising a nucleotide sequence selected from the group consisting of:

(a) the nucleic acid sequence comprising any one of SEQ ID NOS: 279, 285, 286, 287, 294, or 295, or a complement thereof;

(b) the nucleotide sequence comprising at least 90% sequence identity to any one of SEQ ID NOS: 279, 285, 286, 287, 30, 294 or 295, or a complement thereof, wherein said polynucleotide encodes a silencing element having insecticidal activity against a Pentatomidae plant pest.

2. The polynucleotide of claim 1, wherein said Pentatomidae plant pest is a *Nezara viridula* plant pest.

3. An expression cassette comprising a polynucleotide of claim 1 operably linked to a seed-preferred promoter.

4. The expression cassette of claim 3, wherein said polynucleotide is expressed as a double stranded RNA.

5. The expression cassette of claim 3, wherein said polynucleotide comprise a silencing element which is expressed as a hairpin RNA.

6. An expression cassette, comprising a silencing element comprising, in the following order, a first segment, a second segment, and a third segment, wherein a) said first segment comprises at least 21 contiguous nucleotides of any one of the target sequences set forth in SEQ ID NOS: 279, 285, 286, 287, or 30; b) said second segment comprises a loop of sufficient length to allow the silencing element to be transcribed as a hairpin RNA; and, c) said third segment comprises at least 21 nucleotides complementary to the first segment.

7. The expression cassette of claim 5, wherein said expression cassette target is a sequence comprising the sequences set forth in any one of SEQ ID NOS: 285, 286, or 287, or a sequence having at least 90% sequence identity to SEQ ID NOS: 285, 286, or 287.

8. The expression cassette of claim 5, wherein said expression cassette comprises any one of SEQ ID NOS: 294 or 295.

9. The expression cassette of claim 3, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the polynucleotide.

10. A host cell comprising the expression cassette of claim 3.

11. A plant cell having stably incorporated into its genome a heterologous polynucleotide comprising a silencing element operably linked to a seed-preferred promoter, wherein said silencing element, when ingested by a Pentatomidae plant pest, reduces the level of expression of any one of the target sequences set forth in SEQ ID NOS: 279, 285, 286, 287, or 30, in said Pentatomidae plant pest and thereby controls the Pentatomidae plant pest, wherein said silencing element comprises the sequences set forth in any one of SEQ ID NOS: 279, 285, 286, 287, or 30, or a complement thereof.

12. The plant cell of claim 11, wherein said silencing element comprises a) a fragment of at least 21 consecutive nucleotides of SEQ ID NOS: 279, 285, 286, 287, or 30, or a complement thereof, wherein said silencing element, when ingested by a Pentatomidae plant pest, reduces the level of a target sequence in said Pentatomidae plant pest and thereby controls the Pentatomidae plant pest.

13. The plant cell of claim 11, wherein the Pentatomidae plant pest is a *Nezara viridula* plant pest.

14. The plant cell of claim 11, wherein said plant cell comprises the expression cassette of claim 9 wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the polynucleotide.

15. The plant cell of claim 11, wherein said silencing element expresses a double stranded RNA.

16. The plant cell of claim 11, wherein said silencing element expresses a hairpin RNA.

17. The plant cell of claim 16, wherein said polynucleotide comprising the silencing element comprises, in the following order, a first segment, a second segment, and a third segment, wherein a) said first segment comprises at least 21 contiguous nucleotides of any one of the target sequences set forth in SEQ ID NOS: 279, 285, 286, 287 or 30; (b) said second segment comprises a loop of sufficient length to allow the silencing element to be transcribed as a hairpin RNA; and, (c) said third segment comprises at least 21 contiguous nucleotides complementary to the first segment.

18. The plant cell of claim 11, wherein said plant cell is from a monocot.

19. The plant cell of claim 18, wherein said monocot is maize, barley, millet, wheat or rice.

20. The plant cell of claim 11, wherein said plant cell is from a dicot.

21. The plant cell of claim 20, wherein said plant is soybean, canola, alfalfa, sunflower, safflower, tobacco, *Arabidopsis*, or cotton.

22. A plant or plant part comprising the plant cell of claim 11.

23. A transgenic seed from the plant of claim 22, wherein said transgenic seed comprises said heterologous polynucleotide comprising said silencing element.

24. A method of controlling a Pentatomidae plant pest comprising feeding to a Pentatomidae plant pest a composition comprising a silencing element, wherein said silencing element comprises a) a fragment of at least 21 consecutive nucleotides of SEQ ID NOS: 279, 285, 286, 287, or 30, or a complement thereof; or, b) the nucleotide sequence comprising at least 90% sequence identity to any one of SEQ ID NOS: 279, 285, 286, 287, 30, 294, 295, or 296, or a complement thereof, wherein said silencing element, when ingested by a Pentatomidae plant pest, reduces the level of a target sequence in said Pentatomidae plant pest and thereby controls the Pentatomidae plant pest.

25. The method of claim 24, wherein said Pentatomidae plant pest comprises a *Nezara* plant pest.

26. A method of controlling a Pentatomidae plant pest comprising feeding to a Pentatomidae plant pest a composition comprising a silencing element, wherein said silencing element, when ingested by said Pentatomidae plant pest, reduces the level of expression of any one of the target Pentatomidae plant pest sequences set forth in SEQ ID NOS: 279, 285, 286, 287, or 30, wherein said silencing element comprises the sequence set forth in any one of SEQ ID NOS: 285, 286, 287 or 30 or a complement thereof, and thereby controls the Pentatomidae plant pest.

27. The method of claim 24, wherein said composition comprises a plant or plant part having stably incorporated into its genome a polynucleotide comprising said silencing element, wherein said silencing element is operably linked to a seed-preferred promoter.

28. A method of controlling a Pentatomidae plant pest comprising feeding to a Pentatomidae plant pest a composition comprising a silencing element, wherein said silencing element, when ingested by said Pentatomidae plant pest, reduces the level of expression of any one of the target Pentatomidae plant pest sequences set forth in SEQ ID NOS: 279, 285, 286, 287, or 30, wherein said silencing element comprises a) a polynucleotide comprising the sense or antisense sequence of the sequence set forth in SEQ ID NOS: 285, 286, 287, or 30 or a complement thereof; or, b) a polynucleotide comprising the sense or antisense sequence of a sequence having at least 95% sequence identity to the sequence set forth in SEQ ID NOS: 285, 286, 287, or 30, or a complement thereof, and thereby controls the Pentatomidae plant pest.

29. The method of claim 24, wherein said silencing element expresses a double stranded RNA.

30. The method of claim 24, wherein said silencing element comprises a hairpin RNA.

31. The method of claim 30, wherein said polynucleotide comprising the silencing element comprises, in the following order, a first segment, a second segment, and a third segment, wherein a) said first segment comprises at least 21 contiguous nucleotides of the target polynucleotide; b) said second segment comprises a loop of sufficient length to allow the silencing element to be transcribed as a hairpin RNA; and, c) said third segment comprises at least 21 contiguous nucleotides complementary to the first segment.

32. The method of claim 27, wherein said silencing element is flanked by a first operably linked convergent promoter at one terminus of the silencing element and a second operably linked convergent promoter at the opposing terminus of the polynucleotide, wherein the first and the second convergent promoters are capable of driving expression of the silencing element.

33. The method of claim 27, wherein said plant is a monocot.

34. The method of claim 33, wherein said monocot is maize, barley, millet, wheat or rice.

35. The method of claim 27, wherein said plant is a dicot.

36. The method of claim 35, wherein said plant is soybean, canola, alfalfa, sunflower, safflower, tobacco, *Arabidopsis*, or cotton.

* * * * *

SEQUENCE LISTING

<160> NUMBER OF SEQ ID NOS: 346

<210> SEQ ID NO 1
<211> LENGTH: 272
<212> TYPE: DNA
<213> ORGANISM: Nezara viridula

<400> SEQUENCE: 1

```
gggtattaat ttttatttgt ttatccataa attagctctt ttaaaccaat tactttgatt     60

ttttcttgat agttatcatg ttagcgactt cattaacatt cactaatcag gaaagacagt    120

ttacgaaatc tgtatctaga ttgaagaaat tccgtatgat ttttaataca ttgaaaaaat    180

atggccatta atcgaattag aaaaacgttt ttctactaca acaataggcg cagactttcc    240

atttcgcttt gggagagggg aggtgaagaa cc                                  272
```

<210> SEQ ID NO 2
<211> LENGTH: 529
<212> TYPE: DNA
<213> ORGANISM: Nezara viridula
<220> FEATURE:
<221> NAME/KEY: misc_feature
<222> LOCATION: 476
<223> OTHER INFORMATION: n = A,T,C or G

<400> SEQUENCE: 2

```
gggtatcaat tatacatata aagtagcatt accttcctat ttacaaagaa aataaataca     60

agttgattca aattattgaa ctaaactatt tctttaatca ttagtaatat gctaaaaaaa    120

ttaacattac ttctgtaacg cattcaaaat ttaaaaaaac aaaagacagg atataacctt    180

tccagtagaa catataaaaa aaactagaga ccatatattt gctcctaatt ctctgatttt    240

aacgattatt tttttgtttt tcaggaaatt ccgtaaattt tgaaaaacac aaatccgtat    300

actttttgag ttattcggaa tttaattgta ccatccctcg taactttttt cctagcttct    360

tttcgttgaa gtatgttata tagataaatt tagaaggagt tgagaaattg attttagcga    420

agtttcattg aaatcggtac attcgtttag acgctacagt ctgtagcaac tcaganttt     480

tttccccgtt attttaaaag taaaaggcga ataataatgt cgatgaagc                529
```

<210> SEQ ID NO 3
<211> LENGTH: 574
<212> TYPE: DNA
<213> ORGANISM: Nezara viridula

<400> SEQUENCE: 3

```
ggggaaggag ctcaagattt accctgctct gcgagtttac tgagtggaag tttatcttct     60

tttccaagtt attcatcgac ttctagaaga tctctatcac tcaaacaagg gcgtaagtcc    120

actctatctc ccaaagacat taactcatca tcggtagatc agacggcaga agcacagtcc    180

actggaaaga gaactactca atccagtgat attgttgaaa atgttaaggc taactcattt    240

tcatcttctc gtaaaggaag acgatctctt agtataccaa atggtagttc ctttgaaaaa    300

aatcatttga tgcagtcatc agaatcaggt tccagtgatt tattgaatat taccaatgaa    360

aagcacaata gaagtgttga tacaaatcat ttctcatctc ccttaaatga cactttatct    420

aggagtaagt tcgttgattg taatattagt cagaaaggct taaatggttc atcttcagat    480

gtgtcagttt tttctctggg ttcttttaat tcttcttatc ataaaagtaa aagtgatggt    540

gatagtttat ctttatcaca agctactgat gtaa                                574
```

<210> SEQ ID NO 4
<211> LENGTH: 652
<212> TYPE: DNA
<213> ORGANISM: Nezara viridula

<400> SEQUENCE: 4

```
ggggattgga caagaggttt ctcgtttctc aatatgaaga tctttttct cctttttgtt     60

gtggctgtca gccatgcgct tcctcacgat gaatgggaat tgtttaagat atcgcatggg    120

aagaagtaca aaacattagc agaagaacaa caccgaatga atattttcta tgacaacaag    180

cagttcatcg aaaatcataa taaaaatttt gaacaaggcc cggtctcttt cactctggaa    240

atgaaccgtt ttggagattt gatgaaccac gaattccgaa caatgatgaa cagatacaac    300

agtacaaaag cagctagaac tagacaagat tcatcaactt atatcagatc aaccgatgaa    360

gaagttcccg aatcttttga ctggaggcag gaaggagcgg tcacccctgt caaagatcaa    420

gcacactgtg gctcatgctg ggcttttagt actactggag ctcttgaagg acaacacttc    480

aggaagaccg ggaagtggt ttctctcagc gaacagaact tggtcgactg ttccagcatg    540

tacggcaaca atgggtgtca aggaggactc atggttgacg ctttcaagta cattgctgaa    600

aatggcggca tcgacactga agattcttat ccttatgaag gaagggacgg ca            652
```

<210> SEQ ID NO 5
<211> LENGTH: 75
<212> TYPE: DNA
<213> ORGANISM: Nezara viridula

<400> SEQUENCE: 5

```
gggggtgtaa taagacttcc tgaaagtccg ttttatcatt gaccttaata aatttaattt     60

aatcactgtt ttctg                                                      75
```

<210> SEQ ID NO 6
<211> LENGTH: 643
<212> TYPE: DNA
<213> ORGANISM: Nezara viridula

<400> SEQUENCE: 6

```
ggggagtctg ccagcgactt cttccccgcc atataccagc ggtacctact tgtacatagc     60

agtacataag tacataagta gaggcacctc ttgatgtaca gacactccat tcctagcaca    120

gaaagaagac ctcatcgctg aactgaaaat gtcgaaagat atttcgggca tcaagaagct    180

caaagtggag aggaccaagc aggaggagaa ggagtactgc atgtttacaa tacaatgtta    240

tcataattca taatttttat ataagtttga taagtaaaga attgtaattt tttttaaaac    300

aaaattgtgc ttaaaattta taaaattcag taatttaaac tgtataaagc tgatatgatt    360

taaagaaatc ttgggacctg aatcgacaaa tttctagcca tttaatgcca ataacttaaa    420

taatcttatc gaatgatatg ttattataga ttttttttta aatttatgat tatgaagtta    480

ccctccattc aaactaacat tagattataa acaaaatatt ttacagtttt gtaataaaga    540

tcttgaacaa taaaccataa atctttattt gtagaaaata aaaagagctt cactaacttt    600

tattgtaagc aaaagaaaat tataacaaag aacatgttac att                      643
```

<210> SEQ ID NO 7
<211> LENGTH: 542
<212> TYPE: DNA
<213> ORGANISM: Nezara viridula

<400> SEQUENCE: 7

```
ggggacagtt cttcgtccgt ttaggttaac actcgccatg aagatcggtt tgtgtgcgta     60

cagtgggtac aaaatttacc ctggacatgg gaagaccatg gtcaaagctg atgggaagac    120

ctttacattt ttaaactcaa aatgtgaagc ttcccattta atgaggagaa atcctcgtaa    180

agttacttgg accgttttat acagacggaa gcataagaaa ggtcaggagg aagaacagag    240

taagaaaaga actagaagga cccagaagtt tcagagggct attgttggtg catccctttc    300

agatatcatg gccaaaagaa acatgaaacc tgaagttagg aaagcccaga gagaacaggc    360

aattagggct gccaaggagc agaagagggc gaccaaggct gccaaaaaaa cctgaaaaag    420

cagctcccaa ggttaaacag ccttcaaaac agaaggccac caaggttcaa cagaaatctg    480

ctccaagagt tggaggaaag cgataatttt tttttgtatt ttaaataaat acgttttatt    540

at                                                                   542
```

```
<210> SEQ ID NO 8
<211> LENGTH: 676
<212> TYPE: DNA
<213> ORGANISM: Nezara viridula

<400> SEQUENCE: 8

gggaagcagt ggtatcaacg cagagtggcc attacggccg ggaagcagtg gtatcaacgc     60

agagtggcca ttacggccgg ggaatattaa ttttatgtaa actttaactc atatttattc    120

tcagaaaatt ttgtattcca gtcaataaat aaacaactca tttcaacaat tgacatgaga    180

atgagaacaa ctgattatcg aaacgttgct aaaatataat tctatattta tttaatgatc    240

atcaatatac ttgaaacatc attaagaata tattaaacaa ttatatttat tattgttagt    300

tataacaaat ctttgtatcc aaaattaaaa gaaattagtt gacccgagtg aataatacgt    360

atagtgtatt gattagtgaa agaaataaga taatgctatg tattatgtga cggagaaaaa    420

attttctttt tctccatcaa taacaaaatg cattcacaag tttacaaatt acaataggat    480

gcatctttgc gaataattgt gtttttatat gaatagttgt tttgtttttt tttcagtgtc    540

atggataaga tccgaatttt catgcaaatg catatttttt tttttcaaaa acatgagtcg    600

atatctttac gaaacaagtc attctattat tattttattt tttttttttt agcatttatt    660

tataacatta ctattg                                                    676
```

```
<210> SEQ ID NO 9
<211> LENGTH: 606
<212> TYPE: DNA
<213> ORGANISM: Nezara viridula

<400> SEQUENCE: 9

gggggtcagt ctaacgttgg acgccatgaa gagatcttcg gaagtttgct tactcagccc     60

actggattcc ggtctatgta tgagactggt aagctcagct gatgattcta cggcattcaa    120

gtcttccggt gtcttcaaga cattggacct tatcctcaaa gaagacacag atggaactat    180

cgaaaaggct cgaggaatct acaatttcaa agtcaaaaat aaagaaggaa aggaagctat    240

atggactgta aacgcttcga ctggtaaagg ttctgttaca ttcaatggaa aggaaaagcc    300

agatgtaaca tttattatta acgatgaaga tgtcattgat ctgttgtctg gtaaactcaa    360

tccacagaaa gcctactttc agggaaaaat aaaaatcaca gggaacatgg gtatggctat    420

gaaaatcaca ggattgttga aaagagcagg tagtaaaatg gataacctca aagctaagtt    480

gtaaacagaa cagttaagac tgaatatgtg tgaaacaaag taagttaata gtgaatggca    540

tcatatgaat ataaatatat gtatatataa ttgtaatgtt ttgttgataa ttatatttag    600
```

ttaacc 606

<210> SEQ ID NO 10
<211> LENGTH: 656
<212> TYPE: DNA
<213> ORGANISM: Nezara viridula

<400> SEQUENCE: 10
gggggtcagt gcctcagctg caatcatgtc ctcagttcta tacttggtac tcctcttcgg 60
ggcagccgtg tctgccaagc acgtcctccc ttcttacgtg aagacttgct caaggaatga 120
ccccaacctg agtgagtgcg cactgaagag gggcaaggag atcataccca agatcattaa 180
aggagaccca agtataagac ttccagtact ggacccgatg atgctggaca aagttggtat 240
cagtaccact ggtcgcgcca atgggggagg actccaactc acttgctaca aatgtatcgt 300
ctacgggctc tcaaacgcag tactccagga catcaaaatt gacttggaca agaagcacat 360
cgccttgaag atcttcgttc cacaattatc tgtcgcaggc aaatatgatg tcaatggcaa 420
gctattgctt ttcccaatca ccggcaatgg acaggctaac atcactctgc ttgatttgaa 480
agctgaggcc gccctcgact ggaagcttat caagaggaaa ggaagcgaat acgctcacat 540
ctcaagggac agggtagact tcacagcatc aaggcttaag ctctccctaa ctggcctctt 600
cggtggagac aaagcactca gtgacaacat gaaccagatc ctcaacgata actgga 656

<210> SEQ ID NO 11
<211> LENGTH: 688
<212> TYPE: DNA
<213> ORGANISM: Nezara viridula

<400> SEQUENCE: 11
ggggcatcag aaccagccat gttcacagct tggtctcttt gcgccatcct cttcgccgct 60
gtcttcagcg caggagctgc acccttcgat gacgatgagg atatcctagt cgacaaggtg 120
aaggacatca ttacccacat caacaacttc atcgaagatc ataacttaga gcacctcgcc 180
cttcccaaca tcgggctgct tccgatcgac cctctcaagc tgagacaagg acggcttggc 240
aagttctcca ccatcgaatt acaggatgtc accttcatca atcagactac gatgactgat 300
gggtccgtcc tgttcaactt cgacctctta cttgggctga aggagttccg gttcgaatac 360
gactttaccc tttatgctcc tttcttattc aaccataatg ggcatttcac cctctcgcct 420
ctacgaaact ccattcaggt atccggtaaa gttgccatca aggataagac atgcgacgcc 480
agcctcggca acgtcagagt tgccgagtac ggccacttca agatcgacct ccagccgaac 540
aacatgcctt atgccacgca gataaccgaa gacctcatga atttcgttac ccctctggtc 600
ttacctatta caaacaaagt catggaaata gcagcttatt taccacctgt aaacagggtg 660
ttgtcaggac tggtttgcaa agtcatag 688

<210> SEQ ID NO 12
<211> LENGTH: 681
<212> TYPE: DNA
<213> ORGANISM: Nezara viridula

<400> SEQUENCE: 12
gggctaatca atttataaga cttattagct attgattccc agtttcttga atttcctttt 60
tctataattt ttgtccatat atcacttggc aaaaaattct cttaattttt tttctgcaga 120
ttgctgttga agtgctcatc aaagaatgtt actttcaatc tttctgtagc attttccatt 180

```
cattgtttcc agagcccttt ggcctcctgt ttttatgtaa tgaactgttc actgcattaa    240

atattcatta taactcctac cctttcccat tttcatttag aagtttaata ttttcaacat    300

tcaataacac atatctaaca ccattagtta agtagtccgt acagttccat tatgtcatta    360

tatagcttcc tattgacacc catcactcac ttagttttat ttaattctgc tatagtagtt    420

aggtaactat caaaattatc ttgtactttt ttttcttttg gtattgctga aaaatctatt    480

acgacttcac atttctccaa atcttctgtc atcttatctc tgtgtgttta aatcttaaac    540

attgtttaca agaaacattg tttccaagat taatatattg tttaacgaaa ggattattgg    600

cccaaatgat aatgtacttc ctataggtat tgtggttgac aggttgcctt caccatgact    660

tcgagctttt atacccatct c                                                681


<210> SEQ ID NO 13
<211> LENGTH: 674
<212> TYPE: DNA
<213> ORGANISM: Nezara viridula

<400> SEQUENCE: 13

ggggagctga taaaaaataa tcgttcaagt caactcacca acttgcagca aaatgccctc     60

aaatcaaatt ttgagtattg ttagaaatta tgcttctgct gccgctgcaa aatctattaa    120

accacctgtt caagtatttg gattagaagg tcgttatgcc acagcacttt attctgctgc    180

agtgaaattg aaacaactag atgttgtaga aaaggattta aaaaatatac agagtacatt    240

gaaaaatgat accaaacttc gaacttttat tgaaaatcca accattaaga ggaatctgaa    300

gatcgatgct ttcaaggatg tgtcaaataa aattaagttg agtgcaccat ccacaaacct    360

tcttggtctt ttagctgaga atggtaggct caatagactt gaccaagttt tgaatgcttt    420

ttctacaatt atggctggcc acagaggtga tcttcgatgt gaggttacga ctgcaaagcc    480

attggatgag gaaacaaaaa aacaactaga gactgtattg aaagcatttg ctaaaaaggg    540

tgaaaatatt atttcggagc tgaaggttga accagctatc attggtggaa tgatcgtcag    600

tattggtgat aactatgttg acatgagtgt ttctagcaag attaagaagt atacagatat    660

catcacagag gctg                                                       674


<210> SEQ ID NO 14
<211> LENGTH: 687
<212> TYPE: DNA
<213> ORGANISM: Nezara viridula

<400> SEQUENCE: 14

actcaaaatg atagcacttt gtgatttatt ctatatgtca tccaatcttt aatttactgg     60

acgattgcta aaataagttt cagaaatatt tgtctgtaat aacattaatt gctcaattat    120

agaaataaag ctactaatta gcctataata tctaacatat atctaaaaaa ttagatatat    180

gttgaaccct aagtattgta aacatcagca tgttatacaa taaattaata acagaaaaca    240

ttcttacttc taaacagaat gaaaatatag agtacttgtg atttagccgg tcgccttcgg    300

acctaccttc ttatcttgtg ttatctcttc gtatcgctca tctctgctta gttacttgtg    360

cgttcttctt gttattcaat tattttcagt tttttttgt tttgttattt tttatttaaa     420

atggttacaa taacacttta ggaattactg tcttcggaag aagactatat tatatattag    480

acaggtcaac taaaaaaatt ggagggtcta aaaaagttgt tgaaatagac ggaagtcttt    540

tttctaaacg aaaaaatcat gtagggagag tgctctcgga ataatggatg tttggcagag    600

tttgtcgaga aacagatgag tgtttcattg taaaaaataaa agaaacgcaa caattctatt    660
```

```
tactaattga taatatctct cttctat                                       687


<210> SEQ ID NO 15
<211> LENGTH: 494
<212> TYPE: DNA
<213> ORGANISM: Nezara viridula

<400> SEQUENCE: 15

ggggttaatg ttataatcta atatttgaat tttatggagt aataaatggt actgtagaaa    60

atgaattcta aatttttaag ataaaataat agactgtcga atagtacttc ttaaccttaa   120

catttaaaat ccaagtatat tataacagta atataggtaa tatatttgga atcaaataca   180

agttttataa tattaactca ttttattata aatgaattaa tattagaaaa ataaataaat   240

cctattattt ctaaaaggag ttttttttt atcggtacgt cataacttcg tcaattcctc   300

atcaaatcca acgattgacc gctcattttg aagatattct gctcctacac atgtgaaaaa   360

tagtccaatc tccccgaaat ttctggaaaa aaagttatgg aggaaaagaa actttatttg   420

cgaataactc aaaaagtatg catttttgtt tctggattgt acccacgata attacaaaga   480

ttactaaatt acct                                                     494


<210> SEQ ID NO 16
<211> LENGTH: 100
<212> TYPE: DNA
<213> ORGANISM: Nezara viridula

<400> SEQUENCE: 16

ggggtcagag ttgggtagag aaactctaaa acaaatagaa aatactaaaa ggcgtttaca    60

attaatgaaa atagcagaaa agaaagtgta agcagaaacc                         100


<210> SEQ ID NO 17
<211> LENGTH: 693
<212> TYPE: DNA
<213> ORGANISM: Nezara viridula

<400> SEQUENCE: 17

gggtggaaat atgtagtagg aacaaaagtc agttaagtag tatgctctct gcaatcttgg    60

actataccag caataaaaac tttatcatta gagataaaaa agatatatca ttttttttcta   120

aagctatgga agtttgtagt aaactcaaag ataaggatct tctctacagg cttcatgaat   180

tattgttgac cggaaacaat tataatttga tcggagattc atttagtgaa tcggtgtatt   240

accgttattt ttttttattt gcttactgat actgaagaac ttagtaaagt aatggaattc   300

tatgatgacc ttgtaccaaa cgtttatgtt ccagagccat cagtgaccaa tgctatattg   360

aaagctgttt gtaacaacat ggcatgggac cttcttccca agctttggcc agacatacta   420

ttgtttgagc agtatgaagt ttccggtgtc ctggaaaata ttttagatat tgcatctcaa   480

aatgaaggca agaatttgat ggaagggatg tctaaaattg catggtctgc atgggagaag   540

atagaaggaa taaagaggga gcgatccaac tttcaatggt ctgcgagtgc attgggaaac   600

attattctca ttttgttgaa atctggtgaa aaagctaagg cgaatttggt tatgaataaa   660

ttaattcaac taggaagttc tgccatgaat gaa                                693


<210> SEQ ID NO 18
<211> LENGTH: 654
<212> TYPE: DNA
<213> ORGANISM: Nezara viridula
```

<400> SEQUENCE: 18

```
ggggaggtta tgtgactgtg ttacatcgag tttgatattg ttttcattgt gaagtgttga     60

ttagttctgt attacttcga agtttaaaga attattaata tactttagaa atgttgaatt    120

ttggttataa tgctagaaga tatatttatg ttttcatatt tactatgcct cttacttagt    180

actgatgtta cataggaaaa tgagagttaa aaaatatttg cctgatgtgt acatttgtgg    240

aagaaaattt aattctagaa aatggctgct ctgtttgacc caaatgacag aagcaggtaa    300

gttcatgaaa ttggtatttt ggtcaaatgt caaggcaaga tgccactgat cttttaatgg    360

gagaaaagga gggtggcgta tttcttgtcc gtgatagtat ctcaattcat ggtgattatg    420

ttctttgtgt aagggaagat agtaaagtaa gccattatat tatcaacaaa attcagcaga    480

atgatcaaat taagtacaga attggtgatc aaacatttaa tgatttgccc agttagctat    540

ctttctataa attgcactat ttagatacta cacctctaat tcgaccagca ccaaagagag    600

ttgaaaaagt gatagctaaa tttgacttca atggaagtga tcaagatgat ttac          654
```

<210> SEQ ID NO 19
<211> LENGTH: 635
<212> TYPE: DNA
<213> ORGANISM: Nezara viridula

<400> SEQUENCE: 19

```
ggggtttgca cctaatccaa tgtttggatt ctttattatg agagtaccaa tgttgcaaat     60

cagagatcca gaacttattc gacttatact tacaaaggaa ttttcacatt ttcgagacag    120

gatgtttatt aaattaagtg aaaaagatat tctcaatcaa catctgttca atctggaagg    180

cgaaaggtgg agagccttac gtgtgaaact caccccaaca tttacaagtg ggaaaatgaa    240

agctatgttc ccactctttg tcaattgtgc tgaggccttt gaatctttga tcgtgtcaaa    300

aattggtagt gacgtagaca tcaaagaatt agtaggtcga cttacgacag atattatctg    360

cagctgtgct tttggacttg atgctaatac aatcgaagag ccagatcata agctaaggca    420

aatcccagcc caacttacta aaatggggtt tattgataaa gtgataatag caatcatgca    480

agctatgcca caagttgcca gcaaatttaa agccaggttc actcctaaag agcttgagga    540

ctatattgta ggtcttgtag aaaacacatt ggagtataga gaaaagaata atattaaaag    600

aaatgatttc ctagatttat taattgagct gaaga                               635
```

<210> SEQ ID NO 20
<211> LENGTH: 682
<212> TYPE: DNA
<213> ORGANISM: Nezara viridula

<400> SEQUENCE: 20

```
ggggttcctt agcaggtttt cttgagtttt cattaaaaaa aaaaaaaagc actagtaagg     60

aaaacaataa tataaactat atatacattt ataaaactat atactgtcgc tattttgcta    120

atacatctat ttttaattaa caatatatat tttttaaata tttctgcctc tctatcaaag    180

atataacgaa gttttaagtg tctagatggt cagataccaa tttcgattaa ttttatcaat    240

actttttctt acggatgcgc aagtgtattt tcttagatat gctaatattt cagaaactgt    300

cagttcgatt tggcccaaat ttggattaaa gatgggcatt ataaaatagt gggtaaaaaa    360

aaaatcatac aattttttat taattctatc ttaaaattta cttgaaatgg agtattggat    420

atcagaagaa ttcataatcg agaaaatgaa aatacattcc acaagacaaa aaggacataa    480

atactaattt aaggtaatag gttattaatg ttattatgtt tgaaataatg gagcacgcca    540
```

```
tttttctaat tattatcata tacatgtaaa tgtaagaatc agtagaagaa aagaaaaaca    600

tttagatggt caaaaaacac ttggtcatta tcgcttcgaa taacgatttt taaatattta    660

taaaaaaaca tttttttat at                                               682


<210> SEQ ID NO 21
<211> LENGTH: 688
<212> TYPE: DNA
<213> ORGANISM: Nezara viridula
<220> FEATURE:
<221> NAME/KEY: misc_feature
<222> LOCATION: 587, 600
<223> OTHER INFORMATION: n = A,T,C or G

<400> SEQUENCE: 21

ggggccgttg tttctggttc agcatactct actaaatcta agcttaacgc agccgaaagc     60

aaagaaaaca aacaatcgaa agaaacctcc aacaagggat attccaagaa agccactgga    120

tacccagcct atggtgttta tggtggaggc gcttatgccg aatccggcta tgacaagaaa    180

tccaaatcag cttcttccaa caaggctagc cgtaccctaa acaaggaaga ttccacaaaa    240

gtaaccagct caagtgttgt agctccagga gttattgccc cagcagtcgt ttctagttca    300

ggatgctcca ccaaatctaa gcttaacgca gctgaaaaga aagaaaacaa acaatcaaaa    360

gaaacctcca acaaaggata ctcaaagaaa gccactggat acccagtata tggtgtttct    420

ggtggagccg cttatgctga atcaggctat gaccagaaat ccaaatcagc ttcttccaac    480

aaggctagcc gtaccctcaa caaggaagat tccacaaaag ttaccagctc tggtgttgta    540

gctccaggaa ttgttgcacc cgccgtcatt ggtagctcag gatattncaa aaaatctaan    600

gttaacgccg ccgcaagcac agaaaacaaa caatctcaag aatcctctaa caagggatac    660

tcgaaacagg ccactggata tccaggct                                       688


<210> SEQ ID NO 22
<211> LENGTH: 121
<212> TYPE: DNA
<213> ORGANISM: Nezara viridula

<400> SEQUENCE: 22

ggggatacaa aaacaaatgt aataacaaca aaaatacttt tatttgacga caaatatatt     60

aatgaaataa taaaaaaaca ctttgagaag atatgtacat ataaaacatc aaaatgaaat    120

t                                                                    121


<210> SEQ ID NO 23
<211> LENGTH: 678
<212> TYPE: DNA
<213> ORGANISM: Nezara viridula

<400> SEQUENCE: 23

ggggatttct ttgaatttat ctaattatgt ttggccctct agaattttct ccaactgtca     60

aagaaatatc cgatcaatat ggaaaaattg aaagatatga agtcggttgt cttttatgct    120

ccagtacctt taacttccca tctgaaaagg atgtatgttt aggtcacatt tttgaatctc    180

ataaaataat aatagcagat gttcaccaga tagggaattt aaaaaagtat ttagaatttt    240

ggaaacaaca attttcagaa gctcccatta cagaattctg ttcaactatt gttgcagata    300

taaaaaaaga tggtttacct cttaaagaca aagagtactt tttattatca gatgtgcacg    360

ataaggataa atttattcga gaaaaacttc aaacagaatt gcttgaaagt gccttagatc    420
```

```
aacaaaaatt agagagagag gacacaaatt atagtcatgg ttgtctcttt tgtcgtcaga    480

ttatagagcc cacaagatct gaatatttga ttcacctttc aacacagcac aatttacaat    540

tagggaaacc agaaaacctc gtttatgttg atgaactaat tgaaatcttg gaacaaaaaa    600

tggaaaagtt gcaatgcatt ttttgtgaac gaactttcaa agacagaaat gtcctcaaag    660

agcatatgag aaaaaaga                                                  678
```

<210> SEQ ID NO 24
<211> LENGTH: 103
<212> TYPE: DNA
<213> ORGANISM: Nezara viridula

<400> SEQUENCE: 24

```
gggggtcaa cggcgggggg gcggggtggc cgaataggct aaagcgtgag taacagcacc      60

gctagttgcc tggcaaccgg ataacagaga tttgagacga tag                      103
```

<210> SEQ ID NO 25
<211> LENGTH: 613
<212> TYPE: DNA
<213> ORGANISM: Nezara viridula
<220> FEATURE:
<221> NAME/KEY: misc_feature
<222> LOCATION: 489
<223> OTHER INFORMATION: n = A,T,C or G

<400> SEQUENCE: 25

```
agtccaataa gggtgctaca tttttttttt gatcggacaa gggggcttat aaacatcttt     60

agatacctga aaagagtacc atgaaaaaaa aaatgaaaac cactgtctta ttaaacctag    120

acagcagtaa tgtaaagatt gatattcata actggtcttt aaaaagtttg acaacaaaat    180

atgtctattt gtgaaatttt ctaaaggttt ttttcacaaa atcaaagctg gtgaggttgg    240

tccattgtga ttctcaaaat ttataatttt caaatataca acaatttaag aatttttttaa   300

aaaagttaat aaatggatgt attttttcac cctgttaaaa gtttaacgta aatctttatt    360

gttataattt tttttttga ctgatttact atcttaattt tgatgaatca aattataatt     420

ttaattttat atattattgt aaagttgaaa ttgtagaagt tgcctttaaa agaataaaat    480

aatattttnt tccttcttaa cccaaaaaca attgttattt agataattag attatcattc    540

gatatgataa atgaaaaaga ttatttagga aaaaatatgt tacgatattg ttaaactact    600

aaattttaca aat                                                       613
```

<210> SEQ ID NO 26
<211> LENGTH: 682
<212> TYPE: DNA
<213> ORGANISM: Nezara viridula

<400> SEQUENCE: 26

```
gggatgctaa aacatcctgc taatcgttac agaattttaa ttatacgaca tttttaaaat     60

acagtattca cctatgttcg tctaattact ataacaggaa ataaataaat taaatttagt    120

ttttaaaaag tgcagacaat tttagagatt aatacaaaag aaagtttaaa atgaacttag    180

taacggcacg gctgtctttt cggttgatta aaaaactttt ctaacgttct gttcccatct    240

caaatttcca atgatagggt agtacaatta tggttcggaa tttaattaaa gattaattta    300

tttaagaaag taccaattat tttatgtact ttatttgttg acatttttat agtacaatta    360

taaaagaaat cgtctaattt tgaatctaaa ctattcaaag ttatccttat tagtgtccag    420

tttaaaaccc tccctcactt agctaaatat atatttgtta taataagtat gtgtacttat    480
```

```
tttatgaata atgttaatta ataataagtt attaagtttt atatttgaaa atttcatagt    540

ttaaaggttt ttttctccaa aaatcgcata ttcatttagg atttcatcat tttattttaa    600

aaactccgtt tttggaattt acaactgtct gactaaattc cgtaataatt tactaactcc    660

gtacctgaaa ttatactgtt aa                                             682


<210> SEQ ID NO 27
<211> LENGTH: 51
<212> TYPE: DNA
<213> ORGANISM: Nezara viridula

<400> SEQUENCE: 27

ggggtggagg tctgatgcac cccagtgtca tgaagctgtt aatggtaaaa c              51


<210> SEQ ID NO 28
<211> LENGTH: 636
<212> TYPE: DNA
<213> ORGANISM: Nezara viridula

<400> SEQUENCE: 28

ggggagatca gtagcgatgc acatctattc ctttgcgatt gtagttcttt tggcaggctg     60

cggcctcgcc ggtaaatgtg gtagctacgt ccagccggcc gtctaccaaa cgtatggtcc    120

agttgccgct ggtagcagtg gatactcgac cagctctaaa cttaacgccg cagaaagctc    180

agaagccgca caatcccaag aatcctccaa caaaggatac tccaagtatg gttccggata    240

cccaacttac ggtttgtacg gaggcggtgc ttacgccgaa tctggttatg atcagagctc    300

caaatcagct tcatcatcca aagctagccg ttcccttaac aaggaagatt ccgccagtgc    360

ttacaactca ggatttgctg caccaggctt ctatggccca gcagttgttg gaggctcagg    420

ttattctacc agttccaaac ttaatgcagc agaaagctca gaaaactctc aatcccaaga    480

atcatccaac aaaggatact ccaaacaagg ttccggatac ccagtctatg gcctttacgg    540

aggtggtgct tatgctgaat ctggttacga ccagagctcc aaatcagctt catcatccaa    600

agctagccgt tccctgaaca aagaagattc cgccag                              636


<210> SEQ ID NO 29
<211> LENGTH: 364
<212> TYPE: DNA
<213> ORGANISM: Nezara viridula

<400> SEQUENCE: 29

ggggagttca gtttttttcca ccaaaatgaa gctctacatc gccgtcctct gcatcgttct     60

catccaggga gtccatgtta attgccagag cagttacttg gactcggcca tgagtactat    120

caacagtgct taccagcaat accgcagcgg aacactgttg aggaacctcc tacagactgc    180

cagggaatac ctcaactatg ccgttatcag actgaaccag ttgcagaact tcatcagcac    240

cttgcaggtc ccggcattgc cttcgatacc gcagcccaca gtcccaggca ggatttggca    300

acagtgggct ggacgctaat tgtttcatgt acggtcaaat tataataaat tgtttataat    360

catc                                                                 364


<210> SEQ ID NO 30
<211> LENGTH: 683
<212> TYPE: DNA
<213> ORGANISM: Nezara viridula

<400> SEQUENCE: 30
```

```
ggggagtttg aataatttca atctcatcta aaggattatt taatgtgaat gatttgtgtc     60

agtttttact tttaactgcg gcatatagcc tgctgcagtt aatgcgggaa ggtttacctt    120

attatgtctg actgggaaca aagattgctc agcctggaaa aactggacag gtcatcgcca    180

gagctctggc cagagccgat acctggggtg acagaatatg ctgctcgcaa tgctctttct    240

agttcctctg ttccaaagaa cattgaatca ctccagagtc agtttactga ggatgactat    300

aagctgctaa attattacag tactctttct aaagaatctc tgattcaaga attaaagaag    360

cttcatgacc aggcctataa attaggtctt gaagaagcca aggaaatgac tagaggaaga    420

tttttgaaca tactgtctac cagaaaaaag taatggtttg taaatgctgc catgcttctg    480

aatggttcca tcatattctg atccagaaga aggaagttgt agcgaatgga gtaggtataa    540

aagtgagtca ataaggacaa gaagggctaa tttaatgtat ttttccaaat atttttgtaa    600

ttgcagaata gaagatttat gtgaagaaat gaatttaagt tttttgttgtt gtaactgtct    660

gttatagttc cttcagtccc aaa                                            683
```

<210> SEQ ID NO 31
<211> LENGTH: 672
<212> TYPE: DNA
<213> ORGANISM: Nezara viridula

<400> SEQUENCE: 31

```
ggggagcaat agtagaatta tgcgcgtcat atgtgcaact gaatagtgat gctagttagt     60

tttaattgta tatattatga tgtgaagtaa ttatgtagcc cgtaggaacg ataaggactt    120

aattaattaa gtttgggacc tgatatcttc ctaagggatt agtgcattta agaattaaat    180

ggcggctgaa gaaaaatggt attttaccaa ggaacaatta gcaaatactc caagcagaaa    240

atgtggcttc gatgcggata aggaattgtc tagcagacag caagcagcaa atttcattca    300

agatatgggc caacggttac tagttactca gctatgcatt aatactgcga ttgtatatat    360

gcatcgtttc tatatgttcc attcgtttac acggtttcac cgaaatgcga tggctgcagc    420

tgcattattc ctagcagcta aagttgagga acaacccaga aagcttgaac atgttatcaa    480

agtggcccag atttgtcttc acagggagca acctccactt gacatcaagt ccgaggttta    540

tatggagcaa gctcaagaac tcgttgtgaa tgaaaatata cttctccaga cccttggatt    600

tgatgtcgca atagatcacc ctcatacaca tgttgtaaga tgttgtcatc tagtcagagc    660

aagcaaagat ct                                                        672
```

<210> SEQ ID NO 32
<211> LENGTH: 664
<212> TYPE: DNA
<213> ORGANISM: Nezara viridula

<400> SEQUENCE: 32

```
ggggattgaa tgtttgatag cacgttgtga ctccttgtac cggtactttt tgataataag     60

attcaaaatg agtgtaataa ttaagaatgc tttaagaatt cctgctctta aatcggctgg    120

aaaacttttc ggtacaaatt ccactgttaa tgtcaccaaa atccaagcta ccaggagtat    180

ctggaacttg tcgcaatctc aggaaacttt tcatcataag tgccgcaaac acaatttttg    240

tcaatgttct tctttaagaa gtttacacac tcgaggagag aaagaacttg ctgattttct    300

tgtggaggaa atatcagctg aaagaaagtt acaaaaaagt aagaaattac cttctgaaat    360

tgatgggttt aaaattgtaa ttgaaggatc tgaaatcagc cttgtaacga aaaatggtga    420

tgaaacaatt gaagtaaact tcaatgtcaa tcattctgtc gataccgacc cagttgaacc    480
```

```
tgaaattgaa cctacaatgg acaaacctga acttggcgag atgaaatcta gacctacttt    540

tgaagttgaa accaataggg cagggcagac actgggcttc acatgttcaa ctgtatcacc    600

ttctcaccag caaggccagc aagaagaaag ttacaatgat ctatttctta ttgatgaagt    660

tgtt                                                                 664
```

<210> SEQ ID NO 33
<211> LENGTH: 394
<212> TYPE: DNA
<213> ORGANISM: Nezara viridula

<400> SEQUENCE: 33

```
gggggatgtt ggaactggct attatttgaa tatgaatatt gaaagtgcca gagactattt     60

caaaaggaag gtaacttttg tcaccgaaca aatggaaaag attcagaata ttgggctaga    120

aaagagtaaa ataagagaag ctattatgga tgtgatggag atgaagattc aggctcaatt    180

agctacacag agagcggtcc aaaatactat agcgaaaacg tgagaaatga tgagagctgt    240

catacgaaaa atttatgttt cttatattaa cgcttgtatt tataatttac taatgttttc    300

acagagtttt gtatccataa atacctgtta ttaaatatgg aaattatatt ttagttctaa    360

cttttttttt ataaataaat acattttgtt atgt                                394
```

<210> SEQ ID NO 34
<211> LENGTH: 634
<212> TYPE: DNA
<213> ORGANISM: Nezara viridula
<220> FEATURE:
<221> NAME/KEY: misc_feature
<222> LOCATION: 462
<223> OTHER INFORMATION: n = A,T,C or G

<400> SEQUENCE: 34

```
gggggaagaa attgagagaa tggttaatga tgccgagaaa tacaaggctg aagatgataa     60

gcagaaagct gtcattcaag ctaagaacac tctggagtcc tattgtttca atatgaaatc    120

tactgtagag gatgaaaaac tgaaagacaa aatttccgat tctgataaaa ctacaatttt    180

ggagaaatgt aatgaagtta ttcgctggct cgatgctaat cagttagctg aaaaagaaga    240

attcgaacat aagcaaaagg aattggaagc catatgcaat cctattatta ctaaattgta    300

ccaaagtggt ggtatgcccg gaggaatgcc aggtggtatg cctggtggtt tcccaggcgg    360

tgcccctcct aatgctggtg gtgctgctgg acctaccatt gaagaagttg attaaacatt    420

ccatgcgaat aaacacacaa ataatacatt gtataattaa tnctagttga attgcaattt    480

ttttttcctt tctagtcaag agaccttcaa atggccttgt atttttgttt aaaaatttaa    540

tgttaataat gtaactttta caagtatttt gtttatttat aatttttttta tatgttctgt    600

cattggtatc aatgaattat attagagtta ctat                                634
```

<210> SEQ ID NO 35
<211> LENGTH: 491
<212> TYPE: DNA
<213> ORGANISM: Nezara viridula

<400> SEQUENCE: 35

```
ggggaattta tcttaggtcc aagatgaggg ttatccttgc agtcatccta ttcgctggag     60

tggcccttgc caggcccgac ggctacacca ccaagtacga caacatcgac ctcgacgaaa    120

tcctcaacaa cgacaggctc taccagaagt acttccagtg ccacaccaac aaggggaagt    180
```

gcactcctga cggcaagcag ttgaaggaca tcctccctga cgccctgaag agcaagtgcg 240
ccaagtgtaa cgagaggcag aagaagggag cagagaaggt gttcaagcac ctcctcgaca 300
agaagcccaa cgattacaag accctcgaga agatctacga ccctcagggt acctacaggg 360
cccagtacaa gagcgaagcc gagaagaagg gaatcaaaat ataaaaatat ctgtgataaa 420
cttgtatgaa tgatgtgtgt ttgtttttgt ttgtaaattg ttatttaatt aataaataat 480
atgtttataa g 491

<210> SEQ ID NO 36
<211> LENGTH: 663
<212> TYPE: DNA
<213> ORGANISM: Nezara viridula

<400> SEQUENCE: 36
gggcaataaa gctcgttatc acttggtatt cgacattatt atttctcttg ttgccactct 60
tacacggcgt cggactaaga ttaaattttg aaaaatagcc cattgctgaa atgatgaaca 120
tttcgatcgc taacaatatg caggtccgat tttatttttt tgagatatgt caatccaaat 180
gcaaaaacac tttagttaat cgactccagc tgattttact cgagcgttac acatcggata 240
tctgacggct caatctaatt cactctctac aaaaaaaaat attattacta atcaaattaa 300
taatatgcaa taaatttgaa atcagagata catcctcaat tcttaaaata atattttaac 360
atattctttc tattatgagg cttgcgtttg atattcaaaa tattacaaga aataattttg 420
tggaagatgg aaattaatat gtagataatt gttgatattt cataataccg acataaccta 480
accttgttat taaactttaa ctagctgata aaatgtcggg tattaattaa ataatatcga 540
caacccgcaa gtaaaaaacg cgtctaaaga agttttaatt taaaaatata gtgaaaataa 600
ttttattcag cctacgttcc gacctaacta tacaggtctt catcaggact atggtcagga 660
aac 663

<210> SEQ ID NO 37
<211> LENGTH: 548
<212> TYPE: DNA
<213> ORGANISM: Nezara viridula

<400> SEQUENCE: 37
ggggacagct cgcccagctg gaagagggtc aacatggatt cgcaagaact agaccacagc 60
gagctgagga gtcgcctcta ctccatatcc tccctcatct tgcccatctt catcctcctc 120
tacgtggggt ggaggttggc caacaagagg ttcatcgaac tcgcagaaaa gataccaggt 180
cctccgggtc ttccgatcat aggaaacgtt ctcgaactgc gagggacgcc caacgaaata 240
tttgaaaacc tatattcgaa gagtgaaata tatccagatg tcgccagagt gtgggcggga 300
ccaagattac tggtttttct tacaaatcca gcagacattg agattgtcct cagtagccat 360
gatcatttgg acaagtctgc cgaatatgat tttttgagac catggttagg aaatggactt 420
ctagtaagca caggagagaa atggcgatca catagaaaga taatagctcc aacatttcat 480
ctgaatgttc ttcgcagctt tatggaaaga tttaacagaa attcaaaaaa aacattagaa 540
agactaac 548

<210> SEQ ID NO 38
<211> LENGTH: 598
<212> TYPE: DNA
<213> ORGANISM: Nezara viridula

<400> SEQUENCE: 38

```
ggggattcgt gtatcagttt gcaatacaag ctacttttaa atttaatatc atcactggtg      60

tttttaaatt tcaatcataa attactttaa tacacaagtt atttgaagtt gttttaattt     120

atttcaggcc acataaatat ttaataaaat atgtctgggg accaaaaaga aagaaaaagg     180

aaggaaagta tcttagattt gtcaaaatat ttagacaaag ctatcagagt caaattttct     240

ggcggaagag aagctgctgg tgtattaaag ggatatgatc cacttctgaa tttggtttta     300

gatgatacaa cagaatatat gagagacccc gatgaccctt ataagttaac tgatgaaaca     360

aggatgcttg gtttggttgt gtgccgtgga acatcggttg ttcttatatg tccagttgat     420

ggtatggaga gtataccaaa ccctttcgtt ccacaagaat cataaataat ggactaattc     480

taagtttaag aagattaagt tctttcctac ttatgaaaat gaaaagaatt tactttattt     540

aggtttaaaa aactgtttgt ttataaacat gtatatatat taaaaatctc cattttta       598
```

```
<210> SEQ ID NO 39
<211> LENGTH: 689
<212> TYPE: DNA
<213> ORGANISM: Nezara viridula

<400> SEQUENCE: 39

gggattaaaa aaagaaattg attattttat tttttattaa ttataagaac attaattaca      60

atttcagcta ataactgaat aagaatatga ataggtcttg aactaaacat aatatcattt     120

attcctttaa ttttacaaaa aaaatagtaa atcaagatcc gaggcagcta taatttactt     180

tctaattcaa agaattagaa gaattatcct atttataata attacaatta atttattaaa     240

attattaaat tattcaaatt ttattaatat attaattaca attagaattc taataaaatt     300

gggagctgca ccatttcata agtgaatacc tgaaattata acaaaaataa gatgaataaa     360

atgtataatt ttaataacat gacaaaaaat agccccatta ataataattt gtaatttaaa     420

tagaagtaga atattaatta aattatcaat tatttgatca gttggagttg gaagaatcgg     480

aggaattaac caatcatcat tacgaaaatt aatagcatat tcatcaatta accatttagg     540

atgaatacta gccattaata aaaaaaatta atttatgatt agtatattga ataatttata     600

gaataattat ctttataatt tgtctaatat ttaataatta taaattatta ttcttaaatc     660

aaattagcag atccaatata aataatcca                                       689
```

```
<210> SEQ ID NO 40
<211> LENGTH: 662
<212> TYPE: DNA
<213> ORGANISM: Nezara viridula

<400> SEQUENCE: 40

ggggagttga ggtttggcaa ccgacttgtt tagagatcct gcaagaaaat gagagctacg      60

tactgcttaa tcctagctgc tgcagttctt gcagtggctg cagctcacac ttaccatctc     120

ggaaattgcc ccatcgtaga acctatgtct ggttttcaga tgtcaaagtt tttaggttta     180

tggtatgcca tccagaagac ttcaacaggt agcagatgct tgacatacaa cttcactctt     240

ggggaagagc caggcgaata caacttggag caagtttctg aacatccagt cttaggagta     300

gcatcagttg acaacaaata ccattacaca ggacatttaa aggccaattc tgacgttcca     360

tccaaaatga cagtgaaatt tcctttaagt gttgctggaa catcaagttt cacagtcttc     420

atgacagatt acgaaactta tgctggaatt tacacgtgcc aaaaactacc tgcagctaat     480

agaagatcag ctaccatcct ttctaggacg aagacattgg ataagatggt gattgataag     540
```

```
attcgttccc gtctgtctaa cttcggtgtc aacccatacg acctcagcat cattgaccat    600

gctaaatgcc cagcagaaac caaccttaat ttcaacatcg acaaggaaac cttctcacct    660

ca                                                                   662
```

<210> SEQ ID NO 41
<211> LENGTH: 628
<212> TYPE: DNA
<213> ORGANISM: Nezara viridula

<400> SEQUENCE: 41

```
gggctaacaa gaagaaaaat aagtcagcga agtctaaaca gacagctgaa caaaataaat     60

ctaaacagcc tgccgagcaa aataaatcac cacccagaac tagaagcaaa tcaaacacca    120

caaaaacagc tccaactgca ccaaatacca cagccagcaa taattttgat cttggtagta    180

actcacctaa caagcctccg gtacctcaag gttttactga ccccgagccg ccccctattt    240

ttgtctctaa aattgaaaat tttatatcat tcgttcaaga aattgccaat cttatcggac    300

aaaccagttt ccgctgtttt tctagggtta atgacattaa gattaacacg agctctaaag    360

aaaattataa aactctgata aattatttta caactaaaaa atatgaattt cactgttacc    420

aactgagaca agaaaaggca tatcgggtgg tattgagagg cttgcactca accactccca    480

tatccgttat caaatctgat ctagaggaaa taggacataa cgttaggcat atagcatgcg    540

tcctacatcc aacgcaaaaa tatccattgc cactgttttt cgttgatttg gagcctgcaa    600

gcaataacat tgacatattt caagttaa                                       628
```

<210> SEQ ID NO 42
<211> LENGTH: 70
<212> TYPE: DNA
<213> ORGANISM: Nezara viridula

<400> SEQUENCE: 42

```
gggtcagtaa aaagccaagc ttatctctaa tctccaaaat taaaattttt attaaactat     60

ttactgaacc                                                            70
```

<210> SEQ ID NO 43
<211> LENGTH: 685
<212> TYPE: DNA
<213> ORGANISM: Nezara viridula

<400> SEQUENCE: 43

```
ggggacacca caggacatcg ccatggtagc taagatatta ttggtttcac tgggccttat     60

agggttgact tttggcagcc atttacaaga ttctaggcaa ttcctatacc agcagcagca    120

acaacaacaa cctgccagac agtatgttgc atcacaatac caccaacttc ctgcggccac    180

ccatctactt ccgaacaatg tcaatgatgg tgtaaggtat ggacagcagt cacttgtgta    240

cgtaatgcct cagggttcac agtacctcta cgaggaaggc gctgaacagc cacagcaagc    300

tcaacctggt ggagcttatg ttgaatcttt cttcaatttg gtcaataatc catcaggata    360

tcatcaagca gcaagtgacc aaaagcctgt ccatcagcaa cctgctctgc cttctggagc    420

tgaaaaacct gaaaggcttc aggcagagcg accaagtttg ccaacccagg cagctcagca    480

gcagcactac ctccaacagc tggctgctca agaacagata caatatcttc aacaggaggc    540

acaacgacat aagtttatgg ctttgtcttc tcagcctcaa tatttccagc aacaacaaca    600

acgaccagct gctgcagcac cacacaatct cttctactac agtttccctc agcagcaact    660

tcagcagtat gcccaagccg ataaa                                          685
```

<210> SEQ ID NO 44
<211> LENGTH: 669
<212> TYPE: DNA
<213> ORGANISM: Nezara viridula

<400> SEQUENCE: 44

```
gggggtttct cagagtagtg gttccaggcc tctgattaag aatacataga tgaagacagc     60

acgtccccgt tcttgaaaaa atcacttctt caaatgtgga ttcaactgaa gaaaatgttt    120

tgattcattt gagatttgtt catcaattcc atttatatca atgccacttt ttccaaaaac    180

attttcaagc agtgtacttc ataatttcta agtatcgtct tcaagaaggt ggtacaaatc    240

tgctacatac ctaaaaaaat aaatagatat cagttattgt ttcattataa taaattgtta    300

tattagataa gtttttaaaa attacaaatt ctttataaat aaatacattt aaatactttg    360

ttgttctata caaaaggctt ttttaaaatt tatttttgta taaaacagca ttgagttagt    420

aagtatgatt tttgaaattt ttatttcaat tttgcattat ccagttccaa ttactaccag    480

aaagttagtt atatacagtt ttctttattt ttaagaatca attttctagt tattagaaat    540

ttttaagtag aatattcaac atagtaggac aaatctactt tcttattgtt ctagatctct    600

cagatcgatt gcatttgttg tatgattgag caacatttta ttataagcag aaatattata    660

aatgacaaa                                                            669
```

<210> SEQ ID NO 45
<211> LENGTH: 134
<212> TYPE: DNA
<213> ORGANISM: Nezara viridula

<400> SEQUENCE: 45

```
ggggagtgtt gaagggaccg tccgtctggg ttgtgagtag tgttctcgtc gccgttctca     60

tcaccattat aattcggaag atggcagagg tggccaagag tgtgaatgaa gtcatggaat    120

cagttacaac agtt                                                      134
```

<210> SEQ ID NO 46
<211> LENGTH: 225
<212> TYPE: DNA
<213> ORGANISM: Nezara viridula

<400> SEQUENCE: 46

```
gggggtcgca aaaggagtaa tgaactatgc aaggtgatag cccatatatg gtaagaagaa     60

tgtgtacccg aaaaatggaa gtgatcccac agagtgaaat gaaaatattt ttttattatc    120

ctgggactgt tgtcccttta ggacaaatta catatacaaa ataaatgccc gtattgccat    180

acataaaatt aattatttac aattattatt aaaattaaga ttttg                    225
```

<210> SEQ ID NO 47
<211> LENGTH: 664
<212> TYPE: DNA
<213> ORGANISM: Nezara viridula
<220> FEATURE:
<221> NAME/KEY: misc_feature
<222> LOCATION: 557, 610
<223> OTHER INFORMATION: n = A,T,C or G

<400> SEQUENCE: 47

```
gggggcagtc gagtgtgaca tgcccgcctg agactttatg ctggcaggcc cgagtatgac     60

tgtgcttaaa ttgccccaga tggaagagcg caagtcgccc gaagcggcca aagggatcag    120
```

```
cttcagcgtg gctgcgttgc ttgcggactc gaggaggagt cctagccccg aagaagagga    180

tgactcagcg gaagaggaat tggacgtgtg cagggacaag agcccggagc cggggtacag    240

ccagcagcag cggctggtgc tcagccccgc cagtggcccc atcaggccca ctcccttcac    300

cgccttcgct gcggccgccg cagctgccta tgccggtctg ccgccgcaca cggcctcctg    360

gccggtccac cacttcccag gagggccagt cttcccgccc ttccatggcg gtctctcttc    420

ttctccaggt aatagatctc tcaatgttca gttatatata ctcatgtatt gtggtggtca    480

taattaaggc agaacgaatg attggaaggt tcgcggaatc atatgctaac taacgggtag    540

ttcttgttta ctaacangat aactacccgt attacgaaac ttccgtgtat aggtggaaag    600

aaataagtan gatcattata acatcctcca atgaattaaa atagagaata agtgataaaa    660

gttg                                                                 664
```

<210> SEQ ID NO 48
<211> LENGTH: 452
<212> TYPE: DNA
<213> ORGANISM: Nezara viridula

<400> SEQUENCE: 48

```
gggggctctt gctaggtcgc gtgttgttga agtattgtgt gggacatcaa atttatttta     60

ttttgattaa aaatttagta aaatgagtag atttttcgct actgggtcgg actctgagtc    120

tgaaacctct tctgaagagg agcagattgt gaaacaaact gccactttta cgttcagtga    180

tgatgaagaa gatacaaaaa gggtggttcg ctcagcaaaa gaaaagcgct atgaagaact    240

taccaatctt atcaagcaga ttcgaaattt caaaaagatc aaagacatga gcagtatgtt    300

aaatagtttt gaagatttaa tgagagctta tcaaaaagcc caaccagtta tcaataagga    360

agaaaatggt caaactccga agttttatct gcgttgtctt gttgaggtgg aagatttcat    420

caatgaaatg tgggaagata gagagggaag ga                                  452
```

<210> SEQ ID NO 49
<211> LENGTH: 275
<212> TYPE: DNA
<213> ORGANISM: Nezara viridula

<400> SEQUENCE: 49

```
gggcaaccat cttatgttca aacaacgcca tatgatccat ttagacaagt atttcctgca     60

gtcgaccgaa caactttcaa gaaaaaataa gaagaaagca agaaaagacc aaaatgcagc    120

ctatttatct caacgaaata atcccaattc agtttgatga ctggattttt gtatttatat    180

actcatattg agacatacct acataacaaa atttgacaaa atctgaaatt atttgctccc    240

aaaagtaaat taaacaaata ttctgaaaac aaaag                               275
```

<210> SEQ ID NO 50
<211> LENGTH: 569
<212> TYPE: DNA
<213> ORGANISM: Nezara viridula

<400> SEQUENCE: 50

```
gggcgggaag tggagcgaca atattatcct ccgaattcta ctgatgtaga aaagcttggg     60

ttaagacggt aaatgtcttt gaagccaaag acaaaacata aaaaaactga gcgagtttcc    120

ttgaaacaac atgagcggaa tatttatttt aaaaaatgta tcataatatc atagtcgctc    180

caaccgcacc ttgataacct gtatattacc tcctacttcc ccattcctta tctttaatga    240

cataaacata gaaggaatta aaaccagtct tatatattat acttatacat tatagagcct    300
```

```
tcttcttggt tagagatcaa tcaacattat tgattagggg tacaatcctt gagcgtgatc    360

ttggtgcaat cagctctctg tactgttggc ctgaaacttc gtaagtatct tcatctcatt    420

gtgaactaca aatattttat tttcgaatta ttgaaattgg agcgtttgaa agcaagtaat    480

tcctagtata agaagttgtg aatacccatt ttttcccact tgaaccgtaa gataatataa    540

tcataaaatg aataaaaaga aaaaaaaaa                                       569
```

```
<210> SEQ ID NO 51
<211> LENGTH: 586
<212> TYPE: DNA
<213> ORGANISM: Nezara viridula
<220> FEATURE:
<221> NAME/KEY: misc_feature
<222> LOCATION: 534
<223> OTHER INFORMATION: n = A,T,C or G

<400> SEQUENCE: 51

gggggattca gtcgccggct tccatacaaa tattcaagaa acaaaaatgt ctttagacga     60

gaacttcaac actgctgctg aagatgtcaa agcactccag ggaactccag atgaccaaga    120

attattggaa atttatgcac ttttcaaaca agggactgta ggagactgta atacttccaa    180

accagggatg ttcgatttta agggaaaagc taaatgggag gcttggaatg ccaagaaagg    240

cacagcccaa gatgcagcaa aggagagcta catcgaaaaa gtcaaaactt taattgggaa    300

atatggaaag aagtagacat tttgagtaaa gcctaacatt tatttttat taataattta     360

tgatttgctg ctcaaaattt gattttattt tttacattaa tgtaagcaaa catttacaac    420

attcaagaat atttgaacca aaggttgtgc aatttatgta tataatatat atacatataa    480

ggtatttctt ttataatttt tcataaattt atatttgtta aaaaatttga aganagtttt    540

gtaaaatgat tttttaatac atttatatgg atagttgaat attata                    586
```

```
<210> SEQ ID NO 52
<211> LENGTH: 633
<212> TYPE: DNA
<213> ORGANISM: Nezara viridula
<220> FEATURE:
<221> NAME/KEY: misc_feature
<222> LOCATION: 555
<223> OTHER INFORMATION: n = A,T,C or G

<400> SEQUENCE: 52

gggcttcacc ccttacaacg cataagctgc acgtgtgttg ggacagtctt ctgcttacat     60

tctggtttac caacatcggc gtgaacatta aacctggagc gttactagta tgagctccaa    120

tacctgttat agatgtaacc ggactgggca tttcgctaga gaatgcccaa atggtggtgg    180

aggaggaggt ggaggtggat ttggaggtcg tggtcgagac aaatgttata aatgtaatcg    240

ttatggtcac tttgcaaggg attgtaaaga agatcaagac agatgttaca gatgcaatgg    300

agtgggacac attgctaagg actgtcaaca aagtgctgat gagccttctt gttacaactg    360

caacaaaact gggcacatag ctagggaatg tcccgaacaa agagatggtt ctagaggtgg    420

gttcacctca gcttgttata attgtaacaa aactgggcac atggcccgag catgtcctga    480

tggatctagg tcctgttaca gttgtgggaa gacaggacac attagtcgtg actgcgataa    540

gaatgactga atganttgtc aaaattaagc aagttatata tttgtttttg taaggggcaa    600

ctttttcttt tcctttttta ctattacacc ttg                                  633
```

```
<210> SEQ ID NO 53
```

<211> LENGTH: 535
<212> TYPE: DNA
<213> ORGANISM: Nezara viridula

<400> SEQUENCE: 53

```
ggggaaaagt gacaaacaaa cgaatgggtt ccataaggct cagagaaaca gatgaagata     60

tagcagatct tttatccatg caatggatgg aatatgctca tatttatttg ataaatatta    120

ctcctccata ccgcagtttg atattaacgg aactgaatga agctttaagt tttcagtcat    180

attttggagg aaatcagata actgcagctg ataaagctgt tttcagagct ttaagacaca    240

taatggtgat gttttattat taatttacta taaacttatc tttggagatt tttctttata    300

tatgtatgtt atatgggcca tttcgaaatt ttgatcacat ttgggcatta ttttttttaga    360

aaaaagaaat ttgagaaata gtgttttttg gcttcttaac aatctttata gtttgagaag    420

gagttgcggt caaataaata aaaaaattaa aatatataaa ttattttaat ttttgccgac    480

gtttcgaccc actttgcagg tcgtcttcag ggctacaaaa gatacaaaca tgttg         535
```

<210> SEQ ID NO 54
<211> LENGTH: 686
<212> TYPE: DNA
<213> ORGANISM: Nezara viridula

<400> SEQUENCE: 54

```
gggggcagtc gagggtgaga tggcggacaa ggccgcacct tttcatcatg ggccaaaatc     60

cttctcttct atgtatgttt ttacgcttgc cttatgggct ttttctcagc cctcctcgcc    120

ctgttcttcc agactctcga tttcagagca ccgaagtggc aacttaaaag ttcattgatt    180

ggcgataacc caggattggg gttcaggcca atgccaccag aatctcatgt agaaagtaca    240

cttgtctggt ataaaatcag cgataataat tacgcaacgt ggacgacaaa actggatgac    300

ttcctaaagc catacagaga gccagattca caatgggaag cattaaagca aaattgtgac    360

tataatgaca cacctgattc tccagataaa gtatgcaagg tagacatcag ttcatggtca    420

ccttgtgtca aagaaaacaa ttacaactac cataatgctg ctccatgtat tttccttaaa    480

ctcaacaaga tatttggttg gatgcctgag ttctacaatg atactgaaaa gttaccagaa    540

aacatgccaa cagatcttaa aaatcatatc aaggcagaaa aaacaagtca tgcagcagaa    600

ttgagtagat taaatacagt atgggtgtct tgtgaaggag agaatccagc agatgttgaa    660

aatgttggtt cgatacaata tattcc                                         686
```

<210> SEQ ID NO 55
<211> LENGTH: 50
<212> TYPE: DNA
<213> ORGANISM: Nezara viridula

<400> SEQUENCE: 55

```
gggggaggt ctggttcacc catgtgtcag gttaattcat acgaaatccc                 50
```

<210> SEQ ID NO 56
<211> LENGTH: 666
<212> TYPE: DNA
<213> ORGANISM: Nezara viridula

<400> SEQUENCE: 56

```
ggggaggacg actatacttt ttatattttt tttttaatcg cacgattttt attttaaatt     60

tgaaaacgta tttttcctat taatttcatt ttcctggaat acgaatgagt gtgatattaa    120

aaaataattt ccttatttcc tttgcaataa ctgttaatgt cataaataca gagataaacg    180
```

gactagttat ttattttgga aattaaattg tcttgaaggc agactacaaa caattgcagg 240
ctcgcaaacg gtttctcata aaaaacataa tatcaatttt tttaaattta tgtttaatat 300
gcatgttgta tcgatcagat atgaaaaaaa ataaaaatat tattaaaata gatataattc 360
taatatttat ttttgtattt atttatttga gtgtgttttc ttcataaatt gaagtttccc 420
tcagccaaat tccttcccca gtcgtttcat ccacttctcc ctgcctatcg cattctccta 480
cgtcaatcct cggctctata ctctctgcca caacatctct ccatatgacg agcctttcct 540
ctctttttcc tatcctcggt ctcccagtca aatgtcgttt tgggaagcag ttcgctatta 600
gccctttttc tatgctcata ccactttaat ctcctttctt ccattatctc ttatatatta 660
atctta 666

<210> SEQ ID NO 57
<211> LENGTH: 586
<212> TYPE: DNA
<213> ORGANISM: Nezara viridula

<400> SEQUENCE: 57
gggctcctcc tctctcgatc atagagacct caagtcgacg aaatgagaca tgtattcaat 60
gatagtaata caattaccat caggttgtgt ggatgcgtac cctatgcctt gcgttatctc 120
gaaaatagta cgttttggac ttaaaaacgc aggatccgat agttccggag gaactattcg 180
ggtcttgctg tacgcatcaa aatcttcaag gtccaatttg ttccgcatcg atctatagac 240
ctaccaccgt cccagtattg aagcctagca aaatgtttgt atcgacttta cttattttag 300
aaagaaaaac aaaagcggag aatacgattt gcttacccc cgtgaaattc tgaatccaac 360
ggtaccccat tcatggtatt tgagcatgac aggagcttat atttggtaca aaaccgattt 420
cgagccttac tgtaataata tatgtacgga tttaagccca atatgaaaat attcttctct 480
gtttttggta ataataactt ccgattaaca acaattgatt tatttgttgt attttcaagt 540
ctataaaatg gacttaataa acaagaaaaa tgtaatttat ccacgg 586

<210> SEQ ID NO 58
<211> LENGTH: 431
<212> TYPE: DNA
<213> ORGANISM: Nezara viridula

<400> SEQUENCE: 58
gggggaacgt gaactttttc gactaggatt tagtcgcaat gtcttttttc aattttttct 60
ctcaagttgt gccttctgtc aaggcccaag atgacgaaga agagctggta gatccgcaag 120
tggtcctcaa ggagcaatgt ggtgagaaat gctcgaatta taaagataaa ttagactctt 180
gtaatggaag agttagctca agatcacaga ccaccgaaac ttgctttgaa gaactcattg 240
acttcgttca ttgtgttgat cactgcgtag ccaaagacat attttccaag ctgaagtgaa 300
tgtttctaaa aaggattgtt tttaaatttg tagctttaat tgttagtcat atgtacatat 360
aattctgtgt tttaagttaa acaattgttg aaataataaa ttcattagct cagctgagtt 420
attgtttatt t 431

<210> SEQ ID NO 59
<211> LENGTH: 606
<212> TYPE: DNA
<213> ORGANISM: Nezara viridula

<400> SEQUENCE: 59

```
gggggtctta cgaaagttga gttgtagtta tttttatctt ctctgagaaa ataatgtctt     60

gcaaaacatt attcagtaac aaactttact ccagactgat aagtcttcct ggtataaata    120

tgagccaatc ttcttattcc actggtttgg gagatctggg tagtggtgca ggacaggggg    180

gtggagatgg aggatcagta agacaggctg gaggtagctt tggaaaaaga gaagctggat    240

tagaaggaga atattttaac agattaaaac aacaacagct tgaacaattg aagagcagca    300

tgcacgatga cgtaaagttt catgaagaac aaatcaagag acatcaaggt gctattgaaa    360

aaataaaaag ccgtatcaac agtgcagaat aaatttagta tttattttac accaataaag    420

ttagcaatgt tagatttaaa agatattgct ggcctattga tattgaagtt ttgggattta    480

tcaatatatt atatcctcat ttattatatg tggaaaattt atatattgga gaaaaaaata    540

cgtagtatat aattttacag agcttttaaa tgatattatg aaacatttgt atttcattaa    600

gtattg                                                               606


<210> SEQ ID NO 60
<211> LENGTH: 615
<212> TYPE: DNA
<213> ORGANISM: Nezara viridula

<400> SEQUENCE: 60

ggggttgtc ctttcgtgta gtggcatcgt tccagatggt ggtcaattca aaaatccaga     60

aggccggagg agctgagcct gatgcttttg aggcatctat tgctcaagca ctcttagact    120

tggagatgaa tagtgatttg aaggctcaat taagagaact tcatatcact aaagcaaagg    180

aactagattt ggctggaaag aaatctatca ttatctatgt tccaatgcct caattgaaga    240

atttccaaaa aatccagatt aggcttgtca gagaactgga gaaaaagttt tctggaaaac    300

acgttgtgtt cgttggagat aggaaaatcc ttccaaaacc tactaggaaa tcgagaactc    360

agagtaaaca aaaaaggcca aggagtcgaa ctcttacatc tgtttatgat gagattctgg    420

aagatatggt gtttccagct gaaattgttg gtaaaagaat ccgtgtaagg actgatggca    480

aacagatcat caaggttcat cttgacagat tacaacaggt caatatcgag aacaagattg    540

acacattcac atcaatttat aagaaactga cagggcagag aagttacttt tgagttccca    600

caaccctatc tctaa                                                     615


<210> SEQ ID NO 61
<211> LENGTH: 517
<212> TYPE: DNA
<213> ORGANISM: Nezara viridula

<400> SEQUENCE: 61

ggggagtcct agcatgtgct catagcaggc gggtcggagt gtgctctcga gagattacga     60

tgccgtcgtc ctgttcctgg atatttcctc tgctcttctg ccttcatcta gccctagcga    120

aagttcaata taaaacaaaa tgcagcgacg acacaatgga ggtagaactt cggcgcaccg    180

atgacatcaa cgctatttac ctcgaaggac tcaagcatta tccagatcca gcctgtaagc    240

ctgtattatt cggacatcag gcagtattca ggttgtcttt gaatgacgta ttcaaatgtg    300

gcataacaag ggtcatcaac caagcaaatg gcttaagaac attttaccat agaataataa    360

ttgaaacaga taataaagat gcacccaaag aagcaattca agtcaaatgt ttgcaagctg    420

gaaatcacac catctttaaa agaaacgtac tgcctgctgg atttcaagag cccatagatt    480

tggatattac tacatcctta acagggcgtg cccctca                              517
```

<210> SEQ ID NO 62
<211> LENGTH: 631
<212> TYPE: DNA
<213> ORGANISM: Nezara viridula

<400> SEQUENCE: 62

```
gggggtgtca tttatttcaa tgatggtgtt tgctgtcatc tcaaccatgt tgttgttagt     60

cagtttgatt ctatattgca aaaattcagt gcaagaagta aaacgtttgg catttataaa    120

tggttatgtt gattcaatgg tatgcacata cttttatggc tatttgaaaa aaataattcc    180

tgatcaagga actggaacag gaggtttata tgacaaaata atgatctaca aagaaaaaca    240

aaaccttacc aacaaagatt ttccgtttca taaaatcttc attattatat gtgcatccgg    300

atttgttcca cctacccttg aaaagataga taacaaacgg atcgaagcta gaaagcactt    360

agatccgttg gttttaaata atgctggaat aaatggtcga cgttatacga cagctgtata    420

caaggtcaag taccgcaatt taaaggatca cattactgtt gccatggagg gtactcctcc    480

attacttact ctgtcggacg cttctgcaga agatccagaa ctaaaaaata acaagaaaca    540

aatcattgaa atgttttata aaagattatc aaagaaattg gctgaaaatg cagaatttgc    600

aaattcttat gaggttgtat tttacaatga t                                   631
```

<210> SEQ ID NO 63
<211> LENGTH: 572
<212> TYPE: DNA
<213> ORGANISM: Nezara viridula

<400> SEQUENCE: 63

```
ggggtggtgt ggaaaggtga ttagagggtg ttaatacgtt aatagaatat ctatttgatt     60

aaacttgtgt attgtttata ttgttattag ttactttgtt gtatgtgaaa agtgcaacta    120

gttaatgttt aaagcattaa taggatacat atatatttga ccaaacttgt atagtgttta    180

tttgatcaaa cttttgcagt gaagcccttt acagtttagt gccaggtgtg aggtgcaatt    240

tggcttctta ataaaaatta attttcccga ggatatcacc agtacagagt tgcctgttgt    300

gtatattctt tctgaattat ggatgaactg cagggagaag tggatgaatt gaagcgacag    360

cttgagtttg agaggcataa ggctgaagtg gctagattaa ggcaacaaaa tgaagatcta    420

agagtttacc aagttcttga tgagtgtgaa gggtcagatg ttgatgataa cgtagaacat    480

cattcagaag tagaatttga cataagcgac aatgaaattg aagctatgct ggaagaaggt    540

tttgaaaaag gagtaaaaac aaaggacgaa tc                                  572
```

<210> SEQ ID NO 64
<211> LENGTH: 70
<212> TYPE: DNA
<213> ORGANISM: Nezara viridula

<400> SEQUENCE: 64

```
gggggggggag gtacgatgtg tccctgtgtc atgtactgta catcgattct gtgtacaaca     60

ataaagtgcg                                                            70
```

<210> SEQ ID NO 65
<211> LENGTH: 621
<212> TYPE: DNA
<213> ORGANISM: Nezara viridula
<220> FEATURE:
<221> NAME/KEY: misc_feature
<222> LOCATION: 547, 548
<223> OTHER INFORMATION: n = A,T,C or G

<400> SEQUENCE: 65

```
ggggaagtaa cagctgatac tacagacacg gcagcttgaa tgatgtgtct catcagtttt     60
atttatttct gttaattaag gtgaattcgc gatggcagta acattgtggg gattgttaga    120
ggcttcgata ttgttcctca atgccgtttg tgttcttcat gaagaaagat tttagcaaa     180
aatgggatgg tggagagcac caagtataca aggctttggt gaaaaaccta ctctgaaaag    240
ccaatgctta catttaatgc attctatcag aacagttacg aggataccgt tgattttcat    300
caatatagta gtgattttag taaaacttat tttgggttga tacacttttg actccattcc    360
ttgaatcctc taaaatgtct gtgaaaaagt tcatagatat tggtgccaat ttattagatt    420
caatgtatca aggtatttac catggaaaga gcaaacatga acccgatttg tccgatgttc    480
tgacccgtgc atggggcaat ggtctggata agattatttt aactggtgta agtttgaaag    540
aaagtannaa actttagatt ttacagacac tgatagccga ttgtattgca ctgtgggctg    600
ccatccaact aattgcgatg a                                              621
```

<210> SEQ ID NO 66
<211> LENGTH: 577
<212> TYPE: DNA
<213> ORGANISM: Nezara viridula

<400> SEQUENCE: 66

```
ggggagaacc cgtcaccaat tggtaaggta tatcagtcct tacgctttct cgaataattg     60
tcagtatcca gtgtgatcta caattattaa cacatctaca atggcatcca atcaagtacg    120
ccaaaatttc catgctgact ctgaagaggc tatcaacaaa caaataaata tggaactatt    180
tgccagctat gcttacatgt ctatggctta ttattttgat agagatgatg tagctttaga    240
aggtttcaca aaatatttca agcatgcttc tgaggaagaa agagaacatg caatgaagtt    300
gatgacttat ttaaacaaaa gaggaggaag agttatcttt tctccaattg ctgctccaag    360
tacaaatgac tggggatctg ctgagaaagc tgtcgaagca tctcttcagc ttgagaaaga    420
tgttaatatg agcttgttga atcttcatgg tgttgcatca tctcatggag atgctaacct    480
ctgtgatttt atcgaaaatg aattcttgca agaacaagtt gactcaatta aatctcttgg    540
agatctgctc actaatgttc gtcgtgtcaa ggaagga                             577
```

<210> SEQ ID NO 67
<211> LENGTH: 544
<212> TYPE: DNA
<213> ORGANISM: Nezara viridula

<400> SEQUENCE: 67

```
gggtcagtcc tctcgtggct atcgttgtgt tctgttctct ctccatctct ctctcatctt     60
ctcgtctctc tacgctctct gttcaagtct caggctccgc cttttctacc gtcctctctg    120
cctgcgccac gacttgcttc acaactattg atatttataa gttcgcagta tcgtaaacct    180
attccattac tgttatggcg ttacttttaa aatatataga tgacatacaa gaaatatttg    240
acacaaatgg agacccacgg acgagggact ggccattgat gtcttctcct ttgccgaccg    300
ccatgatctg catgagctac atctacctgg tcaaggttgt tggccccaag ttgatggaga    360
acaggaagcc cttccagctg agacatgtcc tcatattcta taatctgttc caagtgatct    420
tctcggcgtg gctcttctac gaggtgagtc ccgtttagca accacttagc ttttagtttt    480
ggttacagga tcctacaata agctacataa tgacttttca atacttgtac tgatataaat    540
ctca                                                                 544
```

<210> SEQ ID NO 68
<211> LENGTH: 314
<212> TYPE: DNA
<213> ORGANISM: Nezara viridula
<220> FEATURE:
<221> NAME/KEY: misc_feature
<222> LOCATION: 297
<223> OTHER INFORMATION: n = A,T,C or G

<400> SEQUENCE: 68
aactgggcaa aaagaaggag caaacttagt aactggtggt tcaagagttt ggtaatgcag 60
gatattttgt tgcgccaacc atcttttctg aagttactga tgacatgacg attgcccggg 120
aggagatttt tggaccagtt caacaaattt tgaaattcaa atctctcgat gaggttatac 180
acagggcaaa tgattccaat tatggtttag ctggagcagt attttcaaat aacattaata 240
atataaacac cattatccaa ggtcttcggg caggaactgt ttgggttaac acctatnata 300
caataactgc ccag 314

<210> SEQ ID NO 69
<211> LENGTH: 573
<212> TYPE: DNA
<213> ORGANISM: Nezara viridula
<220> FEATURE:
<221> NAME/KEY: misc_feature
<222> LOCATION: 78
<223> OTHER INFORMATION: n = A,T,C or G

<400> SEQUENCE: 69
gatcgtggcg gctgttcggg tcaatgtcga gcagcgggac gaagacaact gagtagccaa 60
tgattaatta ttgaactngg cgaatagagc gccatcaaat gtgccaagac aaacacagtc 120
tttcctatcg aatgcagttt cgaagttaat aaaataagaa tttttcttta cgagaccatg 180
ttcgaaaaac attggttgat taattatttt tctttttga tttattattt ccatggcagc 240
tgtgaaaagt gttaagtgca attttgagaa tttcaccgga acgctaattt ttctctccat 300
attgtgtcta aagtgctaag ttatactgca attataagta tgaacattcc tttgtgaata 360
attggtggaa actccaaaat tacaccggtg aaaattccaa gctttcaatc gcatttttcc 420
tttaatatga tttttgcact tacactatga acaggttcca tacatttttt aaagcgtatt 480
tgtatcaaat ttttaattat ttttgcatta ttatatgaat ttgtgtgatg taattatgat 540
gtaacttgtg cctttataaa cgattatacc acc 573

<210> SEQ ID NO 70
<211> LENGTH: 578
<212> TYPE: DNA
<213> ORGANISM: Nezara viridula

<400> SEQUENCE: 70
ggggagacga ttctgagctg ggttgttgta attgttggga ttgattagta cataactgtt 60
accatgaggg aaattgttca cattcaggca ggacaatgcg gcaaccagat tggtgccaag 120
ttctgggaaa tcatcacaga tgagcatggc attgacccca ctggctcata ccacggtgat 180
tctgatcttc agcttgaaag aatcaatgtt tactataacg aagcgtcagg tggaaagtat 240
gtacctagag caattttggt tgatctggaa cccgggacca tggactcagt acgttcagga 300
ccttttggac aaatctttcg acctgacaac ttcgtttttg gccaaccagg tgcaggaaac 360
aactgggcta aaggccatta cacagaagga gctgaactcg ttgattcggt tcttgatgtg 420

```
gttcgcaaag aggctgaatc atgtgattgt cttcagggtt ttcaactgac tcattccctt    480

ggaggtggca ctggttctgg aatgggaacc ctgttaattt ccaaaattcg tgaagagtat    540

cctgacagaa tcatgaatac ttattcagtt gtaccatc                            578


<210> SEQ ID NO 71
<211> LENGTH: 527
<212> TYPE: DNA
<213> ORGANISM: Nezara viridula

<400> SEQUENCE: 71

gggcaacaag ggacacctat agcagaatca ccattaacat ctatgaatag ataccttcat     60

tggagatgat acaaatgggt cacggtgatg gatcttttta ctaaagcagc aatggtatac    120

atgatccagg agcggtggtt ggaagcaatg ttaggagccc aaaggacata gttccaattt    180

tatggtgtgc ctgaccgcat tgcatcggat gggggcaagg aattcaacaa tgccaccatt    240

ctagtagaag cgaaaggttt ggagatcaca tagcacatta acacccaaag agtagagagt    300

atattgaacg ttgcaaagca cgctaagtga cctgcaaata caccaactga taaaaggact    360

agagccagat gtagtgaaga caaaagcagt cacagcatat aatcagtcta ttgtgttttt    420

tgtttttgtc caccccttgc tcgccttcta ggttatacgg gtattttctc gggcatcagt    480

atatgatttt attggtgtaa tattaaagtc tgatgacagt tcactcc                  527


<210> SEQ ID NO 72
<211> LENGTH: 575
<212> TYPE: DNA
<213> ORGANISM: Nezara viridula

<400> SEQUENCE: 72

gggggattgg gggaacgtgt gtgaaatgtg ttgtgtaaaa tttatgtatt gatttttata     60

ttttttagt taaaataaca gacaatttgc caaaatgggg aacgttaatg catctagtca    120

aaaaagtacc tcggacgcat ttgctgcatt tgaaccagaa aatgttgttc ctttagtgga    180

tgaaaagttg gaaaatccag ggtctatgga agagctgcac aaaaaatgta aagatatatt    240

tcctgtaaat tttgaaggag ctaaaatagc tgtccaaaaa ggtctgagca atcatttcca    300

aatttctcat tccttaaata tgagttcttt ggcaccatct ggttatcgat ttggtgctac    360

atatgtcgga acaaaacaat atggccctgg tgaagcatat cctgtgttag tgggtgacat    420

agatccagtc ggaaatctta atgcgaacat ttatcataag tttaatgaca acataattgg    480

gaaaattcaa gcccaggtac aaagtagccg ttgtacagca tcacagtacg ttttagatta    540

cagaggtagt aattacacag ctacagttac gtttg                               575


<210> SEQ ID NO 73
<211> LENGTH: 117
<212> TYPE: DNA
<213> ORGANISM: Nezara viridula

<400> SEQUENCE: 73

ggggcccact cgtcggtctg ggaggcgatc ttgtgtccag cttctttgtg ttgtgtcagt     60

cctaaatcgg gtctttttag ccttcacagt cagtgttcat cgccgtacgt catatat      117


<210> SEQ ID NO 74
<211> LENGTH: 301
<212> TYPE: DNA
<213> ORGANISM: Nezara viridula

<400> SEQUENCE: 74
```

```
gggggctact gtatctatta tataacttgt gtccattata taattaaata atcgttgatt     60

cctcttttga aaaaatggaa gatttaaaga aatattaata aataaatatt tttttatgat    120

atctcaatga tttttgactc catataattt tgtgccatga gccttatatg tacacttttg    180

ttttccttaa ttggattttg tgatatctta accttattta tgtcactcat ccatatgagt    240

attttcattt acacagctat aaatatatct attatgaaaa ctattttact aataaaattt    300

t                                                                    301
```

<210> SEQ ID NO 75
<211> LENGTH: 615
<212> TYPE: DNA
<213> ORGANISM: Nezara viridula

<400> SEQUENCE: 75

```
ggggacaaga cttcttcaag atgaaagctg cactctgcct taccactctt ctcgctgttg     60

tctgcctttc ttgggcggca actccggaat acaaagctaa agttgttaca gcaattagtg    120

cttgctcaaa agaatacaat gctgaactaa aggatattct ggaaatcata aaacaaaata    180

aacttccaga aaccaaggat caaaagtgca ttattggttg cttctttgag aaaatggact    240

atgtgacgga tcacaaagtt gattgggaga aggttaaggc aatgaaccca cagaaatatg    300

acacccctga tttggtagaa aaaatcaacc aagttactga cacttgtgct aaagttgtga    360

ctgaaggatc aaccgacatt tgcgagttag gtgtcccagc aataaaatgc ttgaaggagg    420

aagcagataa ggtcggattg ccaaaaccag aagtaaagtt tgataaacac tgatgccctg    480

atgatgaaaa ttttatcgat aaaggacaat aatacactct gggatacata cttaatctac    540

aaaagccaaa ttaacattta acgttaatgc catttagaaa tagttctttt attttgtgtg    600

tgctatcctg tataa                                                     615
```

<210> SEQ ID NO 76
<211> LENGTH: 403
<212> TYPE: DNA
<213> ORGANISM: Nezara viridula

<400> SEQUENCE: 76

```
aaaagaaatg atttattcta attagaatag aaagtaatga tgtattcatt gtttctgata     60

tgttgttttg tgactgttgg aagtgcaaca tcgatcagtg aacttctctt tccaactcat    120

aataaatgtg gttgttttta ttatgagcaa tgccccaaac ttcatgtacc taactgtact    180

attgaagatg aaaattatga ggatctttgt ctacaaaatt ctgcatcttc aaactctcct    240

gagatatgca acaagtggtt tctggaaggt tttaataaac agttaatctc agaaaatggg    300

actctcaaga tatcaatttc gttctcttct gccttattcc agaaaattcc tcttagtgtt    360

catctctttt atcaaaatca gtgcttggat attaacaata ata                      403
```

<210> SEQ ID NO 77
<211> LENGTH: 514
<212> TYPE: DNA
<213> ORGANISM: Nezara viridula

<400> SEQUENCE: 77

```
ggggtaccga aaatttatta cttcatcgaa aggtgccccc catgaaaatt caagaccccg     60

tcaaaatgtg cccccctcaa aaattttgat ggcgttcctt gccccttgaa accccccttct    120

ggacacctct gcgtatcatt acacacatta tttcacggtc tgttgtttaa tgtactactc    180
```

```
aaacagtaaa ccgatcgatt gagctggcag gaaattaaaa gtaactacct atgcgtgtag    240

aaaaaaccat ctgtattagg aaggcattga taaagggata gaggcgaagg aggaagattg    300

ttgttgatta ggaatggcaa gtgtttgaat ctaatcggaa aggaaagatt gaactcagaa    360

aatatagaat taaaatcact attccattgc aaaatggttg tgattttaat ttataaaaaa    420

tataaagtga ttcatgagat taaaatcttt agattagttg agcgttgctt ttagcttggg    480

attgagtttg gcaacatagc gatattctag tata                               514


<210> SEQ ID NO 78
<211> LENGTH: 326
<212> TYPE: DNA
<213> ORGANISM: Nezara viridula

<400> SEQUENCE: 78

tttaatatat tcttatttgt tatttctaat ggtaagtatt aagttctgat taatgtataa     60

tttttttgtt tggtgttgca taccgtaaag atgtaaagat cattggccac ataatatggt    120

attatggaaa tttattgctt gccaagataa caggataacc aaccatagct tagtaaccta    180

tcccttggag gccaagtcaa tgtacttccc ttcacttggg tttacgagca ttgaggaatc    240

ggtctagata catggattat ggctcttttc agggtcacca ggtgcacaaa tacttgcatt    300

tcttcaatga aacagattgt acatac                                         326


<210> SEQ ID NO 79
<211> LENGTH: 341
<212> TYPE: DNA
<213> ORGANISM: Nezara viridula
<220> FEATURE:
<221> NAME/KEY: misc_feature
<222> LOCATION: 304
<223> OTHER INFORMATION: n = A,T,C or G

<400> SEQUENCE: 79

ggggaacgca acacttcttg aggaaagcgc tcaactgctc ggaccaaaga ttgtttgtgg     60

ttttccaact tagggtatgc tctgtggcat gccatccttt ccagttcggt ccaaagccga    120

taagctaggt cagggcctcc tgagggccaa tccgagacag agatgaactc tggaatgttc    180

ctttgcagcc actgctgagt tgacctggcc ttgtgagctt gagcggaatc ctgctggaaa    240

acctaatgac ttccagcaaa cggagtatca tttagatgct tgacaacaag ttccaaaata    300

tcancctgat agtgtttagc agctgtttta actccttttt c                        341


<210> SEQ ID NO 80
<211> LENGTH: 615
<212> TYPE: DNA
<213> ORGANISM: Nezara viridula

<400> SEQUENCE: 80

tgttcatgaa gactatagat cacaaaagaa tgacattgct ttattacgtt tagatgaaga     60

tgttgttttc actgataaaa taagacctat ttgcctacca caacctgcta gcctaagatc    120

ttctactttt gatagaaaat atccatttgt agttggctgg ggtgaaacca gtctcgaggg    180

tccttcttca gacattcttt tacaagtaca agttcctgta gttgacaatg atagctgtaa    240

aaaagcttat gcaaaacacg gagctatcat aactgagagc caactttgtg ctggagaaaa    300

gaaaggaggc aaggattctt gtaggggaga ttctggagga cctttaatgc taccacagaa    360

tggatcatat taccaaattg gtattatctc ttttggttat aagtgtgctg aaccaggata    420

cccaggggtg tatgctcgtg ttacgtctta ccttgattgg atcaaaaata atatggaata    480
```

```
agattacatt ttgttttaat tttaccaaat agcacaaaca tatctgtgaa actgcaaaaa    540

gtgtattaag tgcaattttg tgaattttta tgggtattcc tccaatgata atttatctct    600

ctttctttgt ggagc                                                     615


<210> SEQ ID NO 81
<211> LENGTH: 53
<212> TYPE: DNA
<213> ORGANISM: Nezara viridula

<400> SEQUENCE: 81

ggggtggagg tctgatgcac cccagtgtca tgaaactgtt aatggtaaaa cag            53


<210> SEQ ID NO 82
<211> LENGTH: 604
<212> TYPE: DNA
<213> ORGANISM: Nezara viridula
<220> FEATURE:
<221> NAME/KEY: misc_feature
<222> LOCATION: 467
<223> OTHER INFORMATION: n = A,T,C or G

<400> SEQUENCE: 82

tgatgacatt ccattaagta ttttatttga cttatattgt ttcatgacta tttaaaaaat     60

aaaaataaaa taattcatta tttttaaaaa ctgcattgta ataattcata tttatattca    120

cttcttttgc atatgattca tgatagtatt tattattaaa taaaatagga atacaagtat    180

tttacttaat agggttataa aattgtaatg aaatatttgg aatttgaaag aaatttttaa    240

taataagttc tacaataaaa tttacttaca tgttttatgt aatagaaaat aattatgtgt    300

aatggagctc aatatttatg tgtaaataaa taacttaagt ccagtcagtc cttaagaatt    360

taaaattttg ttgtagtatt tagtatttgg aaatatcaca aagatgcaga attaaagaaa    420

aagaagaaaa gttgggagaa ttttcataat tgagacaaaa agaaggntaa atgaagagaa    480

gagataagaa aaaaaaaaga acttgaatag tgattaaaga gagataattt aaaataaaac    540

atcatgtaag taaaatcaaa aagctgaaaa cattcattac atatgttttt tctacaaata    600

tttt                                                                 604


<210> SEQ ID NO 83
<211> LENGTH: 623
<212> TYPE: DNA
<213> ORGANISM: Nezara viridula

<400> SEQUENCE: 83

cggccggggg agttaaaaga cacatgttct atatatcatg cctctttgct attctttcgt     60

tgaaaatgaa aattgataga atgccgtgat aagtagtcac tgttgctagc tttacttcaa    120

aatttgaatt cgaatatgtc ctacagcatc attctcagtc atttgagtag gttcccacta    180

ttctcttact caagaggata tagtgtcatt accagccaaa atgtgaaaaa tatccctgtg    240

agtttcagat attattcatc tggtggaagg aggcctaatt ttttctccca atttatagaa    300

aatgttaggc aagacttggc aaaaaagtaaa gagatgaaag aaagtttgaa aaagtttagg    360

gaagaagcgc agaaattaga acaatccgaa gctttacaga aagcaagatg attgttgttg    420

cagagccaag tttcatactg ttgaatcaga agcatcgaaa ggtggtgaag ttttcaagga    480

gaaattggac cacattaaag ataaagtcag tgatgtgctg gaggaagcag caaaatcaga    540

aatcgggaaa aaagtcagct gggagcagaa attggaaaga ctgcgagggg agctgctgaa    600
```

```
acattatcag aaacaggaca gca                                              623


<210> SEQ ID NO 84
<211> LENGTH: 637
<212> TYPE: DNA
<213> ORGANISM: Nezara viridula
<220> FEATURE:
<221> NAME/KEY: misc_feature
<222> LOCATION: 7, 29, 30
<223> OTHER INFORMATION: n = A,T,C or G

<400> SEQUENCE: 84

ggggagngta ataaggaagg ttttgaatnn tgtgaacttt gccttattca aaataattta       60

aggaaatgtc tttatcaaat attttgggaa gaagccttaa tgtcttaaaa aataaaagtt      120

tttgtagtgt aatacctggt aaaacttctt cgttattgaa gtatcctgct gtttcttctg      180

tatcatgtct taacttccat aaaatatcaa atgaaaaacg aattgcccct tcagaaccca      240

aggtaaaact gactgatgca gtacgacatt tttccataac ccaacctaaa ctttctggac      300

atggtgacca ttccaaactg tgggtctatg aacgatatgt gtcagcagca ttactgggta      360

ttgttcctct tggtttaatg atgccgaaca tactctttga tctcttgatt gcagtagcca      420

gtgtcatgca tatacattgg ggtattgaag ctattgttat agactacatc cgcccaatca      480

tttttggtaa tttgatatca aaattagcgg tctactttgt ctatctcctt tcaatattta      540

ccttggttgg tcttttgaat cttactttca acaattgtgg ccttgctaat agcatcaagc      600

ttctttggag aataagcaaa caagaataga agtaata                               637


<210> SEQ ID NO 85
<211> LENGTH: 638
<212> TYPE: DNA
<213> ORGANISM: Nezara viridula

<400> SEQUENCE: 85

gggctgttct aagattttgg gcgagcgagg agagtgagtt cgggcgcgct cgtattcctt       60

tggttcttcc attacaacca ttctttgtta cgatctttta tttctccttt agttaattat      120

taaattcttt catattctat atttaacaat tctttaaatc ggagatcaat gtgaaatggt      180

taattatttc aaataaaaaa aattaaaggt actttagaag aagaaatagt gaaattagcc      240

atatgaggcc tgtttgagaa cataaatcag aataaaaacta cattttatta taaaatgctt      300

aatttaacac tgataagatg aatttaatca aaactttaat gtggtttttc tagaaaatcg      360

taaacatgtg tttactccaa tatataaagt ggcatttcca gttagccaat tttgacgaaa      420

aatttgccgt aacatcccca gcttataaaa acctcaaata tgcaatttca cttttataag      480

atttcggttt tttgagctag actgttaata cccacacaga cagaccattt tgcgggactt      540

ggttatttgg actcagggga cttcaaaacg agtatttcca ttgaaaagtg agattggaaa      600

attttcacga tcacaatact ttcttttact atacattt                              638


<210> SEQ ID NO 86
<211> LENGTH: 444
<212> TYPE: DNA
<213> ORGANISM: Nezara viridula

<400> SEQUENCE: 86

gggggcagtg gattttctga aaagatggct gcttcgttgg gtcgccaata tctcaggaag       60

tttaattctt ccaaaactct ttttaagagc ttccttcagc ctctgctgta gctggagatc      120

atggtgctgg tgttaaactt tggcgtaatg tgagttattt tgctggcttc ccttctgttt      180
```

```
tgttatgcat gttaaatgca tatttggctc atattcgtca tgaacatgca agaccagaat    240

ttaagaaata tgatcattta agagtgcgta ataagaaatt cccttgggga gatggaaacc    300

gttccctgtt tcacaaccca cacaccaacg ccttaccaga tggttatgaa gcgtaactag    360

tttaaaaata gtaaacagca tgtatgtaat taaactgaaa tcattatgtt atcatttata    420

agaataaatt taagggttaa taac                                           444


<210> SEQ ID NO 87
<211> LENGTH: 69
<212> TYPE: DNA
<213> ORGANISM: Nezara viridula

<400> SEQUENCE: 87

ggagggggag gtacgatgtg tccctgtgtc atgtactgta catcgattct gtgtacaaca     60

ataaaatgc                                                             69


<210> SEQ ID NO 88
<211> LENGTH: 652
<212> TYPE: DNA
<213> ORGANISM: Nezara viridula

<400> SEQUENCE: 88

ggggaaacca aagtatggct ggagtacggc aaaatgtctc tggaacaaac agcatgtgaa     60

gatttaaagg cttttgaaag aaggcttact gaagttattt catgcctaca acccgcgact    120

ttaagatgga gaattctctt agcaatcata tcaacatgta cagcaattgg agcttggtat    180

tggttgacag accctcatac atcagatgtt tctttcaccc aaagtctcat taatcatcca    240

ttcttctcta catctagcat aattttagtt ttgctactaa tgtctggtat acacaaaaga    300

gtaattgctc catcgataat aactgcaagg accaggatag tattgactga ttttaatatg    360

tcttgtgatg acactggaaa gcttattttg aagcctagac cagctcaatc atgacatgaa    420

tagaaatagt cagcaaatgt acataattaa gaattggtta tggtgaggct gtcattgaaa    480

gtggaagaca cttagctcct ttttttgtta gaacagagtg ggaaagaatg tttaattatt    540

tctttttgag ttgtatttta tatttgaagt aattttttat ggtactcgct tcctttttat    600

aaagattgtt gggataactt agtgtcttct atttgtcaag ataataatga ac            652


<210> SEQ ID NO 89
<211> LENGTH: 340
<212> TYPE: DNA
<213> ORGANISM: Nezara viridula
<220> FEATURE:
<221> NAME/KEY: misc_feature
<222> LOCATION: 14
<223> OTHER INFORMATION: n = A,T,C or G

<400> SEQUENCE: 89

ggggacagtc agtngcaaat atgatccaac agctggtagt cctcttctcc ttggtggccg     60

cctcttacgg cttcttcttc cctccgggac tcctcggcaa cggcaccaac cctctggctc    120

ccttcctagg ctgaggattg gttcattctt ttacacttaa actaatttca aattgaagta    180

actatgaaga taaaagtaca atgaattgta cccaaactta caacttttaa gttttcaact    240

atgaaatcaa atgcaactct agctgtattt catttacttg tgtattatac caaattaatt    300

ttttagatat tatataatga ataaacattt ataaaacgcc                          340


<210> SEQ ID NO 90
```

<211> LENGTH: 492
<212> TYPE: DNA
<213> ORGANISM: Nezara viridula

<400> SEQUENCE: 90

```
gggggagcca ccggtaactt ctcttcttat tgcatttgtg tgtgtatgtt ccattgttaa     60
tccggcttat gtggtacttt gttgcacgaa ccagtgaaaa agatactttt aggcaagacg    120
ttcattcccg aacaggtctt cgatgaatat ttaaatggtt tagccgaatc agaattcagg    180
ggtgatcatt acgaccttct aaagcacaac tgcaataact tttcagacaa tctcagtcgc    240
tttctcgtcg gcaacggaat accagaatac attttgaaac tacctgagga aatacttagc    300
acgccatttg gacagagatt tcaaggattg attgaacaga tcagccagaa ttctccgaac    360
ttgcagccta cccaacggag agccgcctca cctgaattct accaattgaa ttcagatatt    420
gaagctgcta gacatcattc ttctcttctg agggaaaaac gtaatgctct gtgtgaaaaa    480
ttagcaaagc at                                                        492
```

<210> SEQ ID NO 91
<211> LENGTH: 503
<212> TYPE: DNA
<213> ORGANISM: Nezara viridula

<400> SEQUENCE: 91

```
aattattcag tatcctggat aaacatagtc gactgtatat aaatcaaaat gtatatttta     60
gattttaatt gttttattta ttttcttttt tcagatgatt cattaagttt ttttaacata    120
aataattgaa tcatactaaa tttctgaaga gtgccgagtt tatgaatgta cttttaaata    180
atgggctgta ttatgattga aacaagtatg agcctataac taaagaaata taccatcatt    240
tttgaagtaa cttgatgcat ctcaattttc taactttcca caagaataaa aaaaactagt    300
caatatttat ttataactat aaaatatatg tattttattt ggattcatta tattaattta    360
aattgtgtta aattaatatt tctttaggat gttttgaata aaatgatgtg tatatcttga    420
tttctacagc tatgatatat taatgatctc atttattaac aaaagtaatt cttttcaaat    480
ataaatttca taaatctcca taa                                            503
```

<210> SEQ ID NO 92
<211> LENGTH: 647
<212> TYPE: DNA
<213> ORGANISM: Nezara viridula

<400> SEQUENCE: 92

```
ggggaaaaac gttggtcatt cttggggtgg cttagttgtt tattgaaatt atttctttta     60
aaatggcaat gccaagaagt tatggtggct tatctgatta cagaaccgtt cctgcacctt    120
cttttagtcc atattctgaa aatggaggga gtgtagtagc tgtagctggc gatgacttcg    180
caattatagc atctgataca cgtttaagta caggttttca aatttatacc agaaaccagt    240
caaaattatt taaattgtct gacaaaacaa ttcttggtag tactggttgt tggtgtgatg    300
ttctttctct tactaggctt gttcaaaccc ggataaaaat gtatcagtac gatcataata    360
aagttatgtc cactccagca gttgcccaaa tgctctctgt actactttat tataaacgct    420
ttttcccata ctatgtagcc aatattcttg ctggaataga tgataatggt aaaggagtgg    480
tttacagtta cgatccaatc ggtcatcatg aaagctcaaa attcagagct ggaggaacag    540
ctggagcttt attacaacca ctgttagaca atcagctcgg tatgttgaat caagaaaatg    600
ttcaagacaa aacatacact ttggaaaaag cccatgcaat tgtaaaa                  647
```

<210> SEQ ID NO 93
<211> LENGTH: 648
<212> TYPE: DNA
<213> ORGANISM: Nezara viridula

<400> SEQUENCE: 93
ggggtgtagt ggtagctgat ttatatgtat gtagttggtg tctttaacca tgattagaat 60
tttatttttt atctatagct gtgcttcatt attgagtgct agtagtcttc atcgaggata 120
taattttgtc ggaacagcca gtgaaactga tggtatattt gttaatgtta tttctgatat 180
caatcagtat ataaaagaca ataagtttga tgttcacaaa ctcatggaca ttcctataaa 240
tttaccattc acctctgtga gtttatctaa tggacaaatg agagacttct cttctattga 300
acttcataag tcttctattt taccacaaag tgaacgcagg ctgtattgga ctctaggagt 360
aggtttggaa aatttttcat tacaatacga cttcaaatca gatttttttg atgtttttaa 420
gaattcaggt agtctgaaac tgacagttcc aaaaaaataat attcttttaa gtggcacgat 480
agatatatca ttgccaaaat gttcgacagc aattgagatt gtgacttata tggattttcc 540
tgatgttaaa gttgaagtgc aaccttggag cgtaaaaaat ttctttttta aaaatttact 600
agaatttgta gtaaatcata gtaaaactct agtaagccct gcattaaa 648

<210> SEQ ID NO 94
<211> LENGTH: 550
<212> TYPE: DNA
<213> ORGANISM: Nezara viridula

<400> SEQUENCE: 94
ggggcactaa cttagtcttc gtgagtgcca gcttcttctt aaggtaattc accatggctg 60
agaaacccac aaaagaaaag gcggaaaaga agcctaagga gaaagtagaa aagaagccta 120
aaaagactat tgaaaaacct actgaaccag ctaagccaaa aaaatctaag cgaatgatta 180
ggaaaaaacc cgggcgtttg tatgctaaag cggttttcac agggtttcag agaggtcaaa 240
gaaatcagaa tgaaaatact gccctgctgg ctgtagaagg atgtaaaaca caggaagaca 300
gcaagtttta tgtcggaaag aagtgtgtgt ttgtttttaa ggctaaaaat cgaactaggg 360
ttcctggccc cgtaaaaaag aagaccaagg ttcgcgccat ttggggtaaa gtaaccagga 420
cccatggctg ctctggagca gtaagggcca agtccaagtc taatctcccg gccactgcca 480
tgggcaggag aattagaatt atgctgtatc cttctttgat ttaattttga aaataaattt 540
ttattatttc 550

<210> SEQ ID NO 95
<211> LENGTH: 568
<212> TYPE: DNA
<213> ORGANISM: Nezara viridula

<400> SEQUENCE: 95
gggggttata gaggcggcac tggttagctg tatcacgttg ttatccactt tattttttta 60
cagataggaa aaaagaattt tgatagtgtg taatatttat cgagaaaaat ggctcaaagc 120
aagttgaatg atttagccgg acgttttagt caaaaacccca aaggtgtcgg attaggttta 180
aaactattag cttttgccgg tgctacagct tatggagtaa gtcaatctat gtatactgtt 240
gaaggtggtc accgagcaat catatttagt aggcttagtg gagttcagaa agaagtctac 300
tccgagggtc ttcactttag gataccttgg tttcagtatc cagttgttta cgatatcaga 360

```
tcaagaccaa ggaaaatttc atcacctact ggatccaagg atttgcagat ggttaatatt    420

tccctcaggg tactgtctag accagactcg attaagttgc cttttgtgta caggcaactt    480

ggtttagatt atgatgagaa agttctacca tcaatttgta atgaagttct caaatcggtt    540

gttgctaaat tcaatgcttc tcaactga                                       568


<210> SEQ ID NO 96
<211> LENGTH: 544
<212> TYPE: DNA
<213> ORGANISM: Nezara viridula

<400> SEQUENCE: 96

gggggatata tttgatagtg ggaagagggt ttcgttattg aaataatgaa atgttcacta     60

ttttaatcgt gtagttcatc ttattttaaa atggcatttt ctttattacc aagaagattc    120

ttgaagtttc tctggaatga agaaagtgtt agaaggatat ctgttagctc tgtgaggttt    180

aatgaagatg aatctaacaa aaaatcatca gctgctgata agttacattc acttttacag    240

gatattatta aggatgaaac actaattaaa gaaaatatag taaaggcaac tgctgagcct    300

gttattgtgc cggtaaaaaa gaaacgtcct gagaaaccaa agaatttggg tgaaaaaatt    360

gttgattcgg caaaagaagt tgccaaaggt ttagaaggaa agcctgaaga aacagaagcg    420

caacttcttc atcgggtact tttaaaaaac aagcctctta cagaaagtgt tacaaaagct    480

gctgcaaacg atacattgaa ggagcttctt tcaggaatgg atgttgaaag aactccaaca    540

gtac                                                                 544


<210> SEQ ID NO 97
<211> LENGTH: 115
<212> TYPE: DNA
<213> ORGANISM: Nezara viridula

<400> SEQUENCE: 97

gggcgagtgt gaagaaaaag acatagactt tgttaaaact tctgatagcg gaatagataa     60

agaatatgac ctaccttccc ttccaacatt ggtttattac agaaacaaat tcagg         115


<210> SEQ ID NO 98
<211> LENGTH: 344
<212> TYPE: DNA
<213> ORGANISM: Nezara viridula

<400> SEQUENCE: 98

ggggagactc ggtgccaggc gtgttgttat aaacttttta gtccgtgtat agtgaagtgt     60

gtaggcatat caatacatat tttatgttat ttatagttat tagtacttaa aattttacca    120

agagagtgat agtacctata aatttcgttt caccatgtct aagcgtaaca cagaagatga    180

taaaccaatt cctgatattg tttttgattc caattcgaag actacttaca aaaagggaca    240

gtttttagga aagggtggtt ttgctaaatg ctatgaatta agagaagtaa ctaccaatgg    300

aatatttgct gggaagattg tatccaaacg acttcttacc aatc                     344


<210> SEQ ID NO 99
<211> LENGTH: 359
<212> TYPE: DNA
<213> ORGANISM: Nezara viridula

<400> SEQUENCE: 99

gggggtagta cgagatttca cgtgaagtta ttttcaggct taaaattttt actcccggtt     60

atatcttaaa cgatgtgata tagatgtaat gtcaattatt ttggtttcag atttagattt    120
```

agtattcaaa ttataggtga ttcgaatgtt attgaaaaaa gtggtgataa aggaacatat 180
agttgagggg cagtgtcggc acggtgttat tgagttttgt gttcagtcgt atttatatag 240
cccgggtgta atgtatcatt catacaattt tcagttcgcg gaaatgtttt aacctgtagt 300
tgtgtatact gatttctatg tgctttttaac tgttgtaaat tagaacttag gagtgtgta 359

<210> SEQ ID NO 100
<211> LENGTH: 640
<212> TYPE: DNA
<213> ORGANISM: Nezara viridula
<220> FEATURE:
<221> NAME/KEY: misc_feature
<222> LOCATION: 577
<223> OTHER INFORMATION: n = A,T,C or G

<400> SEQUENCE: 100
ggggagtgtc agtgtagtgt agtgtcgtga tcgggcttca tcatcatcaa caacactacc 60
acgcctgcgc atcattagcc tgcgcatcac ataataaccg acgcggaggc tggtcagaag 120
aagaggggag gaggtgcgac ttgaactggc ggaggcgtca ggagctcata cccagggcca 180
agttgagaca gccttctccg gaatattcca agtggggcga ttcaggaaag ccagtaagac 240
acacagttag tttttgtggc aaaattggac cgcagtcgtc atcaaaccag tgtcagaaac 300
agccggcaca aaggcacggt gatcgacaaa aggagaaaga acgattttgc accctgagaa 360
gggagccacg aagggagagg atggatcgga tgtatgacag caccgagagc ggctacgatg 420
gaggctccca agagaacatt cttgatgagc cacactatga atccatcaaa aatatcaaca 480
taaaaccgga aattcaaaaa gaacatattt acgaaagaat gaatggaaaa aaaaagaaaa 540
agaaacaaca gaatctcaaa ataataaaac agagganagt gaaaaaaagt aggccgaaaa 600
ataaatacga cgagacaaaa acggtaccaa atgggaataa 640

<210> SEQ ID NO 101
<211> LENGTH: 680
<212> TYPE: DNA
<213> ORGANISM: Nezara viridula

<400> SEQUENCE: 101
ggggactggg atgaaacctt tcatggaggt gcaatttgta ttttgtttga ttgtgcttgt 60
tgattaaacg tcatttcttt acgatatgaa taaaagaaaa agagaagata gtatgtcgga 120
agactgtatg atggaagttc aggttagtaa aaatgcctgt tcaagttcag gagagtcagt 180
tatgcctcag tgtttaagga tgttggatga aataatgagg agtggaccag ctgaattagt 240
tgaacgtagc ttaaaccctc ttggtgcttc tccattggga aatcatgtga aacgtgttac 300
aggatatgaa atagcagaat tagatgaatt tacagcaacg gttgactcaa ggcttaaaca 360
aaccgttatg actaaaataa ttactatatc tgatcaaatg aaatttcttc gtcaacagct 420
agtaaacgct gtccaagatg cacaagaaag ttcggcctta aaccatacac catgcaattt 480
ccgcaaagtg cctggaaatg tatattatct gtatcagaga ccttctggcc agaactattt 540
ttccttattg tctcctgcag attggaacga aaaaccaccc caccagttct gtggttcata 600
tctttatgag catgattata catggaaaaa aatatgaatc ttgacttgtt tcttttaata 660
tgaataattt taataaaaaa 680

<210> SEQ ID NO 102
<211> LENGTH: 610
<212> TYPE: DNA

<213> ORGANISM: Nezara viridula
<220> FEATURE:
<221> NAME/KEY: misc_feature
<222> LOCATION: 38
<223> OTHER INFORMATION: n = A,T,C or G

<400> SEQUENCE: 102

```
gggggtatta atgtggagat attttatttc aaaagagntc tgtttgttta tgttcagtga     60
tttgagaagt aatacaggtt tgattccatt ctatttttct ttttttttct ttaatatttt    120
aattgaaggt ctgaaaaaaa gtgttgtgta tctgtgtgtg ttggaataaa atgtcttcat    180
aagttcctca aattttaaaa ttattttatt cttgtatgtt cctatattct tcttggaaaa    240
tattatcaaa taaataagaa attgatcttt caactccatt gttatttaag actacgatac    300
agccctggaa tgtaattata gattctttca attttttttt gttttttcct tggttgaatt    360
aatgatgctg tgatagtttg tctaacttcc cttttcttca cctatgatta ttatatgtga    420
ttaaaaaagt taccttgatt tagcctaatt ctatttgtat agatataaat atgttattaa    480
tgtgaattat tgaattgatt tcttaatcat taaaatgatt atgtgcaata atattgtatc    540
tgagattttc ttctaatggt aagtttattg atcacctggt ttacccgtag aacatagaat    600
atagtagatt                                                           610
```

<210> SEQ ID NO 103
<211> LENGTH: 272
<212> TYPE: DNA
<213> ORGANISM: Nezara viridula

<400> SEQUENCE: 103

```
gggtattaat ttttatttgt ttatccataa attagctctt ttaaaccaat tactttgatt     60
ttttcttgat agttatcatg ttagcgactt cattaacatt cactaatcag gaaagacagt    120
ttacgaaatc tgtatctaga ttgaagaaat tccgtatgat ttttaataca ttgaaaaaat    180
atggccatta atcgaattag aaaaacgttt ttctactaca acaataggcg cagactttcc    240
atttcgcttt gggagagggg aggtgaagaa cc                                  272
```

<210> SEQ ID NO 104
<211> LENGTH: 618
<212> TYPE: DNA
<213> ORGANISM: Nezara viridula

<400> SEQUENCE: 104

```
ggggacaggc catgttgatc atgaaggctg tcgctgtgat tcttcttgtc gtcttggccg     60
cgtcttgtca tgctttctca atcagtggct tcttcggatc tgtctcaaac cacgccaagg    120
aaaatatcga gcaaaagaaa acccaggtca caaacaacat cgatctcatg catggacaca    180
tgaaggactt caagcaggct tcacttaatg gtgacgtcct tggggctgtt cagttgtcat    240
ccaagaactc agtgaacatg gcaaaaacta tggctgagca agcaatacaa aatactgtta    300
aatacgctca tgatgcagtt gaagacctaa agtatctaat tcccttcaaa ccgtcaaaga    360
aaccacctag catgggcaaa gtacctaaac caacaacagg accaccaaaa tattccattg    420
tttctgaaaa taataataaa ccaacaaaag gaaaaggaac tcctgcttca cacaaaactt    480
tggaatggaa agccggtttt aattccaaag ttacgataag taccgaagga acgattaatg    540
caactagagt acctcctgaa caaaaaatgc ctaatccttc aaaagaatca acagctaaac    600
tagaaatgtc tcttacta                                                  618
```

<210> SEQ ID NO 105
<211> LENGTH: 675
<212> TYPE: DNA
<213> ORGANISM: Nezara viridula
<220> FEATURE:
<221> NAME/KEY: misc_feature
<222> LOCATION: 483
<223> OTHER INFORMATION: n = A,T,C or G

<400> SEQUENCE: 105

```
ggggaagtat gttttctgta gtgaaccaat gtagttaacg ttcaagagtg ttagttttaa     60

aatagcagtt aggattttct tttttctttc tttttttgt atggaaatga gatttcatcg    120

aagaagacac ttccaaatca actttattgg ttcttgacaa atccagtgta tatctttaaa    180

actgattttc atgtcaagcc tcaaaacact ttcacttcat tgtaaccaaa aagtaaggcc    240

cagtttgaga tggtttaaat ggcctttcaa gttcaagaaa caactagtga agaagagcgg    300

ataaagattg attgggaaac aactgaaaaa gatattttgt ctcaaccgtc tgctgttgaa    360

attgaagtaa atgaaaatct caacagcaac ttaaataaca gtcataaagt tgttgactac    420

agtaaaccga ttgttgataa catctcaaat cacactgaga ggttctttct tgttggtgaa    480

gantcaacat gtgttggaaa gaaaggcgac gaaaatgggg tatgtaatgg agtttatttt    540

cagaatgtta ataccaatga agtagatgat ccaggtgaga caaatgattg tgttcagtta    600

aatccaataa aggacacatt cactaatatg aaacttccat ctgtgccagt aaaagaaaat    660

aaggattgta ccatt                                                     675
```

<210> SEQ ID NO 106
<211> LENGTH: 653
<212> TYPE: DNA
<213> ORGANISM: Nezara viridula

<400> SEQUENCE: 106

```
ggggaatgtg tgtttactac cgccagttgc ttgtgttgaa cttgaatttg tatgtcattt     60

ttttagtatg aattatggag gtaacttcaa ttggaaatga agaaatacaa ttagctggta    120

atctgaaata tgttcagttt aagtctgact taaagaactt aatagaaagg gaaattctag    180

cagatgggtg gcaatcctcc gctgaagcat ttgataaaat cttccccaag aaaaggtact    240

tgcctagttt caagaaggca tttcatggtg ctattttagc tggttttgaa gaaagtctag    300

atgaaatgtt gggagatgtt ttgcctaaac agtgggatat tttatatcaa gaaaaatatg    360

acaatcatca tgatgggaag gatacttctc ggctgactta tagtaaaatg gcattaaatg    420

atttgaaatt aaaacaaaaa gctgctgtag aatctgttat agaattaaaa ctgaaaaaaa    480

ttgaagaaat taaacaaagt atatatatta agaaattaga agtaataaag aaatcatctg    540

aattgcaagc cattaaacaa aaatggaaaa aaaactgtgg aatattagaa gacttgaaaa    600

aaatgagttt ctaagttaca ttaccaatac atgagaacct atttatttat ata          653
```

<210> SEQ ID NO 107
<211> LENGTH: 398
<212> TYPE: DNA
<213> ORGANISM: Nezara viridula
<220> FEATURE:
<221> NAME/KEY: misc_feature
<222> LOCATION: 176
<223> OTHER INFORMATION: n = A,T,C or G

<400> SEQUENCE: 107

```
ggggactcta gttagtgact aagtttaata ttttattaaa atgaccaaga aaaggaggaa     60
```

```
tggaggaaga tccaaacatg gtaggggtca cgtgcaagca gtccgttgca ccaactgtgc    120

ccgttgcgtg ccaaaagata aggctatcaa gaaattcgtt attcgtaata tcgtanaagc    180

tgcagctgtg agggatatca cagatgctag cgtttactct tcgtaccagt tgccgaagct    240

ctatgccaaa ctacattatt gtgtgtcatg tgctatccac tctaaagtag tgcgtaatcg    300

ttctaaggct gagagaagaa ttaggacacc tcctcagcgt aacttcccaa gggatatgat    360

gcgtcaaggt ggaccccaga taaggaagta atcttttc                            398


<210> SEQ ID NO 108
<211> LENGTH: 607
<212> TYPE: DNA
<213> ORGANISM: Nezara viridula
<220> FEATURE:
<221> NAME/KEY: misc_feature
<222> LOCATION: 455
<223> OTHER INFORMATION: n = A,T,C or G

<400> SEQUENCE: 108

ggggaatgtt gtggtgtgct gacatagata ttagtccatt tgatttggaa atttactctg     60

atttagctat aggagcaggt acgggtagta gtgcagcatt ttctgtctgt gttgctgcag    120

ctgtatataa ttatattagg ttaaaagcat ttcaaaagtt tggctgtggt gaatttaata    180

tttccagcag tccattcaag cctcatatga tggaattatc tcagcattat aatggatttt    240

ctccaaagga taaagacata gtgaataaat gggcattttg tgtggaaaaa attaatcatt    300

ccactccttc gggtattgat aacactattt gtacctttgg aaatgccgtt ttaatgaatg    360

ctgctggtga aaaagatgaa aaacgttcta tagaactatt agataatctt ccagccttcc    420

gggtgctgat agttaattca ggtgtaccaa gatcnactgc tgacatggta aagaaagttt    480

caaccttgct tgaaatttgt cctgaaagca actcaatcca tttcttgaat caatggatgt    540

aatcgctatg aaatttcttg aatatgctca agaaataaaa aaagcaactg aaaaattgga    600

tgttttg                                                              607


<210> SEQ ID NO 109
<211> LENGTH: 53
<212> TYPE: DNA
<213> ORGANISM: Nezara viridula

<400> SEQUENCE: 109

ggggttcggt atcggtttcg ctggaaagat gaccgaactt gatcatttag agc            53


<210> SEQ ID NO 110
<211> LENGTH: 652
<212> TYPE: DNA
<213> ORGANISM: Nezara viridula
<220> FEATURE:
<221> NAME/KEY: misc_feature
<222> LOCATION: 399
<223> OTHER INFORMATION: n = A,T,C or G

<400> SEQUENCE: 110

ggggagttat catctctcca cagcccgcgg cactacagtt ccccgcttaa cagttctcta     60

taggatcaga ggtggtgcgc tctatctgtc gacccgcgca tgctgtactc gtccctcttc    120

ggggcctttc ttcttcgaac tcgccggctg gaaggtcctc gctcctcgct ccgtacagga    180

tctctttagt ctctcttaaa acaatcaagt gttttttatt agtgttccat aatgagtgat    240

acagcagctg aaaccaagga aactcaggct gcaagctcac ctgagaagaa ggaggtggtg    300

tgcgagcgaa agccagcagc tgctgctgaa aaagaaacca aggaagaaaa gaagacagaa    360
```

```
gataaaccag aaacaaatgg acacagcaaa accgaagant ctaccgaaga aaaacctgta    420

gaaaatggag atgcaactga tgtgtgctca ttgccacaga agaggaaatc tgaagttggt    480

agtggggaat ccactgagaa gtcagctgaa ggtgcaagtc ctgaaaagaa ggctaaacta    540

gaagagaaag ttgaaaatgg tgaagctgaa gcaaaagctt aaaaccattt aattcaaatt    600

aatctagact gttatacagt gttatgttta caaaatgcag catttgtaat at            652


<210> SEQ ID NO 111
<211> LENGTH: 575
<212> TYPE: DNA
<213> ORGANISM: Nezara viridula

<400> SEQUENCE: 111

ggggacgctt tatctcattg gtacttggaa gtcacgtttc tcgtaaacct tctcttatag     60

gttatattta tttcttacag ttctgttcaa actaattctt tcagatatga aacctttaat    120

gttacacggc catgaaaggg ccatcaccca aatcaagtac aatagagaag ggacttatt     180

attctcttca gccaaagatc actgtcctaa tgtttggtat tctcttaatg gcgaaaggct    240

aggtaacttc attggacata ttggtgctgt atggtgtctt gacatcaact gggaaagcac    300

taagtttatg tctggtgttg ctgataacac cctaaaatta tgggactgtt ctaatggtgt    360

agagattgga aatattaaca ccaaatcaac tgtgaggaca tgtgtcttca gttattcagg    420

caacttggct gcttattcca ctgatactca gaggaaacaa atttgtgaaa tcaatgtaat    480

tgactgtagg attagtgact cgtttggttc cgaaccaata ctgtgtatac cagtaccaga    540

gtcaaaggtg acggcattat tttggggccc tctgg                               575


<210> SEQ ID NO 112
<211> LENGTH: 169
<212> TYPE: DNA
<213> ORGANISM: Nezara viridula

<400> SEQUENCE: 112

ggggctgcct attaaagata atttatggct taatttacac cttcccttag ggaaaatact     60

aggtcaagtt cttgtttaat ggtgatcatt ttacctgtgt tcagttgatc acttaaaaaa    120

aagagtttat ttattaattt tttatcctga ttatagccga gtgttatac                169


<210> SEQ ID NO 113
<211> LENGTH: 636
<212> TYPE: DNA
<213> ORGANISM: Nezara viridula

<400> SEQUENCE: 113

gggggataga aacattcttc aagttcaaag tgagaaagaa aggcaagaaa gtaaagaagc     60

agtaggcgct cggctaatca ggaggttgag tatgcggccc acgcaagaag aattggaaga    120

gaggaatatt ttaaaaaaac aaacagctgc tgaagaaaag aagctcaaag aagaaaagaa    180

gcgtatgctg ctgcgaaaac tcagttttag gccaactgtt gaagaactga aggaaaagaa    240

gatcatacgc ttcaatgact acatagaagt gacccaggct catgactacg atcggcgcgc    300

agacaagcca tggactcgac tgacaccaaa agataaggct gccatccgaa aggaactcaa    360

cgaatttaag tcctctgaaa tggaggtcca ccaagaaagt agacatctta ctaggtttca    420

taggccatga catttggcag caaaagccgt gtctagttgt acagtgttat ctaccatgct    480

attgtatata ccacagtcgc taagctacct gcaccgtatt agagcctcga caaatttttt    540
```

```
tactgtttgt aactttgttt gtatatattt tatatatata tgaaaatata taaataatat    600

aacatatggt accattccat aattagggat ggttaa                              636


<210> SEQ ID NO 114
<211> LENGTH: 450
<212> TYPE: DNA
<213> ORGANISM: Nezara viridula
<220> FEATURE:
<221> NAME/KEY: misc_feature
<222> LOCATION: 414
<223> OTHER INFORMATION: n = A,T,C or G

<400> SEQUENCE: 114

gggcagactg agattttatt tatatttatc ttatgcagta tacaattcga gggtgagagc     60

aattacagtt tttcataaaa ataaaaaaaa caaacaaaaa taacttgtca ttttgatgat    120

ccaataaaaa taacttagta aatatcattt ttatggtatg aatttaaaaa atgtattaat    180

tgtaaaatat ttaatttgtc aattcactta atagaaatac ttggatccat ttttatttgt    240

cagctttcac cagtgctgta atgttataaa tgtgatctgt tcaaaggaga tttccattgg    300

aaatgtatta ttattttttt atttttcttt cttttttttg tttaatttac agcatgtatg    360

ttgctgtcaa tataaattgc cgttgttcga aaccttcaaa gtcttgatgt agcnacaatt    420

ttttattaat aaaattggat ttgaaaatct                                     450


<210> SEQ ID NO 115
<211> LENGTH: 467
<212> TYPE: DNA
<213> ORGANISM: Nezara viridula

<400> SEQUENCE: 115

gggcaccaat cttacccatt cacatctcgt tagcaagcag ccaccaccac aatgccaaca     60

ctgcaataat acacttacag ccagtcacaa gttacaggaa tgttattttt acatatcaaa    120

tctaaatagt gtaggactta cacctataat atcaaacatt ttaagttatg acgaagacag    180

tataatgtta gtgttagatt tcttaaaatc aaacaatttg ttaaataaaa tttaaaattg    240

atgcagagac cgttgatata atatgagaag gagttgatcg gggggtgcgg tcaaattaat    300

actaaattaa actattatta ttaaaaaaca ctttattcag aaatattaca atttgtcaca    360

gttaaggaca cttataatag agttcagaga ttgcattcat accgtatata caaaaatata    420

aataaataaa gtaataacaa aagaataaga agaaagaaca aaagagc                  467


<210> SEQ ID NO 116
<211> LENGTH: 363
<212> TYPE: DNA
<213> ORGANISM: Nezara viridula

<400> SEQUENCE: 116

ggggatccat aggatccgca taacacttac ttctaaaaac atgaagtcgt tagagaaagt     60

gtgtgctgat ctaataaatg gagctaagaa ggaaaatctc cgtgtcaagg gacccatcag    120

gatgcccatc aaaattctga ggattacgac tcgtaaaacc ccttgcggag aaggttctaa    180

gacttgggat cgattccaaa tgaggatcca caagagggtt atcgatcttc attctccttc    240

tgaagttgtg aaacagataa cttcaatttc tcttgaacct ggtgttgaag tggaagtcac    300

cattgccgaa taattacttt gtttttatta tgtgataatt atataaaaaa aattatataa    360

tag                                                                  363
```

<210> SEQ ID NO 117
<211> LENGTH: 632
<212> TYPE: DNA
<213> ORGANISM: Nezara viridula

<400> SEQUENCE: 117

```
gggcagaggg aaagttaaaa gtatttagaa aatgccacta tcacttagtg tacatagata     60

aactagggtt acataggttc ttgatagaat tgaatttatt actatggtat aaccctcttg    120

taaactttca tatcaaactg ttttaccagt gcatacacca cacctcactt cacttataaa    180

taagtagcta tttaaaaaaa aaaatgtttt tattatttta taattttccc ttctgatagt    240

tttactgtca tataacatgt attaaaacat aaaatctcct tattttctat tcctataaaa    300

aaaagaaaaa aaaaaagaaa ttgtaaataa gaaggatgca tttgttcatt ccatttatta    360

gttgttaatc aggtgctatt tcagttttta ttttagaagc attagtttac ggatgttgta    420

tttctcattt tagctcttat gtgtcatact gctggttgtt ctcccataaa aatctaactg    480

tgcatttaaa ttaatcataa tagctatggc taaggccttt taaatttaaa caaaagataa    540

gttaagtgta ttatgtaata tgtattgtag aagaagcatg aatatcttat aagagaacaa    600

taaattattt tattttaata tagtttactt tc                                 632
```

<210> SEQ ID NO 118
<211> LENGTH: 690
<212> TYPE: DNA
<213> ORGANISM: Nezara viridula
<220> FEATURE:
<221> NAME/KEY: misc_feature
<222> LOCATION: 627
<223> OTHER INFORMATION: n = A,T,C or G

<400> SEQUENCE: 118

```
gggtgttgat gagtggctga cggtgatgaa gttctcaatc cctgttgtac tgctagatga     60

gacattgaag tttgttgcaa ggaagatcgc cgatgttcaa ccttcaatcc agataagata    120

ctgagaggga ccaccaagac attcaaaaga gggtttatgt gcttctagta gaataaataa    180

aatgcctata tttaaaatct cataggatga tcacaaattg tataaaagag gtgtatagaa    240

cccatttgtc ctattacgcg gagaaatgtc atttcctatc tagtctattt tggttctcga    300

tttttaacct attagaatta tattttttat aattttttttg attattttat tagatttttt    360

ttatatatac acatcctttt tcaacataca acgcctctaa ccaataacat ttttattaga    420

ttcttataaa ccgtcacatt tgatggaacc caacagctgg ctgaagggtg tctattcttt    480

aatactaaca tgtcgcgtga ttttcattca cctctcatta tacctgtaca ttctcaatta    540

atattaattt aatcttcatc taatattact ttacattctg tggtcttcct tttttataaa    600

agattatatc aaaatttcac tagtagncta taaatatttt atttattttc tgttgtatat    660

atgaaaatac tgtacattca cttatgtatc                                    690
```

<210> SEQ ID NO 119
<211> LENGTH: 690
<212> TYPE: DNA
<213> ORGANISM: Nezara viridula

<400> SEQUENCE: 119

```
ggggaagtta taagttgtta cagtatccaa agattctctt actatgtatg tttacgattt     60

gccatacaat gaaagaaagc aaatttgcag aattttggat ttgaataaag cttgggagca    120

attaggtgga agttacatga aatttgatgt gacaacttta aagcattttg aggaagcacc    180
```

```
ttcaagaaat cactctccaa ctgatgaatt attaacttca tggggtactc ggaatcataa    240

tgttttggaa ctgttcgtat tgctttctaa aatgcagcac tatcaggcta tgaatgtact    300

caaagatttt gttgatgtaa agtatcatcg gctcatatat gaaggagaag aaaatttgtc    360

taagatattg gaggataaag gaaatccttt tggtcaaaat accagtgcat cagtcgggaa    420

ttataaaaaa gaggaagtaa atggaaactt aaatattaat cgaaaaggac aagacattcc    480

acctgataag gatatgcaga aaaataaaat gtttataaat gagaaaatag ttaacaaaaa    540

agaaactgat cttggtgtcg aaggcctttt gagaatggaa aatggacagt ctaaattgga    600

tgaaaatact cgtgatagtt cgagtctatt gatttcatat gctgaactag aacgagctac    660

tggttcttgg gacaaaaaga atattttagg                                     690
```

<210> SEQ ID NO 120
<211> LENGTH: 250
<212> TYPE: DNA
<213> ORGANISM: Nezara viridula

<400> SEQUENCE: 120

```
gggacatgtg ttattgtttc acaagattca attatccttc ttcgtaagga ataaaggtca     60

ttgactggtc tcgcatagac tatgtaacta cataactata taatggtata gttattgatt    120

agttatttat tatttactct tacttcagtg gggaacgttg aacattagag acagattaat    180

gtttgaggca ccttagaaaa taaaaataaa gctaagacaa tttttgagta aaaacataaa    240

cgttttaaag                                                           250
```

<210> SEQ ID NO 121
<211> LENGTH: 138
<212> TYPE: DNA
<213> ORGANISM: Nezara viridula

<400> SEQUENCE: 121

```
gggcaaaggg aacaattaca aaaacaagaa cccttaccat cagtagctac agaatgtgat     60

agccaccaac catttttgat ggattcaact atgttaatcc ctagtgaagt caagtctgaa    120

aagaagaaag atgatccg                                                  138
```

<210> SEQ ID NO 122
<211> LENGTH: 363
<212> TYPE: DNA
<213> ORGANISM: Nezara viridula
<220> FEATURE:
<221> NAME/KEY: misc_feature
<222> LOCATION: 65, 243, 340
<223> OTHER INFORMATION: n = A,T,C or G

<400> SEQUENCE: 122

```
aaataccggt tttgagactg gtttttcaac cgtcataacc tacattattt gcctcttaca     60

ttgangcaag gactaacaat tttttttca tcgaacaatt tttgaaagat ttcttataaa    120

taaaacattt ctttttatat tttcactgtt actacttctt tgactagtga gttaaatata    180

acatatttaa aacatcagtg gattctccaa aaattttatt aatcagcttt tttatacaat    240

gcngtatcag tatgtttaaa ataattctac atttaatact tttatggtat accataacta    300

cggcttcaaa atataagttg atacggaaaa gcgattggtn attaaaaaaa aaactttata    360

aac                                                                  363
```

<210> SEQ ID NO 123
<211> LENGTH: 547

<212> TYPE: DNA
<213> ORGANISM: Nezara viridula

<400> SEQUENCE: 123

```
gggggagtgc aagatgtggg tctccactac ttttctcgtg gtagcttttt ttcacgcctc     60
tgtgtctcag tactttaacg atgctgagga acaacggaat ttcgcgaaag aggaagttga    120
ccgagatgac gatggtgtta tcgtagtgat aaacgacgat cctgaaccaa atgacggatg    180
gaaacccgat gaggaagatc ctcttcaagc tggacctccg ccggagtata tgaacatgca    240
agcaccacct tcggactact tggaagaaca aagaccacca caggactatt tcgaagtgca    300
aagaccagag ccggattact tggaattgca aggaccatca ccatttgaat atgtttaagg    360
taaaattgaa gaagaaaact tcaacaagaa tgtaaataag aacttaagtg ctggaagtaa    420
ttgtttttc ttgatctccg ccatctactg agacttcaca cccaccgtta tgattcttca    480
tgttttacaa tttttcccc atcacctcca atttgtcttt ccttaataaa caagttatac    540
attgtag                                                               547
```

<210> SEQ ID NO 124
<211> LENGTH: 575
<212> TYPE: DNA
<213> ORGANISM: Nezara viridula
<220> FEATURE:
<221> NAME/KEY: misc_feature
<222> LOCATION: 470
<223> OTHER INFORMATION: n = A,T,C or G

<400> SEQUENCE: 124

```
ggggagttga gcataatgaa gtctctttca gtttgctttc tggctgtact gctaatacaa     60
gcatcgtcag gcagacctaa tgatgacagt ggtgagtacg aagaacatga agagcattca    120
ttcgtttaca gctcaactaa tcctggtcgg gtacagagca cgcaaacaat cataggaaga    180
ccaccctttc agccaatgag ctttggcttc ggcaacccag ggcggcagaa cttcgggaat    240
atgttcggca ccggaggatt cggcggtttc cccagtttta gacccttacc aggcttccca    300
cctcttggac aaatgagccc aggtggtttc ggcggagtaa caggacagtc tttccagcta    360
caacacccag gaggatttgg acagatcagt ggattcactg gtccatcatc cgcaggaaat    420
gctgcctttg ctagttctag ttccggaagc ccaggtggtt cgaatagccn actaatcata    480
aaaccaggag gaggcttagc attcgcaagt tcgagctcaa gtagcccagg aagtaaccaa    540
gtttcaatca gtacgcagac ctcgagttcg acaga                                575
```

<210> SEQ ID NO 125
<211> LENGTH: 482
<212> TYPE: DNA
<213> ORGANISM: Nezara viridula

<400> SEQUENCE: 125

```
gggggcacct catcaccagc tattttagca tctgtttatg taatagaaaa attaattttt     60
tgagaaaaaa tcctctgaca ttattgataa cataacatcg caaattataa taaatattaa    120
agtaaatgag tgagtaaata tttacatcac tttagaattc gattgaatcg gacttacaaa    180
gttttggaaa taagccattg gtatactaaa acaattgagg ggtcaagtag ataaagagaa    240
gaagtaatat ttctgaattc ttaggaaaat gaattcaaat gactttcatc tattacaaga    300
tcaatgttta ttggcgatgg accaaatttg aagatggaaa gaagaaatat taatgatatc    360
aaacttgtaa aattttacca taaagtttgc cattatccat aattcaattt ttcctaaaaa    420
```

tgcactcatt cccataaccc atcaattatt gttaaattga agggcaaaaa aactactttt 480
tt 482

<210> SEQ ID NO 126
<211> LENGTH: 535
<212> TYPE: DNA
<213> ORGANISM: Nezara viridula

<400> SEQUENCE: 126
gggataagag agtgcaacaa gttctggtaa ggttaaatgt agtaacttca tgtactaact 60
taaaacagta caactttaga tgttaggtgt taaatgttgt agtcaattct atgattttct 120
acaggaattc gtacaattta aaaattattc tatgaattaa ttctaaaata aaaagtcgat 180
tttttcatag aggaactgat ttcaaaaggg ttgccataac acaagtttat ttattttacc 240
cataaatagc aagggaaata gctaaacatg gattattttt aagaattgca aatattttta 300
ttatgactgt agatttatta taacttttaa tttttaaaat aattatctag tctatatact 360
ccattagaat aagttgtctt tgtgatgtaa aactaatttt aagaataggt ttatgtcaat 420
aaggatgtac ttacgttata ttagtaggta ttgaatataa tagattctgt ataattacct 480
aatagaataa gttcagtgct attgtatctg ttaacaataa atgtgaattt attat 535

<210> SEQ ID NO 127
<211> LENGTH: 94
<212> TYPE: DNA
<213> ORGANISM: Nezara viridula

<400> SEQUENCE: 127
ggggttcatt gaactgttaa gtggtaaagt taatcatata acatatatta attcttattt 60
atattgtcat ttgtcttata cctctcgaat gttt 94

<210> SEQ ID NO 128
<211> LENGTH: 70
<212> TYPE: DNA
<213> ORGANISM: Nezara viridula

<400> SEQUENCE: 128
gggcatctat agaaatattc ttacttatca gaatcttacc tctaaatata aataaacaaa 60
gaagaagtgg 70

<210> SEQ ID NO 129
<211> LENGTH: 688
<212> TYPE: DNA
<213> ORGANISM: Nezara viridula

<400> SEQUENCE: 129
gggggactta tcaaacgttg atgaagacta attatactca cggattacat ctgtgagttg 60
acaaacatat atttgtcacc ctaatgtact taccacttta ttaggttttc taaacaactt 120
gaaaacaaat ttttctcttg ctttaactat gacattgttt caatttcgat ggctgcgtcg 180
acttataagg agtaatacca agcccattcc aatggataaa gcagagttat ggaaagaacg 240
tctttcagtt gcttatatgt ttgtttcatt aaatatcctt ggtactataa tttattttta 300
ttacaaagga aaacctgatt tagctgaata ttatggtctt aaaactgagg aagagataaa 360
caaaaaacca gcaatatatt atgcagagct cttaggaatt aaaaaaacac atgttataag 420
gtataaaggg tttcaaaaag tagaagaatt tgattatgaa aaaccagcag acagtgaaaa 480
agtgaaaact gatacagagt agaatttttg ttctttttat ttataattag tgttatattt 540

```
aaaaaaatgg taagccagtg tcaattgtaa atctctaaat acaataatac tgttagtaaa    600

ggacaattcc ataaataaat aaatgtatct atcaatacag atatttttat tatttttaca    660

tatatttgtt attaattgca ttaaataa                                       688


<210> SEQ ID NO 130
<211> LENGTH: 214
<212> TYPE: DNA
<213> ORGANISM: Nezara viridula

<400> SEQUENCE: 130

gggccaccat catacgatag acgtgtaatt tctggaggca gtggtccaga gtctaagcca     60

actaaggtca tacctgatga tgaaggtagt gatgatgatt ccatcgactg gggcagtggt    120

tcagagtcta gttcggaatc gagtgatgat gaaggacagt accaatcgat cagagaaaga    180

tttttgaaaa aaacaacaga tcgagaagaa gaag                                214


<210> SEQ ID NO 131
<211> LENGTH: 496
<212> TYPE: DNA
<213> ORGANISM: Nezara viridula

<400> SEQUENCE: 131

ggggaatgaa tgagaatcgt taagagctag tcaatccttt aactgttatg tttcatctca     60

agcaaatgaa ttccttgtac ttatgttcat tgttaccctc attaccacag gctacaggtg    120

atacaggaag taaactgcag tatactcact gtcgattgtg cagcttagaa gaaaattgcg    180

gtgttctttt gcccaaagag attaatgcaa cagttctcat ggaaccaatt gtgtttgaac    240

ttatgtatga attgacaagg tttcaggatg ttatcaatag ctgccaaaat gaattagagt    300

cttcttactt agtgaattat gtatttaaat tatgtaacac tgtgaatcgt tgtttaaaaa    360

atttgccagt aaagggacag ccttcagata ttgctgagca acgattgtta cttttccata    420

ctgctaaaac gtttctacat tcatcaatga agattcttgg tttacagcct cttaataaaa    480

tgtagatttt actcag                                                    496


<210> SEQ ID NO 132
<211> LENGTH: 632
<212> TYPE: DNA
<213> ORGANISM: Nezara viridula
<220> FEATURE:
<221> NAME/KEY: misc_feature
<222> LOCATION: 122
<223> OTHER INFORMATION: n = A,T,C or G

<400> SEQUENCE: 132

gggagatgtt cctttaatga aatggacagc ctttatgctc ggagagcaaa actgaatcgg     60

actgcaagag cacatatggc taatgaagca ggcgttactt aggcgtagga aaaaaaaaaa    120

anttattttc ttagattact ggtttaattt ctttaatagc tttttaatgt aggtactggc    180

aaatcgaaaa aaattgccaa gaggttagca gcacataaaa tgtggatgag actgaaagac    240

ttaccctgcg aaagcaacac cattcattac ggcttggatg atgaagatga ggtatgcgta    300

attaaattgt ttatctacta ttatcttttt ttaaaaatgc ttgatttaaa tttatgattg    360

attattagtt atacttgtgt agttaattac aaattaatta atatagtaat tagtttttta    420

ctgatttttt ctattttaat ttattttatt ggctcgattt aagttttata gctggctata    480

aaaaatacca agtttctata ctcagtaaga atatatttta tgggcattgg aaatccaggc    540
```

```
tattcccaaa ctcgttatga acctataaaa ggaattaaag gtattccttt attcatcatt    600

ggattgttga tagtttgctt ttgggatcaa tg                                  632


<210> SEQ ID NO 133
<211> LENGTH: 422
<212> TYPE: DNA
<213> ORGANISM: Nezara viridula

<400> SEQUENCE: 133

ggggattggt tgatgaaata ttctacctgt tgacagtatg gttggggtat tgctctgttt     60

tcatcagtaa ttttacgttt catctgcaaa atagttttta tttgcataag aaatgaacat    120

cgaacataaa atgaaactct tttgctgtt gttattccct tctctatgtg cctctcattt    180

ttgtccatcg aggcattact ggagtaaagc tcatagtaaa tgcttggaat gtaaacagtg    240

ccatgtaaca cttattcctt gtacagctaa gatgaattca atttgtgcca atatccatga    300

aaaaaatcac cacttccaaa aatatcgtat tcaatttttt gatgatggga atgaagatga    360

gcttgacaaa caagtagatt ctacagggca catacacaaa gatgatctgt atcttccaca    420

tg                                                                   422


<210> SEQ ID NO 134
<211> LENGTH: 134
<212> TYPE: DNA
<213> ORGANISM: Nezara viridula

<400> SEQUENCE: 134

gggcccctga tgtcgatata atccgaaaag ttacaaaaag tcaggcaact ggaacactat     60

ctcaaatttg atatcatttt cataaaaagc gcccccccaa aacatcatag tcgaccctga    120

tatcgattta atcc                                                      134


<210> SEQ ID NO 135
<211> LENGTH: 68
<212> TYPE: DNA
<213> ORGANISM: Nezara viridula

<400> SEQUENCE: 135

ggggggagg tacgatgtgt ccctgtgtca tgtactgtac atcgattctg tgtacaacaa     60

taaaatac                                                              68


<210> SEQ ID NO 136
<211> LENGTH: 82
<212> TYPE: DNA
<213> ORGANISM: Nezara viridula

<400> SEQUENCE: 136

tatataaaac ctgcaaatga aattaaacca gaagaatttc gattactaga tgtagataat     60

cgtacagtat taccaataaa ta                                              82


<210> SEQ ID NO 137
<211> LENGTH: 691
<212> TYPE: DNA
<213> ORGANISM: Nezara viridula
<220> FEATURE:
<221> NAME/KEY: misc_feature
<222> LOCATION: 532
<223> OTHER INFORMATION: n = A,T,C or G

<400> SEQUENCE: 137

ggggtaattt aggtaaaaat cagtaagaat aaatgcattg attcacttat ttgaaaatta     60
```

```
aataagaatt aaataaactt ttgaaataga acaattcaat cgttgccctt taagtaagat    120

aagcggttcc atattcgttt gtaagaacaa aggaattgat agattagctg tcaaagctta    180

tagatcgatt gagatgtatc ttccaactct taaggtgatg acttattcaa agttttttct    240

tacagaaagt aatgaagctt ttcaaattta attaaaactt ttttctcttc agatagtcaa    300

tataaaaagt ccataacaat caatttataa tatagaggta tatcttcata cccaatcgta    360

atttattctt cccttttttt tattattatt tacaggcttt gctgaccttt tatttctttt    420

attattttat attatatttc tattatagtt taataaatta tttatttatg aatagatgta    480

cgagcttgta aagttttaag taggcttttg attaaacata ccatacaatg gnacgaaatt    540

tttaataagc tacaaaacaa agcaaaaaga tgaatgaaat aagttgaaaa aagtcctgga    600

atgtcctaaa cgaatattag taaaaatttt acatttatca tgtatgtaag attgcatgtg    660

cttgtagcat gtgttagaaa taaattattt c                                  691
```

```
<210> SEQ ID NO 138
<211> LENGTH: 172
<212> TYPE: DNA
<213> ORGANISM: Nezara viridula

<400> SEQUENCE: 138

ggggcattca agtcctgtaa agttacatca acagggacaa gatctaaatg atataaaaac     60

cacttaatta taaatccata cactaagttt aatcaaaatc gttggagcca ttttgaaaaa    120

atcttaaaaa tgtttttaat cgattctgtt aagtgtcatt tcagattatc cc            172
```

```
<210> SEQ ID NO 139
<211> LENGTH: 645
<212> TYPE: DNA
<213> ORGANISM: Nezara viridula

<400> SEQUENCE: 139

gggtgtattc atatataatt tttcaatttc aaaaattggg tgtttgttgg atggttcaac     60

tttattaata ttgaaaaaca aaattggcgc ataaagctag ttgatcttcc aaaaatatgg    120

aacctaggtt tcagtaatag gatttggtgt cattaagttg tatcaattga tgcattttac    180

ccatctctaa aatattaaca taaaaattcc aatagataca tactattgct ttagaaatat    240

atttaaacat attaaatgtg ataatatttt cttaatatat gttttttttt tctttcttgt    300

tttattcatg cgtgtatttt aatgttttaa caaatataaa tattttagat agataaatat    360

ttttgatagc gtgtgatatt gatgaactga ctagaaaata tttaattatt tttatgatctt   420

atttgagtta ttagacctta atttcgaaca cattttagga aaaaaaaaca tttataaaga    480

aaaaaaaaaa aggaaaagaa atgagtaaac tgaaaacagt ttaaagttta atttaacttt    540

atcatgtgtc aataatacca tgatatattg ttatattcat gatatattgt tatatcaaat    600

aaaaagttat atagacttat aaagcattat aatacatgta tgaaa                   645
```

```
<210> SEQ ID NO 140
<211> LENGTH: 23
<212> TYPE: DNA
<213> ORGANISM: Nezara viridula

<400> SEQUENCE: 140

aatcaaggtg tggactgaaa att                                            23
```

```
<210> SEQ ID NO 141
```

<211> LENGTH: 19
<212> TYPE: RNA
<213> ORGANISM: Nezara viridula

<400> SEQUENCE: 141
ucaaggugug gacugaaaa 19

<210> SEQ ID NO 142
<211> LENGTH: 19
<212> TYPE: RNA
<213> ORGANISM: Nezara viridula

<400> SEQUENCE: 142
uuuucagucc acaccuuga 19

<210> SEQ ID NO 143
<211> LENGTH: 23
<212> TYPE: DNA
<213> ORGANISM: Nezara viridula

<400> SEQUENCE: 143
aattggttgc tacatattct ctt 23

<210> SEQ ID NO 144
<211> LENGTH: 19
<212> TYPE: RNA
<213> ORGANISM: Nezara viridula

<400> SEQUENCE: 144
uugguugcua cauauucuc 19

<210> SEQ ID NO 145
<211> LENGTH: 19
<212> TYPE: RNA
<213> ORGANISM: Nezara viridula

<400> SEQUENCE: 145
gagaauaugu agcaaccaa 19

<210> SEQ ID NO 146
<211> LENGTH: 23
<212> TYPE: DNA
<213> ORGANISM: Nezara viridula

<400> SEQUENCE: 146
aagaacgtct taggatgcat att 23

<210> SEQ ID NO 147
<211> LENGTH: 19
<212> TYPE: RNA
<213> ORGANISM: Nezara viridula

<400> SEQUENCE: 147
gaacgucuua ggaugcaua 19

<210> SEQ ID NO 148
<211> LENGTH: 19
<212> TYPE: RNA
<213> ORGANISM: Nezara viridula

<400> SEQUENCE: 148
uaugcauccu aagacguuc 19

<210> SEQ ID NO 149
<211> LENGTH: 23
<212> TYPE: DNA
<213> ORGANISM: Nezara viridula

<400> SEQUENCE: 149
aagcaagcac ctaccttcac att 23

<210> SEQ ID NO 150
<211> LENGTH: 19
<212> TYPE: RNA
<213> ORGANISM: Nezara viridula

<400> SEQUENCE: 150
gcaagcaccu accuucaca 19

<210> SEQ ID NO 151
<211> LENGTH: 19
<212> TYPE: RNA
<213> ORGANISM: Nezara viridula

<400> SEQUENCE: 151
ugugaaggua ggugcuugc 19

<210> SEQ ID NO 152
<211> LENGTH: 23
<212> TYPE: DNA
<213> ORGANISM: Nezara viridula

<400> SEQUENCE: 152
aaaccaaggt agctgtggat ctt 23

<210> SEQ ID NO 153
<211> LENGTH: 19
<212> TYPE: RNA
<213> ORGANISM: Nezara viridula

<400> SEQUENCE: 153
accaagguag cuguggauc 19

<210> SEQ ID NO 154
<211> LENGTH: 19
<212> TYPE: RNA
<213> ORGANISM: Nezara viridula

<400> SEQUENCE: 154
gauccacagc uaccuuggu 19

<210> SEQ ID NO 155
<211> LENGTH: 23
<212> TYPE: DNA
<213> ORGANISM: Nezara viridula

<400> SEQUENCE: 155
aataatggat gtggtggcgg att 23

<210> SEQ ID NO 156
<211> LENGTH: 19
<212> TYPE: RNA
<213> ORGANISM: Nezara viridula

<400> SEQUENCE: 156
uaauggaugu gguggcgga 19

<210> SEQ ID NO 157
<211> LENGTH: 19
<212> TYPE: RNA
<213> ORGANISM: Nezara viridula

<400> SEQUENCE: 157
uccgccacca cauccauua 19

<210> SEQ ID NO 158
<211> LENGTH: 23
<212> TYPE: DNA
<213> ORGANISM: Nezara viridula

<400> SEQUENCE: 158
aaaaggatac cactttggac ttt 23

<210> SEQ ID NO 159
<211> LENGTH: 19
<212> TYPE: RNA
<213> ORGANISM: Nezara viridula

<400> SEQUENCE: 159
aaggauacca cuuuggacu 19

<210> SEQ ID NO 160
<211> LENGTH: 19
<212> TYPE: RNA
<213> ORGANISM: Nezara viridula

<400> SEQUENCE: 160
aguccaaagu gguauccuu 19

<210> SEQ ID NO 161
<211> LENGTH: 23
<212> TYPE: DNA
<213> ORGANISM: Nezara viridula

<400> SEQUENCE: 161
aaaggatacc actttggact ttt 23

<210> SEQ ID NO 162
<211> LENGTH: 19
<212> TYPE: RNA
<213> ORGANISM: Nezara viridula

<400> SEQUENCE: 162
aggauaccac uuuggacuu 19

<210> SEQ ID NO 163
<211> LENGTH: 19
<212> TYPE: RNA
<213> ORGANISM: Nezara viridula

<400> SEQUENCE: 163
aaguccaaag ugguauccu 19

<210> SEQ ID NO 164
<211> LENGTH: 23
<212> TYPE: DNA
<213> ORGANISM: Nezara viridula

<400> SEQUENCE: 164
aaaccaagac ccagactgga gtt 23

<210> SEQ ID NO 165
<211> LENGTH: 19
<212> TYPE: RNA
<213> ORGANISM: Nezara viridula

<400> SEQUENCE: 165
accaagaccc agacuggag 19

<210> SEQ ID NO 166
<211> LENGTH: 19
<212> TYPE: RNA
<213> ORGANISM: Nezara viridula

<400> SEQUENCE: 166
cuccagucug ggucuuggu 19

<210> SEQ ID NO 167
<211> LENGTH: 23
<212> TYPE: DNA
<213> ORGANISM: Nezara viridula

<400> SEQUENCE: 167
aagacccaga ctggagttga att 23

<210> SEQ ID NO 168
<211> LENGTH: 19
<212> TYPE: RNA
<213> ORGANISM: Nezara viridula

<400> SEQUENCE: 168
gacccagacu ggaguugaa 19

<210> SEQ ID NO 169
<211> LENGTH: 19
<212> TYPE: RNA
<213> ORGANISM: Nezara viridula

<400> SEQUENCE: 169
uucaacucca gucugggguc 19

<210> SEQ ID NO 170
<211> LENGTH: 23
<212> TYPE: DNA
<213> ORGANISM: Nezara viridula

<400> SEQUENCE: 170
aaccaagaaa ctgggaaagt gtt 23

<210> SEQ ID NO 171
<211> LENGTH: 19
<212> TYPE: RNA
<213> ORGANISM: Nezara viridula

<400> SEQUENCE: 171
ccaagaaacu gggaaagug 19

<210> SEQ ID NO 172
<211> LENGTH: 19
<212> TYPE: RNA
<213> ORGANISM: Nezara viridula

<400> SEQUENCE: 172
cacuuuccca guuucuugg 19

<210> SEQ ID NO 173
<211> LENGTH: 23
<212> TYPE: DNA
<213> ORGANISM: Nezara viridula

<400> SEQUENCE: 173
aactgggaaa gtgttcggaa att 23

<210> SEQ ID NO 174
<211> LENGTH: 19
<212> TYPE: RNA
<213> ORGANISM: Nezara viridula

<400> SEQUENCE: 174
cugggaaagu guucggaaa 19

<210> SEQ ID NO 175
<211> LENGTH: 19
<212> TYPE: RNA
<213> ORGANISM: Nezara viridula

<400> SEQUENCE: 175
uuuccgaaca cuuucccag 19

<210> SEQ ID NO 176
<211> LENGTH: 23
<212> TYPE: DNA
<213> ORGANISM: Nezara viridula

<400> SEQUENCE: 176
aactgaaatt gccctcactg att 23

<210> SEQ ID NO 177
<211> LENGTH: 19
<212> TYPE: RNA
<213> ORGANISM: Nezara viridula

<400> SEQUENCE: 177
cugaaauugc ccucacuga 19

<210> SEQ ID NO 178
<211> LENGTH: 19
<212> TYPE: RNA
<213> ORGANISM: Nezara viridula

<400> SEQUENCE: 178
ucagugaggg caauuucag 19

<210> SEQ ID NO 179
<211> LENGTH: 23
<212> TYPE: DNA
<213> ORGANISM: Nezara viridula

<400> SEQUENCE: 179
aagctttctt gtgatacctc att 23

<210> SEQ ID NO 180
<211> LENGTH: 19
<212> TYPE: RNA
<213> ORGANISM: Nezara viridula

<400> SEQUENCE: 180
gcuuucuugu gauaccuca 19

<210> SEQ ID NO 181
<211> LENGTH: 19
<212> TYPE: RNA
<213> ORGANISM: Nezara viridula

<400> SEQUENCE: 181
ugagguauca caagaaagc 19

<210> SEQ ID NO 182
<211> LENGTH: 23
<212> TYPE: DNA
<213> ORGANISM: Nezara viridula

<400> SEQUENCE: 182
aatgatacgt gtgctttgaa ctt 23

<210> SEQ ID NO 183
<211> LENGTH: 19
<212> TYPE: RNA
<213> ORGANISM: Nezara viridula

<400> SEQUENCE: 183
ugauacgugu gcuuugaac 19

<210> SEQ ID NO 184
<211> LENGTH: 19
<212> TYPE: RNA
<213> ORGANISM: Nezara viridula

<400> SEQUENCE: 184
guucaaagca cacguauca 19

<210> SEQ ID NO 185
<211> LENGTH: 23
<212> TYPE: DNA
<213> ORGANISM: Nezara viridula

<400> SEQUENCE: 185
aagcattaat gatggacgtg ttt 23

<210> SEQ ID NO 186
<211> LENGTH: 19
<212> TYPE: RNA
<213> ORGANISM: Nezara viridula

<400> SEQUENCE: 186
gcauuaauga uggacgugu 19

<210> SEQ ID NO 187
<211> LENGTH: 19
<212> TYPE: RNA
<213> ORGANISM: Nezara viridula

<400> SEQUENCE: 187
acacguccau cauuaaugc 19

<210> SEQ ID NO 188
<211> LENGTH: 23
<212> TYPE: DNA
<213> ORGANISM: Nezara viridula

<400> SEQUENCE: 188
aaaactttct caaagaacca gtt 23

<210> SEQ ID NO 189
<211> LENGTH: 19
<212> TYPE: RNA
<213> ORGANISM: Nezara viridula

<400> SEQUENCE: 189
aacuuucuca aagaaccag 19

<210> SEQ ID NO 190
<211> LENGTH: 19
<212> TYPE: RNA
<213> ORGANISM: Nezara viridula

<400> SEQUENCE: 190
cugguucuuu gagaaaguu 19

<210> SEQ ID NO 191
<211> LENGTH: 23
<212> TYPE: DNA
<213> ORGANISM: Nezara viridula

<400> SEQUENCE: 191
aaagaaccag ttccaaatgc att 23

<210> SEQ ID NO 192
<211> LENGTH: 19
<212> TYPE: RNA
<213> ORGANISM: Nezara viridula

<400> SEQUENCE: 192
agaaccaguu ccaaaugca 19

<210> SEQ ID NO 193
<211> LENGTH: 19
<212> TYPE: RNA
<213> ORGANISM: Nezara viridula

<400> SEQUENCE: 193
ugcauuugga acugguucu 19

<210> SEQ ID NO 194
<211> LENGTH: 23
<212> TYPE: DNA
<213> ORGANISM: Nezara viridula

<400> SEQUENCE: 194
aatgcattcc cttcaatctc att 23

<210> SEQ ID NO 195
<211> LENGTH: 19
<212> TYPE: RNA
<213> ORGANISM: Nezara viridula

<400> SEQUENCE: 195
ugcauucccu ucaaucuca 19

<210> SEQ ID NO 196
<211> LENGTH: 19
<212> TYPE: RNA
<213> ORGANISM: Nezara viridula

<400> SEQUENCE: 196
ugagauugaa gggaaugca 19

<210> SEQ ID NO 197
<211> LENGTH: 23
<212> TYPE: DNA
<213> ORGANISM: Nezara viridula

<400> SEQUENCE: 197
aacctctcct cgtctggagt ctt 23

<210> SEQ ID NO 198
<211> LENGTH: 19
<212> TYPE: RNA
<213> ORGANISM: Nezara viridula

<400> SEQUENCE: 198
ccucuccucg ucuggaguc 19

<210> SEQ ID NO 199
<211> LENGTH: 19
<212> TYPE: RNA
<213> ORGANISM: Nezara viridula

<400> SEQUENCE: 199
gacuccagac gaggagagg 19

<210> SEQ ID NO 200
<211> LENGTH: 23
<212> TYPE: DNA
<213> ORGANISM: Nezara viridula

<400> SEQUENCE: 200
aaagaattca cctggtccta ctt 23

<210> SEQ ID NO 201
<211> LENGTH: 19
<212> TYPE: RNA
<213> ORGANISM: Nezara viridula

<400> SEQUENCE: 201
agaauucacc ugguccuac 19

<210> SEQ ID NO 202
<211> LENGTH: 19
<212> TYPE: RNA
<213> ORGANISM: Nezara viridula

<400> SEQUENCE: 202
guaggaccag gugaauucu 19

<210> SEQ ID NO 203
<211> LENGTH: 23
<212> TYPE: DNA
<213> ORGANISM: Nezara viridula

<400> SEQUENCE: 203
aattctggaa gaaatggacc att 23

<210> SEQ ID NO 204
<211> LENGTH: 19
<212> TYPE: RNA

<213> ORGANISM: Nezara viridula

<400> SEQUENCE: 204
uucuggaaga aauggacca 19

<210> SEQ ID NO 205
<211> LENGTH: 19
<212> TYPE: RNA
<213> ORGANISM: Nezara viridula

<400> SEQUENCE: 205
ugguccauuu cuuccagaa 19

<210> SEQ ID NO 206
<211> LENGTH: 23
<212> TYPE: DNA
<213> ORGANISM: Nezara viridula

<400> SEQUENCE: 206
aacgtctaga aatggtgaga gtt 23

<210> SEQ ID NO 207
<211> LENGTH: 19
<212> TYPE: RNA
<213> ORGANISM: Nezara viridula

<400> SEQUENCE: 207
cgucuagaaa uggugagag 19

<210> SEQ ID NO 208
<211> LENGTH: 19
<212> TYPE: RNA
<213> ORGANISM: Nezara viridula

<400> SEQUENCE: 208
cucucaccau uucuagacg 19

<210> SEQ ID NO 209
<211> LENGTH: 23
<212> TYPE: DNA
<213> ORGANISM: Nezara viridula

<400> SEQUENCE: 209
aataagaaac acgaagcagg ctt 23

<210> SEQ ID NO 210
<211> LENGTH: 19
<212> TYPE: RNA
<213> ORGANISM: Nezara viridula

<400> SEQUENCE: 210
uaagaaacac gaagcaggc 19

<210> SEQ ID NO 211
<211> LENGTH: 19
<212> TYPE: RNA
<213> ORGANISM: Nezara viridula

<400> SEQUENCE: 211
gccugcuucg uguuucuua 19

<210> SEQ ID NO 212
<211> LENGTH: 23

<212> TYPE: DNA
<213> ORGANISM: Nezara viridula

<400> SEQUENCE: 212
aaatgaagag ccatttaggc ttt 23

<210> SEQ ID NO 213
<211> LENGTH: 19
<212> TYPE: RNA
<213> ORGANISM: Nezara viridula

<400> SEQUENCE: 213
augaagagcc auuuaggcu 19

<210> SEQ ID NO 214
<211> LENGTH: 19
<212> TYPE: RNA
<213> ORGANISM: Nezara viridula

<400> SEQUENCE: 214
agccuaaaug gcucuucau 19

<210> SEQ ID NO 215
<211> LENGTH: 23
<212> TYPE: DNA
<213> ORGANISM: Nezara viridula

<400> SEQUENCE: 215
aacttcgaac catctccccg gtt 23

<210> SEQ ID NO 216
<211> LENGTH: 19
<212> TYPE: RNA
<213> ORGANISM: Nezara viridula

<400> SEQUENCE: 216
cuucgaacca ucuccccgg 19

<210> SEQ ID NO 217
<211> LENGTH: 19
<212> TYPE: RNA
<213> ORGANISM: Nezara viridula

<400> SEQUENCE: 217
ccggggagau gguucgaag 19

<210> SEQ ID NO 218
<211> LENGTH: 23
<212> TYPE: DNA
<213> ORGANISM: Nezara viridula

<400> SEQUENCE: 218
aagcttcctt cactacaaat gtt 23

<210> SEQ ID NO 219
<211> LENGTH: 19
<212> TYPE: RNA
<213> ORGANISM: Nezara viridula

<400> SEQUENCE: 219
gcuuccuuca cuacaaaug 19

<210> SEQ ID NO 220

<211> LENGTH: 19
<212> TYPE: RNA
<213> ORGANISM: Nezara viridula

<400> SEQUENCE: 220
cauuuguagu gaaggaagc 19

<210> SEQ ID NO 221
<211> LENGTH: 23
<212> TYPE: DNA
<213> ORGANISM: Nezara viridula

<400> SEQUENCE: 221
aaggttcagc tccggggatc ttt 23

<210> SEQ ID NO 222
<211> LENGTH: 19
<212> TYPE: RNA
<213> ORGANISM: Nezara viridula

<400> SEQUENCE: 222
gguucagcuc cggggaucu 19

<210> SEQ ID NO 223
<211> LENGTH: 19
<212> TYPE: RNA
<213> ORGANISM: Nezara viridula

<400> SEQUENCE: 223
agauccccgg agcugaacc 19

<210> SEQ ID NO 224
<211> LENGTH: 23
<212> TYPE: DNA
<213> ORGANISM: Nezara viridula

<400> SEQUENCE: 224
aatcgacgac caaaatactg att 23

<210> SEQ ID NO 225
<211> LENGTH: 19
<212> TYPE: RNA
<213> ORGANISM: Nezara viridula

<400> SEQUENCE: 225
ucgacgacca aaauacuga 19

<210> SEQ ID NO 226
<211> LENGTH: 19
<212> TYPE: RNA
<213> ORGANISM: Nezara viridula

<400> SEQUENCE: 226
ucaguauuuu ggucgucga 19

<210> SEQ ID NO 227
<211> LENGTH: 23
<212> TYPE: DNA
<213> ORGANISM: Nezara viridula

<400> SEQUENCE: 227
aatacttcag agtacggcgt att 23

<210> SEQ ID NO 228
<211> LENGTH: 19
<212> TYPE: RNA
<213> ORGANISM: Nezara viridula

<400> SEQUENCE: 228
uacuucagag uacggcgua 19

<210> SEQ ID NO 229
<211> LENGTH: 19
<212> TYPE: RNA
<213> ORGANISM: Nezara viridula

<400> SEQUENCE: 229
uacgccguac ucugaagua 19

<210> SEQ ID NO 230
<211> LENGTH: 23
<212> TYPE: DNA
<213> ORGANISM: Nezara viridula

<400> SEQUENCE: 230
aaaatgagag ctacgtactg ctt 23

<210> SEQ ID NO 231
<211> LENGTH: 19
<212> TYPE: RNA
<213> ORGANISM: Nezara viridula

<400> SEQUENCE: 231
aaugagagcu acguacugc 19

<210> SEQ ID NO 232
<211> LENGTH: 19
<212> TYPE: RNA
<213> ORGANISM: Nezara viridula

<400> SEQUENCE: 232
gcaguacgua gcucucauu 19

<210> SEQ ID NO 233
<211> LENGTH: 23
<212> TYPE: DNA
<213> ORGANISM: Nezara viridula

<400> SEQUENCE: 233
aaataccatt acacaggaca ttt 23

<210> SEQ ID NO 234
<211> LENGTH: 19
<212> TYPE: RNA
<213> ORGANISM: Nezara viridula

<400> SEQUENCE: 234
auaccauuac acaggacau 19

<210> SEQ ID NO 235
<211> LENGTH: 19
<212> TYPE: RNA
<213> ORGANISM: Nezara viridula

<400> SEQUENCE: 235
auguccugug uaaugguau 19

<210> SEQ ID NO 236
<211> LENGTH: 23
<212> TYPE: DNA
<213> ORGANISM: Nezara viridula

<400> SEQUENCE: 236
aagtgttgct ggaacatcaa gtt 23

<210> SEQ ID NO 237
<211> LENGTH: 19
<212> TYPE: RNA
<213> ORGANISM: Nezara viridula

<400> SEQUENCE: 237
guguugcugg aacaucaag 19

<210> SEQ ID NO 238
<211> LENGTH: 19
<212> TYPE: RNA
<213> ORGANISM: Nezara viridula

<400> SEQUENCE: 238
cuugauguuc cagcaacac 19

<210> SEQ ID NO 239
<211> LENGTH: 23
<212> TYPE: DNA
<213> ORGANISM: Nezara viridula

<400> SEQUENCE: 239
aatgcccagc agaaaccaac ctt 23

<210> SEQ ID NO 240
<211> LENGTH: 19
<212> TYPE: RNA
<213> ORGANISM: Nezara viridula

<400> SEQUENCE: 240
ugcccagcag aaaccaacc 19

<210> SEQ ID NO 241
<211> LENGTH: 19
<212> TYPE: RNA
<213> ORGANISM: Nezara viridula

<400> SEQUENCE: 241
gguugguuuc ugcugggca 19

<210> SEQ ID NO 242
<211> LENGTH: 23
<212> TYPE: DNA
<213> ORGANISM: Nezara viridula

<400> SEQUENCE: 242
aaataccaca gccagcaata att 23

<210> SEQ ID NO 243
<211> LENGTH: 19
<212> TYPE: RNA
<213> ORGANISM: Nezara viridula

<400> SEQUENCE: 243
auaccacagc cagcaauaa 19

<210> SEQ ID NO 244
<211> LENGTH: 19
<212> TYPE: RNA
<213> ORGANISM: Nezara viridula

<400> SEQUENCE: 244
uuauugcugg cugugguau 19

<210> SEQ ID NO 245
<211> LENGTH: 23
<212> TYPE: DNA
<213> ORGANISM: Nezara viridula

<400> SEQUENCE: 245
aataccacag ccagcaataa ttt 23

<210> SEQ ID NO 246
<211> LENGTH: 19
<212> TYPE: RNA
<213> ORGANISM: Nezara viridula

<400> SEQUENCE: 246
uaccacagcc agcaauaau 19

<210> SEQ ID NO 247
<211> LENGTH: 19
<212> TYPE: RNA
<213> ORGANISM: Nezara viridula

<400> SEQUENCE: 247
auuauugcug gcugguggua 19

<210> SEQ ID NO 248
<211> LENGTH: 23
<212> TYPE: DNA
<213> ORGANISM: Nezara viridula

<400> SEQUENCE: 248
aagcctccgg tacctcaagg ttt 23

<210> SEQ ID NO 249
<211> LENGTH: 19
<212> TYPE: RNA
<213> ORGANISM: Nezara viridula

<400> SEQUENCE: 249
gccuccggua ccucaaggu 19

<210> SEQ ID NO 250
<211> LENGTH: 19
<212> TYPE: RNA
<213> ORGANISM: Nezara viridula

<400> SEQUENCE: 250
accuugaggu accggaggc 19

<210> SEQ ID NO 251
<211> LENGTH: 23
<212> TYPE: DNA
<213> ORGANISM: Nezara viridula

<400> SEQUENCE: 251
aatcttatcg gacaaaccag ttt 23

<210> SEQ ID NO 252
<211> LENGTH: 19
<212> TYPE: RNA
<213> ORGANISM: Nezara viridula

<400> SEQUENCE: 252
ucuuaucgga caaaccagu 19

<210> SEQ ID NO 253
<211> LENGTH: 19
<212> TYPE: RNA
<213> ORGANISM: Nezara viridula

<400> SEQUENCE: 253
acugguuugu ccgauaaga 19

<210> SEQ ID NO 254
<211> LENGTH: 23
<212> TYPE: DNA
<213> ORGANISM: Nezara viridula

<400> SEQUENCE: 254
aaaaatatcc attgccactg ttt 23

<210> SEQ ID NO 255
<211> LENGTH: 19
<212> TYPE: RNA
<213> ORGANISM: Nezara viridula

<400> SEQUENCE: 255
aaauauccau ugccacugu 19

<210> SEQ ID NO 256
<211> LENGTH: 19
<212> TYPE: RNA
<213> ORGANISM: Nezara viridula

<400> SEQUENCE: 256
acaguggcaa uggauauuu 19

<210> SEQ ID NO 257
<211> LENGTH: 23
<212> TYPE: DNA
<213> ORGANISM: Nezara viridula

<400> SEQUENCE: 257
aaaatatcca ttgccactgt ttt 23

<210> SEQ ID NO 258
<211> LENGTH: 19
<212> TYPE: RNA
<213> ORGANISM: Nezara viridula

<400> SEQUENCE: 258
aauauccauu gccacuguu 19

<210> SEQ ID NO 259
<211> LENGTH: 19
<212> TYPE: RNA
<213> ORGANISM: Nezara viridula

<400> SEQUENCE: 259
aacaguggca auggauauu 19

<210> SEQ ID NO 260
<211> LENGTH: 23
<212> TYPE: DNA
<213> ORGANISM: Nezara viridula

<400> SEQUENCE: 260
aaatatccat tgccactgtt ttt 23

<210> SEQ ID NO 261
<211> LENGTH: 19
<212> TYPE: RNA
<213> ORGANISM: Nezara viridula

<400> SEQUENCE: 261
auauccauug ccacuguuu 19

<210> SEQ ID NO 262
<211> LENGTH: 19
<212> TYPE: RNA
<213> ORGANISM: Nezara viridula

<400> SEQUENCE: 262
aaacaguggc aauggauau 19

<210> SEQ ID NO 263
<211> LENGTH: 23
<212> TYPE: DNA
<213> ORGANISM: Nezara viridula

<400> SEQUENCE: 263
aaggatggga tgtgttccga gtt 23

<210> SEQ ID NO 264
<211> LENGTH: 19
<212> TYPE: RNA
<213> ORGANISM: Nezara viridula

<400> SEQUENCE: 264
ggaugggaug uguuccgag 19

<210> SEQ ID NO 265
<211> LENGTH: 19
<212> TYPE: RNA
<213> ORGANISM: Nezara viridula

<400> SEQUENCE: 265
cucggaacac aucccaucc 19

<210> SEQ ID NO 266
<211> LENGTH: 23
<212> TYPE: DNA
<213> ORGANISM: Nezara viridula

<400> SEQUENCE: 266
aagatggggg gatgatgtac gtt 23

<210> SEQ ID NO 267
<211> LENGTH: 19
<212> TYPE: RNA
<213> ORGANISM: Nezara viridula

<400> SEQUENCE: 267 gauggggga ugauguacg 19

<210> SEQ ID NO 268
<211> LENGTH: 19
<212> TYPE: RNA
<213> ORGANISM: Nezara viridula

<400> SEQUENCE: 268
cguacaucau ccccccauc 19

<210> SEQ ID NO 269
<211> LENGTH: 23
<212> TYPE: DNA
<213> ORGANISM: Nezara viridula

<400> SEQUENCE: 269
aagaacatcc acaggagaac ctt 23

<210> SEQ ID NO 270
<211> LENGTH: 19
<212> TYPE: RNA
<213> ORGANISM: Nezara viridula

<400> SEQUENCE: 270
gaacauccac aggagaacc 19

<210> SEQ ID NO 271
<211> LENGTH: 19
<212> TYPE: RNA
<213> ORGANISM: Nezara viridula

<400> SEQUENCE: 271
gguucuccug uggauguuc 19

<210> SEQ ID NO 272
<211> LENGTH: 23
<212> TYPE: DNA
<213> ORGANISM: Nezara viridula

<400> SEQUENCE: 272
aagactctat taatatccag ctt 23

<210> SEQ ID NO 273
<211> LENGTH: 19
<212> TYPE: RNA
<213> ORGANISM: Nezara viridula

<400> SEQUENCE: 273
gacucuauua auauccagc 19

<210> SEQ ID NO 274
<211> LENGTH: 19
<212> TYPE: RNA
<213> ORGANISM: Nezara viridula

<400> SEQUENCE: 274
gcuggauauu aauagaguc 19

<210> SEQ ID NO 275
<211> LENGTH: 23
<212> TYPE: DNA
<213> ORGANISM: Nezara viridula

<400> SEQUENCE: 275
aaatggaaag ctgggcagaa ctt 23

<210> SEQ ID NO 276
<211> LENGTH: 19
<212> TYPE: RNA
<213> ORGANISM: Nezara viridula

<400> SEQUENCE: 276
auggaaagcu gggcagaac 19

<210> SEQ ID NO 277
<211> LENGTH: 19
<212> TYPE: RNA
<213> ORGANISM: Nezara viridula

<400> SEQUENCE: 277
guucugccca gcuuuccau 19

<210> SEQ ID NO 278
<211> LENGTH: 1053
<212> TYPE: DNA
<213> ORGANISM: Nezara viridula

<400> SEQUENCE: 278
ggaaatatgt agtaggaaca aaagtcagtt aagtagtatg ctctctgcaa tcttggacta 60
taccagcaat aaaaacttta tcattagaga taaaaaagat atatcatttt tttctaaagc 120
tatggaagtt tgtagtaaac tcaaagataa ggatcttctc tacaggcttc atgaattatt 180
gttgaccgga aacaattata atttgatcgg agattcattt agtgaatcgg tgtattaccg 240
ttattttttt ttatttgctt actgatactg aagaacttag taaagtaatg gaattctatg 300
atgaccttgt accaaacgtt tatgttccag agccatcagt gaccaatgct atattgaaag 360
ctgtttgtaa caacatggca tgggaccttc ttcccaagct ttggccagac atactattgt 420
ttgagcagta tgaagtttcc ggtgtcctgg aaaatatttt agatattgca tctcaaaatg 480
aaggcaagaa tttgatggaa gggatgtcta aaattgcatg gtctgcatgg gagaagatag 540
aaggaataaa gagggagcga tccaactttc aatggtctgc gagtgcattg ggaaacatta 600
ttctcatttt gttgaaatct ggtgaaaaag ctaaggcgaa tttggttatg aataaattaa 660
ttcaactagg aagttctgcc atgaatgaac caaaaataga ggctttgagt ctctacgtgg 720
acagttgcat agaaagttca tcaccagatg tagcaattaa atgcattcaa tattgcaacg 780
atattggatt tacggaaacc acagagtttg ctaggcgaat caattcttct atcgagctca 840
acccaaggca atatgaaaaa ttaacatcta ttgtaggcga agattgtctg aaagttgaaa 900
agaaaaaaga tcaaagtagt tgaaattgtt tttagacttt taataaatgt ataattttac 960
attgttagtt aatatttgca tagttttctt gtaatataat cactagttca actgttttat 1020
tctaatttaa gagaataaaa gttttacatt tcc 1053

<210> SEQ ID NO 279
<211> LENGTH: 861
<212> TYPE: DNA
<213> ORGANISM: Nezara viridula

<400> SEQUENCE: 279
agtttgaata atttcaatct catctaaagg attatttaat gtgaatgatt tgtgtcagtt 60

```
tttactttta actgcggcat atagcctgct gcagttaatg cgggaaggtt taccttatta    120

tgtctgactg ggaacaaaga ttgctcagcc tggaaaaact ggacaggtca tcgccagagc    180

tctggccaga gccgatacct ggggtgacag aatatgctgc tcgcaatgct ctttctagtt    240

cctctgttcc aaagaacatt gaatcactcc agagtcagtt tactgaggat gactataagc    300

tgctaaatta ttacagtact ctttctaaag aatctctgat tcaagaatta aagaagcttc    360

atgaccaggc ctataaatta ggtcttgaag aagccaagga aatgactaga ggaagatttt    420

tgaacatact gtctaccaga aaaaagtaat ggtttgtaaa tgctgccatg cttctgaatg    480

gttccatcat attctgatcc agaagaagga agttgtagcg aatggagtag gtataaaagt    540

gagtcaataa ggacaagaag ggctaattta atgtattttt ccaaatattt ttgtaattgc    600

agaatagaag atttatgtga agaaatgaat ttaagttttt gttgttgtaa ctgtctgtta    660

tagttccttc agtcccaaat attttgttgg cttctaatca agctcttgta tttattaatt    720

ttctttttca attcaattaa ttaaagtgtt gctaaaaagt tgataatatt aaagtaaatt    780

tagtttattt ttatttccca gaattaatta tttattattg ttatctgtac taagaataaa    840

aaatatgtta attgttctcc g                                              861
```

<210> SEQ ID NO 280
<211> LENGTH: 992
<212> TYPE: DNA
<213> ORGANISM: Nezara viridula

<400> SEQUENCE: 280

```
gaagaaattg agagaatggt taatgatgcc gagaaataca aggctgaaga tgataagcag     60

aaagctgtca ttcaagctaa gaacactctg gagtcctatt gtttcaatat gaaatctact    120

gtagaggatg aaaaactgaa agacaaaatt tccgattctg ataaaactac aattttggag    180

aaatgtaatg aagttattcg ctggctcgat gctaatcagt tagctgaaaa agaagaattc    240

gaacataagc aaaaggaatt ggaagccata tgcaatccta ttattactaa attgtaccaa    300

agtggtggta tgcccggagg aatgccaggt ggtatgcctg gtggtttccc aggcggtgcc    360

cctcctaatg ctggtggtgc tgctggacct accattgaag aagttgatta aacattccat    420

gcgaataaac acacaaataa tacattgtat aattaatgct agttgaattg caattttttt    480

ttcctttcta gtcaagagac cttcaaatgg ccttgtattt ttgtttaaaa atttaatgtt    540

aataatgtaa cttttacaag tattttgttt atttataatt tttttatatg ttctgtcatt    600

ggtatcaatg aattatatta gagttactat taactaatgt ttttaaataa aaatatagcc    660

tgtagaggaa tacttgatgt aaatgtatac agtattaaat gagccatata atttttattt    720

aaattccatt tttttaattt atatattgat aaattgcatt ttgtgtgtta tacttgcctc    780

attgaattta tgttaatgaa tattttttat agttaaaaaa aaaggctgat tccaatttaa    840

gttttatttt gaagaagaat tttgtaccct tgtttgataa atcttgtgaa tcttgttatg    900

gttaaacatc ttttggtaac cacccttttgg ttgtattcaa aattgtgaat gaaacatttt    960

cggcacaaaa ttaataaaat taattattcc ac                                  992
```

<210> SEQ ID NO 281
<211> LENGTH: 858
<212> TYPE: DNA
<213> ORGANISM: Nezara viridula

<400> SEQUENCE: 281

```
agtgtccgcc ctcttcatct cctgtcttgt atcatcacat catccttccc cttctctcgc     60
```

```
tgagtcaact tacgccaaac cgtcatccag cggtaggaag cgagaggctg ccctagattg    120

tatgctaggc tctctcaccg agaacatgtc caggcaagga gtcacaacga cacagaaagg    180

ctgctgttca gcttgcgaca aacccattgt cggccaggta atcacagcac taggcaagac    240

atggcatcca gaacactttg tctgcacaca ctgcaaccag gagcttggaa caagaaactt    300

ctttgagagg gatggtcacc cctactgtga gccagattac cacaacctct tcagtcctcg    360

atgtgcctac tgcaacggcc ctatcttaga taaatgtgtc acagccttgg aaaaaacatg    420

gcatacggaa catttctttt gtgctcagtg tggtaaacag tttggggaag aggggttcca    480

tgagaaagat ggtcgaccct attgtcggga cgattacttt gaaatgtttg ctccaaaatg    540

tggcggctgt tcccgcccaa taatggagaa ctatatttca gccctctcaa tgcagtggca    600

tcaagactgt tttgtctgca gggattgccg gaagcccgtc acagggaaga ccttttatgc    660

catggaagga aagcctgtct gtccgaaatg tgtcggagtg gacgaggaag aagaagactg    720

aagattcggc aaaaactaat acctctatat taaatgcttt tttatagaac cacgcgaatc    780

ataaccacca tcctaccaac tctgtattta tatttgtata gaaaataaaa gttttttttt    840

ttttttttta ttaattag                                                  858
```

<210> SEQ ID NO 282
<211> LENGTH: 643
<212> TYPE: DNA
<213> ORGANISM: Nezara viridula

<400> SEQUENCE: 282

```
gggtgcctag ggtgcccctt cctggagcag gtggtggaat tggttcagca agacctgcgg     60

gacgtggagt tccagctcct ggtacaccag ctgcacctgg tctccaaggt ccagttcgtg    120

gtgtaggtgg cccatctgca caagttatga ctccagcggg gcgtggagga caagtttctg    180

ctcctcctca gatgcgtgct ccacccccag gaatgccccc aatgatggga gctccaccaa    240

tgatgaacat ggcaccagga atggcgatgg gaagaggtgg accacctcct caaatgggtg    300

ctcctccagc tccaccaatg cgaggtcccc caccaggaat gatgagaggt ccccctcctt    360

tttaagaaga aagaaaattt tgttaccttc cttctgtaat tttttttaa gtttgaaatt    420

tacaaagcca atggatggct aagattaatt tctgactttt ttttggatac ataccattta    480

tttatgtaaa tgtgctcatg tatgtatata tttatctatg cattttggaa aaagaatatt    540

tgtactaaat tatttgataa ataattgtag taattatact taaacactct ggtctttatt    600

taataaacca ttgttttttt attaattgta ataaatttgt ttt                      643
```

<210> SEQ ID NO 283
<211> LENGTH: 792
<212> TYPE: DNA
<213> ORGANISM: Nezara viridula

<400> SEQUENCE: 283

```
attgaggttt cagtttctgc acagtccagt gactttggtt tcgatcggga tttatatctc     60

tattatggac aatttgggtc aacaaacacc tcatcaaaat aatcattcaa atgatacaga    120

aatgaacaat tttatggacg tatccagaat gagtaccatg tggccttatc cacatcctga    180

caggttttca caatacaggg atttctttca tgaacctcag caaggagtag tttctgggaa    240

tgaaacaaca aataatgtta gccaagtatt aacaaacaat tccacacagc aacattcttt    300

agtgaatact atgcctgtta tgggaacttt acaaacagta ttaactcaag gtttgccaaa    360
```

```
ccaaaatgct aatgctaatg ttgttaattt aaatcatact ccacagaatt tacccagtac    420

tattcagact tccataaata gccttccaaa tgccaccaac tctaccagtc aaggacaaga    480

gcaatctacc cagatattaa caagaatgag gttgcaagat ttggtgagag aagtagatcc    540

taatgaacaa ttagacgaag atgttgaaga tgtattatta caaatggcag atgattttgt    600

tgactcagca attacagctg gttgtcttct tgccaagcac agaaaatcaa ctactgtaga    660

agttaaggat cttcagctac atttagaaag aaattggaat atgtggatac ctggttttgg    720

aacagatgaa ttgcgacctt acaaacgtgc atctgttaca gaagctcata aacaaagact    780

tacgcttatc ac                                                         792
```

```
<210> SEQ ID NO 284
<211> LENGTH: 536
<212> TYPE: DNA
<213> ORGANISM: Nezara viridula

<400> SEQUENCE: 284

gaaatatgta gtaggaacaa aagtcagtta agtagtatgc tctctgcaat cttggactat     60

accagcaata aaaactttat cattagagat aaaaaagata tatcattttt ttctaaagct    120

atggaagttt gtagtaaact caaagataag gatcttctct acaggcttca tgaattattg    180

ttgaccggaa acaattataa tttgatcgga gattcattta gtgaatcggt gtattaccgt    240

tatttttttt tatttgctta ctgatactga agaacttagt aaagtaatgg aattctatga    300

tgaccttgta ccaaacgttt atgttccaga gccatcagtg accaatgcta tattgaaagc    360

tgtttgtaac aacatggcat gggaccttct tcccaagctt tggccagaca tactattgtt    420

tgagcagtat gaagtttccg gtgtcctgga aaatatttta gatattgcat ctcaaaatga    480

aggcaagaat ttgatggaag ggatgtctaa aattgcatgg tctgcatggg agaaga         536
```

```
<210> SEQ ID NO 285
<211> LENGTH: 605
<212> TYPE: DNA
<213> ORGANISM: Nezara viridula

<400> SEQUENCE: 285

tgcggcatat agcctgctgc agttaatgcg ggaaggttta ccttattatg tctgactggg     60

aacaaagatt gctcagcctg gaaaaactgg acaggtcatc gccagagctc tggccagagc    120

cgatacctgg ggtgacagaa tatgctgctc gcaatgctct ttctagttcc tctgttccaa    180

agaacattga atcactccag agtcagttta ctgaggatga ctataagctg ctaaattatt    240

acagtactct ttctaaagaa tctctgattc aagaattaaa gaagcttcat gaccaggcct    300

ataaattagg tcttgaagaa gccaaggaaa tgactagagg aagattttttg aacatactgt   360

ctaccagaaa aaagtaatgg tttgtaaatg ctgccatgct tctgaatggt tccatcatat    420

tctgatccag aagaaggaag ttgtagcgaa tggagtaggt ataaaagtga gtcaataagg    480

acaagaaggg ctaatttaat gtatttttcc aaatattttt gtaattgcag aatagaagat    540

ttatgtgaag aaatgaattt aagtttttgt tgttgtaact gtctgttata gttccttcag    600

tccca                                                                605
```

```
<210> SEQ ID NO 286
<211> LENGTH: 762
<212> TYPE: DNA
<213> ORGANISM: Nezara viridula

<400> SEQUENCE: 286
```

```
tgcggcatat agcctgctgc agttaatgcg ggaaggttta ccttattatg tctgactggg     60
aacaaagatt gctcagcctg gaaaaactgg acaggtcatc gccagagctc tggccagagc    120
cgatacctgg ggtgacagaa tatgctgctc gcaatgctct ttctagttcc tctgttccaa    180
agaacattga atcactccag agtcagttta ctgaggatga ctataagctg ctaaattatt    240
acagtactct ttctaaagaa tctctgattc aagaattaaa gaagcttcat gaccaggcct    300
ataaattagg tcttgaagaa gccaaggaaa tgactagagg aagatttttg aacatactgt    360
ctaccagaaa aaagtaatgg tttgtaaatg ctgccatgct tctgaatggt tccatcatat    420
tctgatccag aagaaggaag ttgtagcgaa tggagtaggt ataaaagtga gtcaataagg    480
acaagaaggg ctaatttaat gtatttttcc aaatattttt gtaattgcag aatagaagat    540
ttatgtgaag aaatgaattt aagtttttgt tgttgtaact gtctgttata gttccttcag    600
tcccaaatat tttgttggct tctaatcaag ctcttgtatt tattaatttt ctttttcaat    660
tcaattaatt aaagtgttgc taaaaagttg ataatattaa agtaaattta gtttattttt    720
atttcccaga attaattatt tattattgtt atctgtacta ag                       762
```

<210> SEQ ID NO 287
<211> LENGTH: 367
<212> TYPE: DNA
<213> ORGANISM: Nezara viridula

<400> SEQUENCE: 287

```
tgcggcatat agcctgctgc agttaatgcg ggaaggttta ccttattatg tctgactggg     60
aacaaagatt gctcagcctg gaaaaactgg acaggtcatc gccagagctc tggccagagc    120
cgatacctgg ggtgacagaa tatgctgctc gcaatgctct ttctagttcc tctgttccaa    180
agaacattga atcactccag agtcagttta ctgaggatga ctataagctg ctaaattatt    240
acagtactct ttctaaagaa tctctgattc aagaattaaa gaagcttcat gaccaggcct    300
ataaattagg tcttgaagaa gccaaggaaa tgactagagg aagatttttg aacatactgt    360
ctaccag                                                              367
```

<210> SEQ ID NO 288
<211> LENGTH: 485
<212> TYPE: DNA
<213> ORGANISM: Nezara viridula

<400> SEQUENCE: 288

```
tgccgagaaa tacaaggctg aagatgataa gcagaaagct gtcattcaag ctaagaacac     60
tctggagtcc tattgtttca atatgaaatc tactgtagag gatgaaaaac tgaaagacaa    120
aatttccgat tctgataaaa ctacaatttt ggagaaatgt aatgaagtta ttcgctggct    180
cgatgctaat cagttagctg aaaaagaaga attcgaacat aagcaaaagg aattggaagc    240
catatgcaat cctattatta ctaaattgta ccaaagtggt ggtatgcccg gaggaatgcc    300
aggtggtatg cctggtggtt tcccaggcgg tgcccctcct aatgctggtg gtgctgctgg    360
acctaccatt gaagaagttg attaaacatt ccatgcgaat aaacacacaa ataatacatt    420
gtataattaa tgctagttga attgcaattt ttttttcctt tctagtcaag agaccttcaa    480
atggc                                                                485
```

<210> SEQ ID NO 289
<211> LENGTH: 451
<212> TYPE: DNA

<213> ORGANISM: Nezara viridula

<400> SEQUENCE: 289
ctagtcaaga gaccttcaaa tggccttgta tttttgttta aaaatttaat gttaataatg 60
taacttttac aagtattttg tttatttata attttttttat atgttctgtc attggtatca 120
atgaattata ttagagttac tattaactaa tgtttttaaa taaaaatata gcctgtagag 180
gaatacttga tgtaaatgta tacagtatta aatgagccat ataattttta tttaaattcc 240 attttttaa tttatatatt gataaattgc attttgtgtg ttatacttgc ctcattgaat 300
ttatgttaat gaatattttt tatagttaaa aaaaaaggct gattccaatt taagttttat 360
tttgaagaag aattttgtac ccttgtttga taaatcttgt gaatcttgtt atggttaaac 420
atcttttggt aaccaccctt tggttgtatt c 451

<210> SEQ ID NO 290
<211> LENGTH: 799
<212> TYPE: DNA
<213> ORGANISM: Nezara viridula

<400> SEQUENCE: 290
gtgtccgccc tcttcatctc ctgtcttgta tcatcacatc atccttcccc ttctctcgct 60
gagtcaactt acgccaaacc gtcatccagc ggtaggaagc gagaggctgc cctagattgt 120
atgctaggct ctctcaccga gaacatgtcc aggcaaggag tcacaacgac acagaaaggc 180
tgctgttcag cttgcgacaa acccattgtc ggccaggtaa tcacagcact aggcaagaca 240
tggcatccag aacactttgt ctgcacacac tgcaaccagg agcttggaac aagaaacttc 300
tttgagaggg atggtcaccc ctactgtgag ccagattacc acaacctctt cagtcctcga 360
tgtgcctact gcaacggccc tatcttagat aaatgtgtca cagccttgga aaaaacatgg 420
catacggaac atttcttttg tgctcagtgt ggtaaacagt ttggggaaga ggggttccat 480
gagaaagatg gtcgacccta ttgtcgggac gattactttg aaatgtttgc tccaaaatgt 540
ggcggctgtt cccgcccaat aatggagaac tatatttcag ccctctcaat gcagtggcat 600
caagactgtt ttgtctgcag ggattgccgg aagcccgtca cagggaagac cttttatgcc 660
atggaaggaa agcctgtctg tccgaaatgt gtcggagtgg acgaggaaga agaagactga 720
agattcggca aaaactaata cctctatatt aaatgctttt ttatagaacc acgcgaatca 780
taaccaccat cctaccaac 799

<210> SEQ ID NO 291
<211> LENGTH: 576
<212> TYPE: DNA
<213> ORGANISM: Nezara viridula

<400> SEQUENCE: 291
ttcctggagc aggtggtgga attggttcag caagacctgc gggacgtgga gttccagctc 60
ctggtacacc agctgcacct ggtctccaag gtccagttcg tggtgtaggt ggcccatctg 120
cacaagttat gactccagcg gggcgtggag gacaagtttc tgctcctcct cagatgcgtg 180
ctccaccccc aggaatgccc ccaatgatgg gagctccacc aatgatgaac atggcaccag 240
gaatggcgat gggaagaggt ggaccacctc ctcaaatggg tgctcctcca gctccaccaa 300
tgcgaggtcc cccaccagga atgatgagag gtccccctcc tttttaagaa gaaagaaaat 360
tttgttacct tccttctgta attttttttt aagtttgaaa tttacaaagc caatggatgg 420
ctaagattaa tttctgactt ttttttggat acataccatt tatttatgta aatgtgctca 480

```
tgtatgtata tatttatcta tgcattttgg aaaaagaata tttgtactaa attatttgat    540

aaataattgt agtaattata cttaaacact ctggtc                              576


<210> SEQ ID NO 292
<211> LENGTH: 782
<212> TYPE: DNA
<213> ORGANISM: Nezara viridula

<400> SEQUENCE: 292

gaggtttcag tttctgcaca gtccagtgac tttggtttcg atcgggattt atatctctat     60

tatggacaat ttgggtcaac aaacacctca tcaaaataat cattcaaatg atacagaaat    120

gaacaatttt atggacgtat ccagaatgag taccatgtgg ccttatccac atcctgacag    180

gttttcacaa tacagggatt tctttcatga acctcagcaa ggagtagttt ctgggaatga    240

aacaacaaat aatgttagcc aagtattaac aaacaattcc acacagcaac attctttagt    300

gaatactatg cctgttatgg gaactttaca aacagtatta actcaaggtt tgccaaacca    360

aaatgctaat gctaatgttg ttaatttaaa tcatactcca cagaatttac ccagtactat    420

tcagacttcc ataaatagcc ttccaaatgc caccaactct accagtcaag gacaagagca    480

atctacccag atattaacaa gaatgaggtt gcaagatttg gtgagagaag tagatcctaa    540

tgaacaatta gacgaagatg ttgaagatgt attattacaa atggcagatg attttgttga    600

ctcagcaatt acagctggtt gtcttcttgc caagcacaga aaatcaacta ctgtagaagt    660

taaggatctt cagctacatt tagaaagaaa ttggaatatg tggatacctg gttttggaac    720

agatgaattg cgaccttaca aacgtgcatc tgttacagaa gctcataaac aaagacttac    780

gc                                                                   782


<210> SEQ ID NO 293
<211> LENGTH: 1358
<212> TYPE: DNA
<213> ORGANISM: Artificial Sequence
<220> FEATURE:
<223> OTHER INFORMATION: PHP49713 Haripin RNA Construct without promoter

<400> SEQUENCE: 293

ggaaatatgt agtaggaaca aaagtcagtt aagtagtatg ctctctgcaa tcttggacta     60

taccagcaat aaaaacttta tcattagaga taaaaaagat atatcatttt tttctaaagc    120

tatggaagtt tgtagtaaac tcaaagataa ggatcttctc tacaggcttc atgaattatt    180

gttgaccgga aacaattata atttgatcgg agattcattt agtgaatcgg tgtattaccg    240

ttattttttt ttatttgctt actgatactg aagaacttag taaagtaatg gaattctatg    300

atgaccttgt accaaacgtt tatgttccag agccatcagt gaccaatgct atattgaaag    360

ctgtttgtaa caacatggca tgggaccttc ttcccaagct ttggccagac atactattgt    420

ttgagcagta tgaagtttcc ggtgtcctgg aaaatatttt agatattgca tctcaaaatg    480

aaggcaagaa tttgatggaa gggatgtcta aaattgcatg gtctgcatgg gagaagcaac    540

tttattatac aaagttgata gatatcggtc cgagatccat caggtaagtt tctgcttcta    600

cctttgatat atatataata attatcatta attagtagta atataatatt tcaaatattt    660

ttttcaaaat aaaagaatgt agtatatagc aattgctttt ctgtagttta taagtgtgta    720

tattttaatt tataactttt ctaatatatg accaaaacat ggtgatgtgc aggtccatgg    780

tggagctcga ccgatatcta tcaactttgt ataataaagt tgcttctccc atgcagacca    840
```

```
tgcaatttta gacatccctt ccatcaaatt cttgccttca ttttgagatg caatatctaa    900

aatattttcc aggacaccgg aaacttcata ctgctcaaac aatagtatgt ctggccaaag    960

cttgggaaga aggtcccatg ccatgttgtt acaaacagct ttcaatatag cattggtcac   1020

tgatggctct ggaacataaa cgtttggtac aaggtcatca tagaattcca ttactttact   1080

aagttcttca gtatcagtaa gcaaataaaa aaaaataacg gtaatacacc gattcactaa   1140

atgaatctcc gatcaaatta taattgtttc cggtcaacaa taattcatga agcctgtaga   1200

gaagatcctt atctttgagt ttactacaaa cttccatagc tttagaaaaa aatgatatat   1260

ctttttatc tctaatgata aagtttttat tgctggtata gtccaagatt gcagagagca   1320

tactacttaa ctgactttg ttcctactac atatttcc                              1358
```

```
<210> SEQ ID NO 294
<211> LENGTH: 1498
<212> TYPE: DNA
<213> ORGANISM: Artificial Sequence
<220> FEATURE:
<223> OTHER INFORMATION: PHP48181 Haripin RNA Construct without promoter

<400> SEQUENCE: 294

ctgcggcata tagcctgctg cagttaatgc gggaaggttt accttattat gtctgactgg     60

gaacaaagat tgctcagcct ggaaaaactg gacaggtcat cgccagagct ctggccagag    120

ccgatacctg ggtgacagaa atatgctgct cgcaatgctc tttctagttc ctctgttcca    180

aagaacattg aatcactcca gagtcagttt actgaggatg actataagct gctaaattat    240

tacagtactc tttctaaaga atctctgatt caagaattaa agaagcttca tgaccaggcc    300

tataaattag gtcttgaaga agccaaggaa atgactagag gaagattttt gaacatactg    360

tctaccagaa aaaagtaatg gtttgtaaat gctgccatgc ttctgaatgg ttccatcata    420

ttctgatcca gaagaaggaa gttgtagcga atggagtagg tataaaagtg agtcaataag    480

gacaagaagg gctaatttaa tgtatttttc caaatatttt tgtaattgca gaatagaaga    540

tttatgtgaa gaaatgaatt taagtttttg ttgttgtaac tgtctgttat agttccttca    600

gtcccacaac tttattatac aaagttgata gatatcggtc cgagatccat caggtaagtt    660

tctgcttcta cctttgatat atatataata attatcatta attagtagta atataatatt    720

tcaaatattt ttttcaaaat aaaagaatgt agtatatagc aattgctttt ctgtagttta    780

taagtgtgta tattttaatt tataactttt ctaatatatg accaaaacat ggtgatgtgc    840

aggtccatgg tggagctcga ccgatatcta tcaactttgt ataataaagt tgtgggactg    900

aaggaactat aacagacagt tacaacaaca aaaacttaaa ttcatttctt cacataaatc    960

ttctattctg caattacaaa aatatttgga aaaatacatt aaattagccc ttcttgtcct   1020

tattgactca cttttatacc tactccattc gctacaactt ccttcttctg gatcagaata   1080

tgatggaacc attcagaagc atggcagcat ttacaaacca ttactttttt ctggtagaca   1140

gtatgttcaa aaatcttcct ctagtcattt ccttggcttc ttcaagacct aatttatagg   1200

cctggtcatg aagcttcttt aattcttgaa tcagagattc tttagaaaga gtactgtaat   1260

aatttagcag cttatagtca tcctcagtaa actgactctg gagtgattca atgttctttg   1320

gaacagagga actagaaaga gcattgcgag cagcatattc tgtcacccca ggtatcggct   1380

ctggccagag ctctggcgat gacctgtcca gtttttccag gctgagcaat ctttgttccc   1440

agtcagacat aataaggtaa accttcccgc attaactgca gcaggctata tgccgcag     1498
```

<210> SEQ ID NO 295
<211> LENGTH: 1813
<212> TYPE: DNA
<213> ORGANISM: Artificial Sequence
<220> FEATURE:
<223> OTHER INFORMATION: pKB505 Haripin RNA Construct without promoter

<400> SEQUENCE: 295
ctgcggcata tagcctgctg cagttaatgc gggaaggttt accttattat gtctgactgg 60
gaacaaagat tgctcagcct ggaaaaactg gacaggtcat cgccagagct ctggccagag 120
ccgatacctg ggtgacagaa atatgctgct cgcaatgctc tttctagttc ctctgttcca 180
aagaacattg aatcactcca gagtcagttt actgaggatg actataagct gctaaattat 240
tacagtactc tttctaaaga atctctgatt caagaattaa agaagcttca tgaccaggcc 300
tataaattag gtcttgaaga agccaaggaa atgactagag gaagattttt gaacatactg 360
tctaccagaa aaaagtaatg gtttgtaaat gctgccatgc ttctgaatgg ttccatcata 420
ttctgatcca gaagaaggaa gttgtagcga atggagtagg tataaaagtg agtcaataag 480
gacaagaagg gctaatttaa tgtatttttc caaatatttt tgtaattgca gaatagaaga 540
tttatgtgaa gaaatgaatt taagtttttg ttgttgtaac tgtctgttat agttccttca 600
gtcccaaata ttttgttggc ttctaatcaa gctcttgtat ttattaattt tctttttcaa 660
ttcaattaat taaagtgttg ctaaaaagtt gataatatta aagtaaattt agtttatttt 720
tatttcccag aattaattat ttattattgt tatctgtact aagcaacttt attatacaaa 780
gttggataga tatcggtccg agatccatca ggtaagtttc tgcttctacc tttgatatat 840
atataataat tatcattaat tagtagtaat ataatatttc aaatattttt ttcaaaataa 900
aagaatgtag tatatagcaa ttgcttttct gtagtttata agtgtgtata ttttaattta 960
taacttttct aatatatgac caaaacatgg tgatgtgcag gtccatggtg gagctcgacc 1020
gatatctatc aactttgtat aataaagttg cttagtacag ataacaataa taaataatta 1080
attctgggaa ataaaaataa actaaattta ctttaatatt atcaactttt tagcaacact 1140
ttaattaatt gaattgaaaa agaaaattaa taaatacaag agcttgatta gaagccaaca 1200
aaatatttgg gactgaagga actataacag acagttacaa caacaaaaac ttaaattcat 1260
ttcttcacat aaatcttcta ttctgcaatt acaaaaatat ttggaaaaat acattaaatt 1320
agcccttctt gtccttattg actcactttt atacctactc cattcgctac aacttccttc 1380
ttctggatca gaatatgatg gaaccattca gaagcatggc agcatttaca aaccattact 1440
tttttctggt agacagtatg ttcaaaaatc ttcctctagt catttccttg gcttcttcaa 1500
gacctaattt ataggcctgg tcatgaagct tctttaattc ttgaatcaga gattctttag 1560
aaagagtact gtaataattt agcagcttat agtcatcctc agtaaactga ctctggagtg 1620
attcaatgtt ctttggaaca gaggaactag aaagagcatt gcgagcagca tattctgtca 1680
ccccaggtat cggctctggc cagagctctg gcgatgacct gtccagtttt tccaggctga 1740
gcaatctttg ttcccagtca gacataataa ggtaaacctt cccgcattaa ctgcagcagg 1800
ctatatgccg cag 1813

<210> SEQ ID NO 296
<211> LENGTH: 1694
<212> TYPE: DNA
<213> ORGANISM: Artificial Sequence
<220> FEATURE:
<223> OTHER INFORMATION: pKB506 Haripin RNA Construct without promoter

<400> SEQUENCE: 296

```
gggtgattgc ggttacatca tgtacggaaa aataattcta atccttgatt taaatttgaa     60

cttgactatt tatttattct ttatttcatt ttgtaaatca ttttatgtat ctcctggcaa    120

gcaattttat ccaccttgca ccaacacctt cgggttccat aatcaaacca ccttaacttc    180

acaccatgct gtaactcaca ccgcccagca tctccaatgt gaaagaagct aaaatttaat    240

aaacaatcat acgaagcagt gacaaaatac cagatggtat taatgcttcg ataaaattaa    300

ttggaaagta taaaatggta gaaaataata aattataatt aatttaagta agataaaaaa    360

taattaaaaa ctaaaatgtt aaaattttaa aaaaattatt ttaaataata tttaaaaaca    420

ttaaaaatca ttttaaaaaa tttatttata gaacaattaa ataaatattt cagctaataa    480

aaaacaaaag cttacctagc cttagaagac aacttgtcca acaattagat gatacccatt    540

gcccttacgt tttctttaac atcaattatt gtttttgtca acaagctatc ttttagtttt    600

attttattgg taaaaaatat gtcgccttca agttgcatca tttaacacat ctcgtcatta    660

gaaaaataaa actcttccct aaacgattag tagaaaaaat cattcgataa taaataagaa    720

agaaaaatta gaaaaaaata acttcatttt aaaaaaatca ttaaggctat attttttaaa    780

tgactaattt tatatagact gtaactaaaa gtatacaatt tattatgcta tgtatcttaa    840

agaattactt ataaaaatct acggaagaat atcttacaaa gtgaaaaaca aatgagaaag    900

aatttagtgg gatgattatg attttatttg aaaattgaaa aaataattat taaagacttt    960

agtggagtaa gaaagctttc ctattagtct tttcttatcc ataaaaaaaa aaaaaaaaat   1020

ctagcgtgac agcttttcca tagattttaa taatgtaaaa tactggtagc agccgaccgt   1080

tcaggtaatg gacactgtgg tcctaacttg caacgggtgc gggcccaatt taataacgcc   1140

gtggtaacgg ataaagccaa gcgtgaagcg gtgaaggtac atctctgact ccgtcaagat   1200

tacgaaaccg tcaactacga aggactcccc gaaatatcat ctgtgtcata aacaccaagt   1260

cacaccatac atgggcacgc gtcacaatat gattggagaa cggttccacc gcatatgcta   1320

taaaatgccc ccacacccct cgaccctaat cgcacttcaa ttgcaatcaa attagttcat   1380

tctctttgcg cagttcccta cctctccttt caaggttcgt agatttcttc cgtttttttt   1440

tcttcttctt tattgtttgt tctacatcag catgatgttg atttgattgt gttttctatc   1500

gtttcatcga ttataaattt tcataatcag aagattcagc ttttattaat gcaagaacgt   1560

ccttaattga tgattttata accgtaaatt aggtctaatt agagtttttt tcataaagat   1620

tttcagatcc gtttacaaca agccttaatt gttgattctg tagtcgtaga ttaaggtttt   1680

tttcatgaac tact                                                     1694
```

<210> SEQ ID NO 297
<211> LENGTH: 1256
<212> TYPE: DNA
<213> ORGANISM: Artificial Sequence
<220> FEATURE:
<223> OTHER INFORMATION: PHP48183 Haripin RNA Construct without promoter
<220> FEATURE:
<221> NAME/KEY: misc_feature
<222> LOCATION: 432, 825
<223> OTHER INFORMATION: n = A,T,C or G

<400> SEQUENCE: 297

```
tgccgagaaa tacaaggctg aagatgataa gcagaaagct gtcattcaag ctaagaacac     60

tctggagtcc tattgtttca atatgaaatc tactgtagag gatgaaaaac tgaaagacaa    120

aatttccgat tctgataaaa ctacaatttt ggagaaatgt aatgaagtta ttcgctggct    180
```

```
cgatgctaat cagttagctg aaaaagaaga attcgaacat aagcaaaagg aattggaagc    240

catatgcaat cctattatta ctaaattgta ccaaagtggt ggtatgcccg gaggaatgcc    300

aggtggtatg cctggtggtt tcccaggcgg tgcccctcct aatgctggtg gtgctgctgg    360

acctaccatt gaagaagttg attaaacatt ccatgcgaat aaacacacaa ataatacatt    420

gtataattaa tnctagttga attgcaattt ttttttcctt tctagtcaag agaccttcaa    480

atggccaact ttattataca aagttgatag atatcggtcc gagatccatc aggtaagttt    540

ctgcttctac ctttgatata tatataataa ttatcattaa ttagtagtaa tataatattt    600

caaatatttt tttcaaaata aaagaatgta gtatatagca attgcttttc tgtagtttat    660

aagtgtgtat attttaattt ataacttttc taatatatga ccaaaacatg gtgatgtgca    720

ggtccatggt ggagctcgac cgatatctat caactttgta taataaagtt ggccatttga    780

aggtctcttg actagaaagg aaaaaaaaat tgcaattcaa ctagnattaa ttatacaatg    840

tattatttgt gtgtttattc gcatggaatg tttaatcaac ttcttcaatg gtaggtccag    900

cagcaccacc agcattagga ggggcaccgc ctgggaaacc accaggcata ccacctggca    960

ttcctccggg cataccacca ctttggtaca atttagtaat aataggattg catatggctt   1020

ccaattcctt ttgcttatgt tcgaattctt ctttttcagc taactgatta gcatcgagcc   1080

agcgaataac ttcattacat ttctccaaaa ttgtagtttt atcagaatcg gaaattttgt   1140

ctttcagttt ttcatcctct acagtagatt tcatattgaa acaataggac tccagagtgt   1200

tcttagcttg aatgacagct ttctgcttat catcttcagc cttgtatttc tcggca       1256
```

<210> SEQ ID NO 298
<211> LENGTH: 1188
<212> TYPE: DNA
<213> ORGANISM: Artificial Sequence
<220> FEATURE:
<223> OTHER INFORMATION: pKB508 Haripin RNA Construct without promoter

<400> SEQUENCE: 298

```
ctagtcaaga gaccttcaaa tggccttgta tttttgttta aaaatttaat gttaataatg     60

taacttttac aagtattttg tttatttata attttttttat atgttctgtc attggtatca    120

atgaattata ttagagttac tattaactaa tgtttttaaa taaaaatata gcctgtagag    180

gaatacttga tgtaaatgta tacagtatta aatgagccat ataattttta tttaaattcc    240

attttttttaa tttatatatt gataaattgc attttgtgtg ttatacttgc ctcattgaat    300

ttatgttaat gaatattttt tatagttaaa aaaaaaggct gattccaatt taagttttat    360

tttgaagaag aattttgtac ccttgtttga taaatcttgt gaatcttgtt atggttaaac    420

atcttttggt aaccaccctt tggttgtatt ccaactttat tatacaaagt tgatagatat    480

cggtccgaga tccatcaggt aagtttctgc ttctaccttt gatatatata taataattat    540

cattaattag tagtaatata atatttcaaa tattttttttc aaaataaaag aatgtagtat    600

atagcaattg cttttctgta gtttataagt gtgtatattt taatttataa cttttctaat    660

atatgaccaa aacatggtga tgtgcaggtc catggtggag ctcgaccgat atctatcaac    720

tttgtataat aaagttggaa tacaaccaaa gggtggttac caaaagatgt ttaaccataa    780

caagattcac aagatttatc aaacaagggt acaaaattct tcttcaaaat aaaacttaaa    840

ttggaatcag cctttttttt taactataaa aaatattcat taacataaat tcaatgaggc    900

aagtataaca cacaaaatgc aatttatcaa tatataaatt aaaaaaaatgg aatttaaata    960
```

```
aaaattatat ggctcattta atactgtata catttacatc aagtattcct ctacaggcta   1020

tatttttatt taaaaacatt agttaatagt aactctaata taattcattg ataccaatga   1080

cagaacatat aaaaaaatta taaataaaca aaatacttgt aaaagttaca ttattaacat   1140

taaattttta aacaaaaata caaggccatt tgaaggtctc ttgactag               1188


<210> SEQ ID NO 299
<211> LENGTH: 1882
<212> TYPE: DNA
<213> ORGANISM: Artificial Sequence
<220> FEATURE:
<223> OTHER INFORMATION: PHP49450 Haripin RNA Construct without promoter

<400> SEQUENCE: 299

gtgtccgccc tcttcatctc ctgtcttgta tcatcacatc atccttcccc ttctctcgct     60

gagtcaactt acgccaaacc gtcatccagc ggtaggaagc gagaggctgc cctagattgt    120

atgctaggct ctctcaccga gaacatgtcc aggcaaggag tcacaacgac acagaaaggc    180

tgctgttcag cttgcgacaa acccattgtc ggccaggtaa tcacagcact aggcaagaca    240

tggcatccag aacactttgt ctgcacacac tgcaaccagg agcttggaac aagaaacttc    300

tttgagaggg atggtcaccc ctactgtgag ccagattacc acaacctctt cagtcctcga    360

tgtgcctact gcaacggccc tatcttagat aaatgtgtca cagccttgga aaaaacatgg    420

catacggaac atttcttttg tgctcagtgt ggtaaacagt ttggggaaga ggggttccat    480

gagaaagatg gtcgacccta ttgtcgggac gattactttg aaatgtttgc tccaaaatgt    540

ggcggctgtt cccgcccaat aatggagaac tatatttcag ccctctcaat gcagtggcat    600

caagactgtt ttgtctgcag ggattgccgg aagcccgtca cagggaagac cttttatgcc    660

atggaaggaa acctgtctgt ccgaaatgtg tcggagtgga cgaggaagaa gaagactgaa    720

gattcggcaa aaactaatac ctctatatta aatgcttttt tatagaacca cgcgaatcat    780

aaccaccatc ctaccaacca actttattat acaaagttga tagatatcgg tccgagatcc    840

atcaggtaag tttctgcttc tacctttgat atatatataa taattatcat taattagtag    900

taatataata tttcaaatat ttttttcaaa ataaaagaat gtagtatata gcaattgctt    960

ttctgtagtt tataagtgtg tatattttaa tttataactt ttctaatata tgaccaaaac   1020

atggtgatgt gcaggtccat ggtggagctc gaccgatatc tatcaacttt gtataataaa   1080

gttggttggt aggatggtgg ttatgattcg cgtggttcta taaaaaagca tttaatatag   1140

aggtattagt ttttgccgaa tcttcagtct tcttcttcct cgtccactcc gacacatttc   1200

ggacagacag gtttccttcc atggcataaa aggtcttccc tgtgacgggc ttccggcaat   1260

ccctgcagac aaaacagtct tgatgccact gcattgagag ggctgaaata tagttctcca   1320

ttattgggcg ggaacagccg ccacattttg gagcaaacat ttcaaagtaa tcgtcccgac   1380

aatagggtcg accatctttc tcatggaacc cctcttcccc aaactgttta ccacactgag   1440

cacaaaagaa atgttccgta tgccatgttt tttccaaggc tgtgacacat ttatctaaga   1500

tagggccgtt gcagtaggca catcgaggac tgaagaggtt gtggtaatct ggctcacagt   1560

aggggtgacc atccctctca aagaagtttc ttgttccaag ctcctggttg cagtgtgtgc   1620

agacaaagtg ttctggatgc catgtcttgc ctagtgctgt gattacctgg ccgacaatgg   1680

gtttgtcgca agctgaacag cagcctttct gtgtcgttgt gactccttgc ctggacatgt   1740

tctcggtgag agagcctagc atacaatcta gggcagcctc tcgcttccta ccgctggatg   1800

acggtttggc gtaagttgac tcagcgagag aaggggaagg atgatgtgat gatacaagac   1860
```

aggagatgaa gagggcggac ac 1882

<210> SEQ ID NO 300
<211> LENGTH: 1438
<212> TYPE: DNA
<213> ORGANISM: Artificial Sequence
<220> FEATURE:
<223> OTHER INFORMATION: PHP49451 Haripin RNA Construct without promoter

<400> SEQUENCE: 300
ttcctggagc aggtggtgga attggttcag caagacctgc gggacgtgga gttccagctc 60
ctggtacacc agctgcacct ggtctccaag gtccagttcg tggtgtaggt ggcccatctg 120
cacaagttat gactccagcg gggcgtggag gacaagtttc tgctcctcct cagatgcgtg 180
ctccaccccc aggaatgccc ccaatgatgg gagctccacc aatgatgaac atggcaccag 240
gaatggcgat gggaagaggt ggaccacctc ctcaaatggg tgctcctcca gctccaccaa 300
tgcgaggtcc cccaccagga atgatgagag gtccccctcc tttttaagaa gaaagaaaat 360
tttgttacct tccttctgta attttttttt aagtttgaaa tttacaaagc caatggatgg 420
ctaagattaa tttctgactt ttttttggat acataccatt tatttatgta aatgtgctca 480
tgtatgtata tatttatcta tgcattttgg aaaaagaata tttgtactaa attatttgat 540
aaataattgt agtaattata cttaaacact ctggtccaac tttattatac aaagttgata 600
gatatcggtc cgagatccat caggtaagtt tctgcttcta cctttgatat atatataata 660
attatcatta attagtagta atataatatt tcaaatattt ttttcaaaat aaaagaatgt 720
agtatatagc aattgctttt ctgtagttta taagtgtgta tattttaatt tataactttt 780
ctaatatatg accaaaacat ggtgatgtgc aggtccatgg tggagctcga ccgatatcta 840
tcaactttgt ataataaagt tggaccagag tgtttaagta taattactac aattatttat 900
caaataattt agtacaaata ttcttttttcc aaaatgcata gataaatata tacatacatg 960
agcacattta cataaataaa tggtatgtat ccaaaaaaaa gtcagaaatt aatcttagcc 1020
atccattggc tttgtaaatt tcaaacttaa aaaaaaatta cagaaggaag gtaacaaaat 1080
tttctttctt cttaaaaagg agggggacct ctcatcattc ctggtggggg acctcgcatt 1140
ggtggagctg gaggagcacc catttgagga ggtggtccac ctcttcccat cgccattcct 1200
ggtgccatgt tcatcattgg tggagctccc atcattgggg gcattcctgg gggtggagca 1260
cgcatctgag gaggagcaga aacttgtcct ccacgccccg ctggagtcat aacttgtgca 1320
gatgggccac ctacaccacg aactggacct tggagaccag gtgcagctgg tgtaccagga 1380
gctggaactc cacgtcccgc aggtcttgct gaaccaattc caccacctgc tccaggaa 1438

<210> SEQ ID NO 301
<211> LENGTH: 1850
<212> TYPE: DNA
<213> ORGANISM: Artificial Sequence
<220> FEATURE:
<223> OTHER INFORMATION: PHP49480 Haripin RNA Construct without promoter

<400> SEQUENCE: 301
gaggtttcag tttctgcaca gtccagtgac tttggtttcg atcgggattt atatctctat 60
tatggacaat ttgggtcaac aaacacctca tcaaaataat cattcaaatg atacagaaat 120
gaacaatttt atggacgtat ccagaatgag taccatgtgg ccttatccac atcctgacag 180
gttttcacaa tacagggatt tctttcatga acctcagcaa ggagtagttt ctgggaatga 240

```
aacaacaaat aatgttagcc aagtattaac aaacaattcc acacagcaac attctttagt    300

gaatactatg cctgttatgg gaactttaca aacagtatta actcaaggtt tgccaaacca    360

aaatgctaat gctaatgttg ttaatttaaa tcatactcca cagaatttac ccagtactat    420

tcagacttcc ataaatagcc ttccaaatgc caccaactct accagtcaag gacaagagca    480

atctacccag atattaacaa gaatgaggtt gcaagatttg gtgagagaag tagatcctaa    540

tgaacaatta gacgaagatg ttgaagatgt attattacaa atggcagatg attttgttga    600

ctcagcaatt acagctggtt gtcttcttgc caagcacaga aaatcaacta ctgtagaagt    660

taaggatctt cagctacatt tagaaagaaa ttggaatatg tggatacctg gttttggaac    720

agatgaattg cgaccttaca aacgtgcatc tgttacagaa gctcataaac aaagacttac    780

gccaacttta ttatacaaag ttgatagata tcggtccgag atccatcagg taagtttctg    840

cttctacctt tgatatatat ataataatta tcattaatta gtagtaatat aatatttcaa    900

atattttttt caaaataaaa gaatgtagta tatagcaatt gcttttctgt agtttataag    960

tgtgtatatt ttaatttata acttttctaa tatatgacca aaacatggtg atgtgcaggt   1020

ccatggtgga gctcgaccga tatctatcaa ctttgtataa taaagttggc gtaagtcttt   1080

gtttatgagc ttctgtaaca gatgcacgtt tgtaaggtcg caattcatct gttccaaaac   1140

caggtatcca catattccaa tttctttcta aatgtagctg aagatcctta acttctacag   1200

tagttgattt tctgtgcttg gcaagaagac aaccagctgt aattgctgag tcaacaaaat   1260

catctgccat ttgtaataat acatcttcaa catcttcgtc taattgttca ttaggatcta   1320

cttctctcac caaatcttgc aacctcattc ttgttaatat ctgggtagat tgctcttgtc   1380

cttgactggt agagttggtg gcatttggaa ggctatttat ggaagtctga atagtactgg   1440

gtaaattctg tggagtatga tttaaattaa caacattagc attagcattt tggtttggca   1500

aaccttgagt taatactgtt tgtaaagttc ccataacagg catagtattc actaaagaat   1560

gttgctgtgt ggaattgttt gttaatactt ggctaacatt atttgttgtt tcattcccag   1620

aaactactcc ttgctgaggt tcatgaaaga aatccctgta ttgtgaaaac ctgtcaggat   1680

gtggataagg ccacatggta ctcattctgg atacgtccat aaaattgttc atttctgtat   1740

catttgaatg attattttga tgaggtgttt gttgacccaa attgtccata atagagatat   1800

aaatcccgat cgaaaccaaa gtcactggac tgtgcagaaa ctgaaacctc              1850


<210> SEQ ID NO 302
<211> LENGTH: 643
<212> TYPE: DNA
<213> ORGANISM: Nezara viridula

<400> SEQUENCE: 302

cagagtgaaa tcgctccact gagagtgtcg gtctcttgtc gctccgtttg atcgctcgta     60

cgtacgcggt attatatacg ggccgagtgt ggcgttggac atggtactta catcgaacat    120

ctttaaagga ctttctgttt aagagaggag gagaggagga cacatggcga ccctgcggcc    180

gcacttcgtc acccacaacg gccccccaga cctgtccgac gatggcactg acgatgaggg    240

gacgccgctc acccacgata tctatggcgg aagtacaagg actgttcagg agacaaaagg    300

atgggatgtg ttccgagttc ttcccccaaa aacagattcg ggttcgatgg aaaaccaagc    360

atgtcttgaa ttcactgtga gaattttaaa aattatagca tacctggtta cgttcactat    420

tgtcctcacc agtggtgtat tggctaagct gtcagttctc ttcatcactt cccaactgcg    480

acctgatagg gtggtcagtt attgtaataa ggacttggga agggataagc aattcgtagt    540
```

gaacttacca cccgaagaac gagtggcctg gtcatggtgc ttactatttg cttttgcaat 600
tcctgaagtt ggaacattca ttaggtccct gagaatatgt atc 643

<210> SEQ ID NO 303
<211> LENGTH: 1219
<212> TYPE: DNA
<213> ORGANISM: Nezara viridula

<400> SEQUENCE: 303
aggttatgtg actgtgttac atcgagtttg atattgtttt cattgtgaag tgttgattag 60
ttctgtatta cttcgaagtt taaagaatta ttaatatact ttagaaatgt tgaattttgg 120
ttataatgct agaagatata tttatgtttt catatttact atgcctctta cttagtactg 180
atgttacata ggaaaatgag agttaaaaaa tatttgcctg atgtgtacat ttgtggaaga 240
aaatttaatt ctagaaaatg gctgctctgt ttgacccaaa tgacagaagc aggtaagttc 300
atgaaattgg tattttggtc aaatgtcaag gcaagatgcc actgatcttt taatgggaga 360
aaaggagggt ggcgtatttc ttgtccgtga tagtatctca attcatggtg attatgttct 420
ttgtgtaagg gaagatagta aagtaagcca ttatattatc aacaaaattc agcagaatga 480
tcaaattaag tacagaattg gtgatcaaac atttaatgat ttgcccagtt agctatcttt 540
ctataaattg cactatttag atactacacc tctaattcga ccagcaccaa agagagttga 600
aaaagtgata gctaaatttg acttcaatgg aagtgatcaa gatgatttac cgtttaagaa 660
aggtgatatt ttaacaatta tttctaaaga tgaagatcag tggtggacag ccaaaaacag 720
tgctggttta atgggatcaa taccagttcc ctatattcaa aagtataatg accaagatgt 780
actagcagat cttggttctt catttgttga taatagtcct cctagtggaa gtcatgtaga 840
acctataaga agatctaatg ttcagaggaa gcttcctgcg tttgcgaaag taaaacaggc 900
cagagctcca aatgcttatg acaagacagc tttaaagcta gaaattggtg aaataataaa 960
agttacaaaa atgaatttaa atggacagtg ggaaggtgaa cttaagggaa aaactggaca 1020
ttttccgttt actcatgttg aattcataga taatgaaatg tgaatgctgc aattttttta 1080
acaaatagta caaacataat tcatggctat tgttcattat tggtgctcta atgaaaattt 1140
tattaatgca cttctgctat ttataaaaca tattattatt ttttgtaaag cattaaactt 1200
atgttattca atttacagc 1219

<210> SEQ ID NO 304
<211> LENGTH: 1470
<212> TYPE: DNA
<213> ORGANISM: Nezara viridula

<400> SEQUENCE: 304
actcaaaatg atagcacttt gtgatttatt ctatatgtca tccaatcttt aatttactgg 60
acgattgcta aaataagttt cagaaatatt tgtctgtaat aacattaatt gctcaattat 120
agaaataaag ctactaatta gcctataata tctaacatat atctaaaaaa ttagatatat 180
gttgaaccct aagtattgta aacatcagca tgttatacaa taaattaata acagaaaaca 240
ttcttacttc taaacagaat gaaaatatag agtacttgtg atttagccgg tcgccttcgg 300
acctaccttc ttatcttgtg ttatctcttc gtatcgctca tctctgctta gttacttgtg 360
cgttcttctt gttattcaat tattttcagt tttttttgt tttgttattt tttatttaaa 420
atggttacaa taacacttta ggaattactg tcttcggaag aagactatat tatatattag 480

```
acaggtcaac taaaaaaatt ggagggtcta aaaaagttgt tgaaatagac ggaagtcttt    540

tttctaaacg aaaaaatcat gtagggagag tgctctcgga ataatggatg tttggcagag    600

tttgtcgaga aacagatgag tgtttcattg taaaaataaa agaaacgcaa caattctatt    660

tactaattga taatatctct cttctatatt atcttctaaa aataatatag aagaaagaaa    720

cactatatat tctgactgtt ggagaggata taaaacctaa gaactaaata aagcgaacta    780

aaaccatttc caggtgaatc actggtatag ctttgtcgat ccacactcaa cacatagaac    840

tattatgggg ctcagctaag tggaggaata aaatatatcg aggaactgcg atgctactcc    900

gggattcata tatttagcta ctgcagtaca caaaatcata tttatgtgaa tttttgtggc    960

gatgggtgca cagagaagag acgtgttcct cgctatttta actagcatta agctattttg   1020

tcttccaaaa tgaataaaat gttgtaaaat aaaagagttt tgttattatt acatttctgt   1080

ttgtttattt caatttccat aattataaat aaggaggtag gtgttatcag tgttcagatt   1140

ataaataatg atggatagca gtacgtggtg accagttaac tcacaagtgc caaatatagc   1200

actggtttaa ctgtttgtga tctgaggtag aagaattaat aagaagtcta catattctcc   1260

caccataagt taatataatc acctagtgtg tatcttcaat tagaacttca gaaggaagat   1320

ccagcaataa tgagatgagc ataattttag ttgaaatgga agaaataggc gaagcctatc   1380

aaaaatcaaa ctttattttc taatgatgta gatatgggca gataatttgt ttagggaaga   1440

ggttcatgga tcaattacgt aatttgtatg                                    1470


<210> SEQ ID NO 305
<211> LENGTH: 21
<212> TYPE: DNA
<213> ORGANISM: Nezara viridula

<400> SEQUENCE: 305

taagtaccat gtccaacgcc a                                               21


<210> SEQ ID NO 306
<211> LENGTH: 21
<212> TYPE: DNA
<213> ORGANISM: Nezara viridula

<400> SEQUENCE: 306

tattacaata actgaccacc c                                               21


<210> SEQ ID NO 307
<211> LENGTH: 21
<212> TYPE: DNA
<213> ORGANISM: Nezara viridula

<400> SEQUENCE: 307

tcctactaca tatttccacc c                                               21


<210> SEQ ID NO 308
<211> LENGTH: 21
<212> TYPE: DNA
<213> ORGANISM: Nezara viridula

<400> SEQUENCE: 308

tattccttct atcttctccc a                                               21


<210> SEQ ID NO 309
<211> LENGTH: 21
<212> TYPE: DNA
<213> ORGANISM: Nezara viridula
```

<400> SEQUENCE: 309
taaagtatat taataattct t 21

<210> SEQ ID NO 310
<211> LENGTH: 21
<212> TYPE: DNA
<213> ORGANISM: Nezara viridula

<400> SEQUENCE: 310
ttactatctt cccttacaca a 21

<210> SEQ ID NO 311
<211> LENGTH: 21
<212> TYPE: DNA
<213> ORGANISM: Nezara viridula

<400> SEQUENCE: 311
tacgaagaga taacacaaga t 21

<210> SEQ ID NO 312
<211> LENGTH: 21
<212> TYPE: DNA
<213> ORGANISM: Nezara viridula

<400> SEQUENCE: 312
taacaaaaca aaaaaaaact g 21

<210> SEQ ID NO 313
<211> LENGTH: 21
<212> TYPE: DNA
<213> ORGANISM: Nezara viridula

<400> SEQUENCE: 313
tggcgttgga ctaggtactt t 21

<210> SEQ ID NO 314
<211> LENGTH: 21
<212> TYPE: DNA
<213> ORGANISM: Nezara viridula

<400> SEQUENCE: 314
gggtggtcag tatttgtaat t 21

<210> SEQ ID NO 315
<211> LENGTH: 21
<212> TYPE: DNA
<213> ORGANISM: Nezara viridula

<400> SEQUENCE: 315
gggtggaaat aattagtagg t 21

<210> SEQ ID NO 316
<211> LENGTH: 21
<212> TYPE: DNA
<213> ORGANISM: Nezara viridula

<400> SEQUENCE: 316
tgggagaaga tcaaaggaat t 21

<210> SEQ ID NO 317
<211> LENGTH: 21
<212> TYPE: DNA

<213> ORGANISM: Nezara viridula

<400> SEQUENCE: 317
aagaattatt ataatacttt t 21

<210> SEQ ID NO 318
<211> LENGTH: 21
<212> TYPE: DNA
<213> ORGANISM: Nezara viridula

<400> SEQUENCE: 318
ttgtgtaagg gttgatagta t 21

<210> SEQ ID NO 319
<211> LENGTH: 21
<212> TYPE: DNA
<213> ORGANISM: Nezara viridula

<400> SEQUENCE: 319
atcttgtgtt aaatcttcgt t 21

<210> SEQ ID NO 320
<211> LENGTH: 21
<212> TYPE: DNA
<213> ORGANISM: Nezara viridula

<400> SEQUENCE: 320
cagttttttt tgcttttgtt t 21

<210> SEQ ID NO 321
<211> LENGTH: 976
<212> TYPE: DNA
<213> ORGANISM: Artificial Sequence
<220> FEATURE:
<223> OTHER INFORMATION: amiRNA precursor sequence #1 for inv1c.pk005.
h23.f

<400> SEQUENCE: 321
ctaggtaaac catggttcta gctagctagg gtttgggtag tgagtgtaat aaagttgcaa 60
agtttttggt taggttacgt tttgacctta ttattatagt tcaaagggaa acattaatta 120
aaggggatta tgaagtggcg ttggactagg tacttttgag gatcttactg ggtgaattga 180
gctgcttagc tatggatccc acagttctac ccatcaataa gtgcttttgt ggtagtcttg 240
tggcttccat atctggggag cttcatttgc ctttatagta ttaaccttct aagtaccatg 300
tccaacgcca cacccttctc ttcttttctc tcataataat ttaaatttgt tatagactct 360
aaactttaaa tgtttttttt gaagtttttc cgtttttctc ttttgccatg atcccgttct 420
tgctgtggag taaccttgtc cgaggtatgt gcatgattag atccatactt aatttgtgtg 480
catcacgaag gtgaggttga aatgaacttt gctttttga ccttttagga aagttctttt 540
gttgcagtaa tcaattttaa ttagttttaa ttgacactat tacttttatt gtcatctttg 600
ttagttttat tgttgaattg agtgcatatt tcgtaggaaa ttctcttacc taacattttt 660
tatacagatc tatgctcttg gctcttgccc ttactcttgg ccttgtgttg gttatttgtc 720
tacatattta ttgactggtc gatgagacat gtcacaattc ttgggcttat ttgttggtct 780
aataaaagga gtgcttattg aaagatcaag acggagattc ggttttatat aaataaacta 840
aagatgacat attagtgtgt tgatgtctct tcaggataat ttttgtttga aataatatgg 900
taatgtcttg tctaaatttg tgtacataat tcttactgat tttttggatt gttggatttt 960
tataaacaaa tctgtt 976

<210> SEQ ID NO 322
<211> LENGTH: 977
<212> TYPE: DNA
<213> ORGANISM: Artificial Sequence
<220> FEATURE:
<223> OTHER INFORMATION: amiRNA precursor sequence #2 for inv1c.pk005.
h23.f

<400> SEQUENCE: 322
ctaggtaaac catggattct agctagctag ggtttgggta gtgagtgtaa taaagttgca 60
aagtttttgg ttaggttacg ttttgacctt attattatag ttcaaaggga aacattaatt 120
aaaggggatt atgaaggggt ggtcagtatt tgtaatttga ggatcttact gggtgaattg 180
agctgcttag ctatggatcc cacagttcta cccatcaata agtgcttttg tggtagtctt 240
gtggcttcca tatctgggga gcttcatttg cctttatagt attaaccttc tattacaata 300
actgaccacc ccacccttct cttcttttct ctcataataa tttaaatttg ttatagactc 360
taaactttaa atgttttttt tgaagttttt ccgtttttct cttttgccat gatcccgttc 420
ttgctgtgga gtaaccttgt ccgaggtatg tgcatgatta gatccatact taatttgtgt 480
gcatcacgaa ggtgaggttg aaatgaactt tgcttttttg accttttagg aaagttcttt 540
tgttgcagta atcaatttta attagtttta attgacacta ttacttttat tgtcatcttt 600
gttagtttta ttgttgaatt gagtgcatat ttcgtaggaa attctcttac ctaacatttt 660
ttatacagat ctatgctctt ggctcttgcc cttactcttg gccttgtgtt ggttatttgt 720
ctacatattt attgactggt cgatgagaca tgtcacaatt cttgggctta tttgttggtc 780
taataaaagg agtgcttatt gaaagatcaa gacggagatt cggttttata taaataaact 840
aaagatgaca tattagtgtg ttgatgtctc ttcaggataa tttttgtttg aaataatatg 900
gtaatgtctt gtctaaattt gtgtacataa ttcttactga ttttttggat tgttggattt 960
ttataaacaa atctgtt 977

<210> SEQ ID NO 323
<211> LENGTH: 966
<212> TYPE: DNA
<213> ORGANISM: Artificial Sequence
<220> FEATURE:
<223> OTHER INFORMATION: amiRNA precursor sequence #1 for inv1c.pk004.
e6.f:fis

<400> SEQUENCE: 323
ctaggttcta gctagctagg gtttgggtag tgagtgtaat aaagttgcaa agtttttggt 60
taggttacgt tttgacctta ttattatagt tcaaagggaa acattaatta aaggggatta 120
tgaaggggtg gaaataatta gtaggttgag gatcttactg ggtgaattga gctgcttagc 180
tatggatccc acagttctac ccatcaataa gtgcttttgt ggtagtcttg tggcttccat 240
atctggggag cttcatttgc ctttatagta ttaaccttct cctactacat atttccaccc 300 caccccttctc ttcttttctc tcataataat ttaaatttgt tatagactct aaactttaaa 360
tgtttttttt gaagtttttc cgtttttctc ttttgccatg atcccgttct tgctgtggag 420
taaccttgtc cgaggtatgt gcatgattag atccatactt aatttgtgtg catcacgaag 480
gtgaggttga aatgaacttt gcttttttga ccttttagga aagttctttt gttgcagtaa 540
tcaattttaa ttagttttaa ttgacactat tacttttatt gtcatctttg ttagttttat 600
tgttgaattg agtgcatatt tcgtaggaaa ttctcttacc taacattttt tatacagatc 660

```
tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                                966
```

```
<210> SEQ ID NO 324
<211> LENGTH: 966
<212> TYPE: DNA
<213> ORGANISM: Artificial Sequence
<220> FEATURE:
<223> OTHER INFORMATION: amiRNA precursor sequence #2 for inv1c.pk004.
      e6.f:fis

<400> SEQUENCE: 324

ctaggttcta gctagctagg gtttgggtag tgagtgtaat aaagttgcaa agtttttggt     60

taggttacgt tttgacctta ttattatagt tcaaagggaa acattaatta aaggggatta    120

tgaagtggga gaagatcaaa ggaatttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct attccttcta tcttctccca    300

caccccttctc ttcttttctc tcataataat ttaaatttgt tatagactct aaactttaaa    360

tgtttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttgga cctttttagga aagttctttt gttgcagtaa    540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                                966
```

```
<210> SEQ ID NO 325
<211> LENGTH: 966
<212> TYPE: DNA
<213> ORGANISM: Artificial Sequence
<220> FEATURE:
<223> OTHER INFORMATION: amiRNA precursor sequence #1 for inv1c.pk004.
      e11.f:fis

<400> SEQUENCE: 325

ctaggttcta gctagctagg gtttgggtag tgagtgtaat aaagttgcaa agtttttggt     60

taggttacgt tttgacctta ttattatagt tcaaagggaa acattaatta aaggggatta    120

tgaagaagaa ttattataat actttttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct aaagtatatt aataattctt    300
```

```
cacccttctc ttcttttctc tcataataat ttaaatttgt tatagactct aaactttaaa    360

tgttttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttttagga aagttctttt gttgcagtaa    540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                                966
```

```
<210> SEQ ID NO 326
<211> LENGTH: 966
<212> TYPE: DNA
<213> ORGANISM: Artificial Sequence
<220> FEATURE:
<223> OTHER INFORMATION: amiRNA precursor sequence #2 for inv1c.pk004.
      e11.f:fis

<400> SEQUENCE: 326

ctaggttcta gctagctagg gtttgggtag tgagtgtaat aaagttgcaa agtttttggt     60

taggttacgt tttgacctta ttattatagt tcaaagggaa acattaatta aaggggatta    120

tgaagttgtg taagggttga tagtattgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct tactatcttc ccttacacaa    300

cacccttctc ttcttttctc tcataataat ttaaatttgt tatagactct aaactttaaa    360

tgttttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttttagga aagttctttt gttgcagtaa    540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                                966

<210> SEQ ID NO 327
<211> LENGTH: 966
<212> TYPE: DNA
<213> ORGANISM: Artificial Sequence
<220> FEATURE:
<223> OTHER INFORMATION: amiRNA precursor sequence #1 for inv1c.pk004.
      d17.f:fis

<400> SEQUENCE: 327
```

```
ctaggttcta gctagctagg gtttgggtag tgagtgtaat aaagttgcaa agtttttggt     60

taggttacgt tttgacctta ttattatagt tcaaagggaa acattaatta aaggggatta    120

tgaagatctt gtgttaaatc ttcgtttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct acgaagagat aacacaagat    300

cacccttctc ttcttttctc tcataataat ttaaatttgt tatagactct aaactttaaa    360

tgtttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttagga aagttctttt gttgcagtaa      540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

```
<210> SEQ ID NO 328
<211> LENGTH: 966
<212> TYPE: DNA
<213> ORGANISM: Artificial Sequence
<220> FEATURE:
<223> OTHER INFORMATION: amiRNA precursor sequence #2 for inv1c.pk004.
      d17.f:fis

<400> SEQUENCE: 328
```

```
ctaggttcta gctagctagg gtttgggtag tgagtgtaat aaagttgcaa agtttttggt     60

taggttacgt tttgacctta ttattatagt tcaaagggaa acattaatta aaggggatta    120

tgaagcagtt ttttttgctt ttgttttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct aacaaaacaa aaaaaaactg    300

cacccttctc ttcttttctc tcataataat ttaaatttgt tatagactct aaactttaaa    360

tgtttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttagga aagttctttt gttgcagtaa      540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

<210> SEQ ID NO 329
<211> LENGTH: 3236
<212> TYPE: DNA
<213> ORGANISM: Artificial Sequence
<220> FEATURE:
<223> OTHER INFORMATION: PHP44230 amiRNA precursor expression construct

<400> SEQUENCE: 329

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgcccag catctccaat gtgaaagaag ctaaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttcttta acatcaatta ttgtttttgt caacaagcta tcttttagtt    600
ttattttatt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atattttta    780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg    1920
atttatcttg tgattgttga ctctacagca gatcctaggt aaaccatggt tctagctagc   1980
tagggtttgg gtagtgagtg taataaagtt gcaaagtttt tggttaggtt acgttttgac   2040
```

```
cttattatta tagttcaaag ggaaacatta attaaagggg attatgaagt ggcgttggac   2100

taggtacttt tgaggatctt actgggtgaa ttgagctgct tagctatgga tcccacagtt   2160

ctacccatca ataagtgctt ttgtggtagt cttgtggctt ccatatctgg ggagcttcat   2220

ttgcctttat agtattaacc ttctaagtac catgtccaac gccacaccct tctcttcttt   2280

tctctcataa taatttaaat ttgttataga ctctaaactt taaatgtttt ttttgaagtt   2340

tttccgtttt tctcttttgc catgatcccg ttcttgctgt ggagtaacct tgtccgaggt   2400

atgtgcatga ttagatccat acttaatttg tgtgcatcac gaaggtgagg ttgaaatgaa   2460

ctttgctttt ttgacctttt aggaaagttc ttttgttgca gtaatcaatt ttaattagtt   2520

ttaattgaca ctattacttt tattgtcatc tttgttagtt ttattgttga attgagtgca   2580

tatttcgtag gaaattctct tacctaacat tttttataca gatctatgct cttggctctt   2640

gcccttactc ttggccttgt gttggttatt tgtctacata tttattgact ggtcgatgag   2700

acatgtcaca attcttgggc ttatttgttg gtctaataaa aggagtgctt attgaaagat   2760

caagacggag attcggtttt atataaataa actaaagatg acatattagt gtgttgatgt   2820

ctcttcagga taatttttgt ttgaaataat atggtaatgt cttgtctaaa tttgtgtaca   2880

taattcttac tgattttttg gattgttgga tttttataaa caaatctgtt aacagatctc   2940

ttctcccggg taactgtacc taaagaagga gtgcgtcgaa gcagatcgtt caaacatttg   3000

gcaataaagt ttcttaagat tgaatcctgt tgccggtctt gcgatgatta tcatataatt   3060

tctgttgaat tacgttaagc atgtaataat taacatgtaa tgcatgacgt tatttatgag   3120

atgggttttt atgattagag tcccgcaatt atacatttaa tacgcgatag aaaacaaaat   3180

atagcgcgca aactaggata aattatcgcg cgcggtgtca tctatgttac tagatc       3236
```

<210> SEQ ID NO 330
<211> LENGTH: 3237
<212> TYPE: DNA
<213> ORGANISM: Artificial Sequence
<220> FEATURE:
<223> OTHER INFORMATION: PHP44231 amiRNA precursor expression construct

<400> SEQUENCE: 330

```
ccgggtgatt gcggttacat catgtacgga aaaataattc taatccttga tttaaatttg     60

aacttgacta tttatttatt ctttatttca ttttgtaaat cattttatgt atctcctggc    120

aagcaatttt atccaccttg caccaacacc ttcgggttcc ataatcaaac caccttaact    180

tcacaccatg ctgtaactca caccgcccag catctccaat gtgaaagaag ctaaaattta    240

ataaacaatc atacgaagca gtgacaaaat accagatggt attaatgctt cgataaaatt    300

aattggaaag tataaaatgg tagaaaataa taaattataa ttaatttaag taagataaaa    360

aataattaaa aactaaaatg ttaaaatttt aaaaaaatta ttttaaataa tatttaaaaa    420

cattaaaaat cattttaaaa aatttattta tagaacaatt aaataaatat ttcagctaat    480

aaaaaacaaa agcttaccta gccttagaag acaacttgtc caacaattag atgataccca    540

ttgcccttac gttttcttta acatcaatta ttgtttttgt caacaagcta tcttttagtt    600

ttattttatt ggtaaaaaat atgtcgcctt caagttgcat catttaacac atctcgtcat    660

tagaaaaata aaactcttcc ctaaacgatt agtagaaaaa atcattcgat aataaataag    720

aaagaaaaat tagaaaaaaa taacttcatt ttaaaaaaat cattaaggct atattttta    780

aatgactaat tttatataga ctgtaactaa aagtatacaa tttattatgc tatgtatctt    840

aaagaattac ttataaaaat ctacggaaga atatcttaca aagtgaaaaa caaatgagaa    900
```

```
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat tttttttcac gaaattgctt cttgaaatta cgtgatggat tttgattctg   1920
atttatcttg tgattgttga ctctacagca gatcctaggt aaaccatgga ttctagctag   1980
ctagggtttg ggtagtgagt gtaataaagt tgcaaagttt ttggttaggt tacgttttga   2040
ccttattatt atagttcaaa gggaaacatt aattaaaggg gattatgaag ggtggtcag    2100
tatttgtaat ttgaggatct tactgggtga attgagctgc ttagctatgg atcccacagt   2160
tctacccatc aataagtgct tttgtggtag tcttgtggct tccatatctg gggagcttca   2220
tttgccttta tagtattaac cttctattac aataactgac caccccaccc ttctcttctt   2280
ttctctcata ataatttaaa tttgttatag actctaaact ttaaatgttt tttttgaagt   2340
ttttccgttt ttctcttttg ccatgatccc gttcttgctg tggagtaacc ttgtccgagg   2400
tatgtgcatg attagatcca tacttaattt gtgtgcatca cgaaggtgag gttgaaatga   2460
actttgcttt tttgaccttt taggaaagtt cttttgttgc agtaatcaat tttaattagt   2520
tttaattgac actattactt ttattgtcat ctttgttagt tttattgttg aattgagtgc   2580
atatttcgta ggaaattctc ttacctaaca ttttttatac agatctatgc tcttggctct   2640
tgcccttact cttggccttg tgttggttat ttgtctacat atttattgac tggtcgatga   2700
gacatgtcac aattcttggg cttatttgtt ggtctaataa aaggagtgct tattgaaaga   2760
tcaagacgga gattcggttt tatataaata aactaaagat gacatattag tgtgttgatg   2820
tctcttcagg ataattttg tttgaaataa tatggtaatg tcttgtctaa atttgtgtac    2880
ataattctta ctgatttttt ggattgttgg atttttataa acaaatctgt taacagatct   2940
cttctcccgg gtaactgtac ctaaagaagg agtgcgtcga agcagatcgt tcaaacattt   3000
ggcaataaag tttcttaaga ttgaatcctg ttgccggtct tgcgatgatt atcatataat   3060
ttctgttgaa ttacgttaag catgtaataa ttaacatgta atgcatgacg ttatttatga   3120
gatgggtttt tatgattaga gtcccgcaat tatacattta atacgcgata gaaaacaaaa   3180
tatagcgcgc aaactaggat aaattatcgc gcgcggtgtc atctatgtta ctagatc      3237
```

<210> SEQ ID NO 331
<211> LENGTH: 3226
<212> TYPE: DNA
<213> ORGANISM: Artificial Sequence
<220> FEATURE:
<223> OTHER INFORMATION: PHP44770 amiRNA precursor expression construct

<400> SEQUENCE: 331

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgcccag catctccaat gtgaaagaag ctaaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttcttta acatcaatta ttgtttttgt caacaagcta tcttttagtt    600
ttattttatt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atatttttta    780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg   1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaagg ggtggaaata attagtaggt   2100
```

tgaggatctt actgggtgaa ttgagctgct tagctatgga tcccacagtt ctacccatca 2160
ataagtgctt ttgtggtagt cttgtggctt ccatatctgg ggagcttcat ttgcctttat 2220
agtattaacc ttctcctact acatatttcc accccaccct tctcttcttt tctctcataa 2280
taatttaaat ttgttataga ctctaaactt taaatgtttt ttttgaagtt tttccgtttt 2340
tctcttttgc catgatcccg ttcttgctgt ggagtaacct tgtccgaggt atgtgcatga 2400
ttagatccat acttaatttg tgtgcatcac gaaggtgagg ttgaaatgaa ctttgctttt 2460
ttgacctttt aggaaagttc ttttgttgca gtaatcaatt ttaattagtt ttaattgaca 2520
ctattacttt tattgtcatc tttgttagtt ttattgttga attgagtgca tatttcgtag 2580
gaaattctct tacctaacat tttttataca gatctatgct cttggctctt gcccttactc 2640
ttggccttgt gttggttatt tgtctacata tttattgact ggtcgatgag acatgtcaca 2700
attcttgggc ttatttgttg gtctaataaa aggagtgctt attgaaagat caagacggag 2760
attcggtttt atataaataa actaaagatg acatattagt gtgttgatgt ctcttcagga 2820
taatttttgt ttgaaataat atggtaatgt cttgtctaaa tttgtgtaca taattcttac 2880
tgattttttg gattgttgga tttttataaa caaatctgtt aacagatctc ttctcccggg 2940
taactgtacc taaagaagga gtgcgtcgaa gcagatcgtt caaacatttg gcaataaagt 3000
ttcttaagat tgaatcctgt tgccggtctt gcgatgatta tcatataatt tctgttgaat 3060
tacgttaagc atgtaataat taacatgtaa tgcatgacgt tatttatgag atgggttttt 3120
atgattagag tcccgcaatt atacatttaa tacgcgatag aaaacaaaat atagcgcgca 3180
aactaggata aattatcgcg cgcggtgtca tctatgttac tagatc 3226

<210> SEQ ID NO 332
<211> LENGTH: 3226
<212> TYPE: DNA
<213> ORGANISM: Artificial Sequence
<220> FEATURE:
<223> OTHER INFORMATION: PHP44771 amiRNA precursor expression construct

<400> SEQUENCE: 332
ccgggtgatt gcggttacat catgtacgga aaaataattc taatccttga tttaaatttg 60
aacttgacta tttatttatt ctttatttca ttttgtaaat cattttatgt atctcctggc 120
aagcaatttt atccaccttg caccaacacc ttcgggttcc ataatcaaac caccttaact 180
tcacaccatg ctgtaactca caccgcccag catctccaat gtgaaagaag ctaaaattta 240
ataaacaatc atacgaagca gtgacaaaat accagatggt attaatgctt cgataaaatt 300
aattggaaag tataaaatgg tagaaaataa taaattataa ttaatttaag taagataaaa 360
aataattaaa aactaaaatg ttaaaatttt aaaaaaatta ttttaaataa tatttaaaaa 420
cattaaaaat cattttaaaa aatttattta tagaacaatt aaataaatat ttcagctaat 480
aaaaaacaaa agcttaccta gccttagaag acaacttgtc caacaattag atgataccca 540
ttgcccttac gttttcttta acatcaatta ttgtttttgt caacaagcta tcttttagtt 600
ttattttatt ggtaaaaaat atgtcgcctt caagttgcat catttaacac atctcgtcat 660
tagaaaaata aaactcttcc ctaaacgatt agtagaaaaa atcattcgat aataaataag 720
aaagaaaaat tagaaaaaaa taacttcatt ttaaaaaaat cattaaggct atattttta 780 aatgactaat tttatataga ctgtaactaa aagtatacaa tttattatgc tatgtatctt 840
aaagaattac ttataaaaat ctacggaaga atatcttaca aagtgaaaaa caaatgagaa 900

```
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg    1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaagt gggagaagat caaaggaatt   2100
tgaggatctt actgggtgaa ttgagctgct tagctatgga tcccacagtt ctacccatca   2160
ataagtgctt ttgtggtagt cttgtggctt ccatatctgg ggagcttcat ttgcctttat   2220
agtattaacc ttctattcct tctatcttct cccacaccct tctcttcttt tctctcataa   2280
taatttaaat ttgttataga ctctaaactt taaatgtttt ttttgaagtt tttccgtttt   2340
tctcttttgc catgatcccg ttcttgctgt ggagtaacct tgtccgaggt atgtgcatga   2400
ttagatccat acttaatttg tgtgcatcac gaaggtgagg ttgaaatgaa ctttgctttt   2460
ttgacctttt aggaaagttc ttttgttgca gtaatcaatt ttaattagtt ttaattgaca   2520
ctattacttt tattgtcatc tttgttagtt ttattgttga attgagtgca tatttcgtag   2580
gaaattctct tacctaacat tttttataca gatctatgct cttggctctt gcccttactc   2640
ttggccttgt gttggttatt tgtctacata tttattgact ggtcgatgag acatgtcaca   2700
attcttgggc ttatttgttg gtctaataaa aggagtgctt attgaaagat caagacggag   2760
attcggtttt atataaataa actaaagatg acatattagt gtgttgatgt ctcttcagga   2820
taatttttgt ttgaaataat atggtaatgt cttgtctaaa tttgtgtaca taattcttac   2880
tgattttttg gattgttgga tttttataaa caaatctgtt aacagatctc ttctcccggg   2940
taactgtacc taaagaagga gtgcgtcgaa gcagatcgtt caaacatttg gcaataaagt   3000
ttcttaagat tgaatcctgt tgccggtctt gcgatgatta tcatataatt tctgttgaat   3060
tacgttaagc atgtaataat taacatgtaa tgcatgacgt tatttatgag atgggttttt   3120
atgattagag tcccgcaatt atacatttaa tacgcgatag aaaacaaaat atagcgcgca   3180
aactaggata aattatcgcg cgcggtgtca tctatgttac tagatc                  3226
```

<210> SEQ ID NO 333
<211> LENGTH: 3226
<212> TYPE: DNA
<213> ORGANISM: Artificial Sequence
<220> FEATURE:
<223> OTHER INFORMATION: PHP44772 amiRNA precursor expression construct

<400> SEQUENCE: 333

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgcccag catctccaat gtgaaagaag ctaaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttcttta acatcaatta ttgtttttgt caacaagcta tcttttagtt    600
ttattttatt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atatttttta    780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg   1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaaga agaattatta taatactttt   2100
```

```
tgaggatctt actgggtgaa ttgagctgct tagctatgga tcccacagtt ctacccatca   2160

ataagtgctt ttgtggtagt cttgtggctt ccatatctgg ggagcttcat ttgcctttat   2220

agtattaacc ttctaaagta tattaataat tcttcaccct tctcttcttt tctctcataa   2280

taatttaaat ttgttataga ctctaaactt taaatgtttt ttttgaagtt tttccgtttt   2340

tctcttttgc catgatcccg ttcttgctgt ggagtaacct tgtccgaggt atgtgcatga   2400

ttagatccat acttaatttg tgtgcatcac gaaggtgagg ttgaaatgaa ctttgctttt   2460

ttgacctttt aggaaagttc ttttgttgca gtaatcaatt ttaattagtt ttaattgaca   2520

ctattacttt tattgtcatc tttgttagtt ttattgttga attgagtgca tatttcgtag   2580

gaaattctct tacctaacat tttttataca gatctatgct cttggctctt gcccttactc   2640

ttggccttgt gttggttatt tgtctacata tttattgact ggtcgatgag acatgtcaca   2700

attcttgggc ttatttgttg gtctaataaa aggagtgctt attgaaagat caagacggag   2760

attcggtttt atataaataa actaaagatg acatattagt gtgttgatgt ctcttcagga   2820

taatttttgt ttgaaataat atggtaatgt cttgtctaaa tttgtgtaca taattcttac   2880

tgatttttttg gattgttgga tttttataaa caaatctgtt aacagatctc ttctcccggg   2940

taactgtacc taaagaagga gtgcgtcgaa gcagatcgtt caaacatttg gcaataaagt   3000

ttcttaagat tgaatcctgt tgccggtctt gcgatgatta tcatataatt tctgttgaat   3060

tacgttaagc atgtaataat taacatgtaa tgcatgacgt tatttatgag atgggttttt   3120

atgattagag tcccgcaatt atacatttaa tacgcgatag aaaacaaaat atagcgcgca   3180

aactaggata aattatcgcg cgcggtgtca tctatgttac tagatc                  3226
```

```
<210> SEQ ID NO 334
<211> LENGTH: 3226
<212> TYPE: DNA
<213> ORGANISM: Artificial Sequence
<220> FEATURE:
<223> OTHER INFORMATION: PHP44773 amiRNA precursor expression construct

<400> SEQUENCE: 334

ccgggtgatt gcggttacat catgtacgga aaaataattc taatccttga tttaaatttg     60

aacttgacta tttatttatt ctttatttca ttttgtaaat cattttatgt atctcctggc    120

aagcaatttt atccaccttg caccaacacc ttcgggttcc ataatcaaac caccttaact    180

tcacaccatg ctgtaactca caccgcccag catctccaat gtgaaagaag ctaaaattta    240

ataaacaatc atacgaagca gtgacaaaat accagatggt attaatgctt cgataaaatt    300

aattggaaag tataaaatgg tagaaaataa taaattataa ttaatttaag taagataaaa    360

aataattaaa aactaaaatg ttaaaatttt aaaaaaatta ttttaaataa tatttaaaaa    420

cattaaaaat cattttaaaa aatttattta tagaacaatt aaataaatat ttcagctaat    480

aaaaaacaaa agcttaccta gccttagaag acaacttgtc caacaattag atgataccca    540

ttgcccttac gttttcttta acatcaatta ttgtttttgt caacaagcta tcttttagtt    600

ttattttatt ggtaaaaaat atgtcgcctt caagttgcat catttaacac atctcgtcat    660

tagaaaaata aaactcttcc ctaaacgatt agtagaaaaa atcattcgat aataaataag    720

aaagaaaaat tagaaaaaaa taacttcatt ttaaaaaaat cattaaggct atatttttta    780

aatgactaat tttatataga ctgtaactaa aagtatacaa tttattatgc tatgtatctt    840

aaagaattac ttataaaaat ctacggaaga atatcttaca aagtgaaaaa caaatgagaa    900

agaatttagt gggatgatta tgattttatt tgaaaattga aaaaataatt attaaagact    960
```

```
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat tttttttcac gaaattgctt cttgaaatta cgtgatggat tttgattctg   1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaagt tgtgtaaggg ttgatagtat   2100
tgaggatctt actgggtgaa ttgagctgct tagctatgga tcccacagtt ctacccatca   2160
ataagtgctt ttgtggtagt cttgtggctt ccatatctgg ggagcttcat ttgcctttat   2220
agtattaacc ttcttactat cttcccttac acaacaccct tctcttcttt tctctcataa   2280
taatttaaat ttgttataga ctctaaactt taaatgtttt ttttgaagtt tttccgtttt   2340
tctcttttgc catgatcccg ttcttgctgt ggagtaacct tgtccgaggt atgtgcatga   2400
ttagatccat acttaatttg tgtgcatcac gaaggtgagg ttgaaatgaa ctttgctttt   2460
ttgacctttt aggaaagttc ttttgttgca gtaatcaatt ttaattagtt ttaattgaca   2520
ctattacttt tattgtcatc tttgttagtt ttattgttga attgagtgca tatttcgtag   2580
gaaattctct tacctaacat tttttataca gatctatgct cttggctctt gcccttactc   2640
ttggccttgt gttggttatt tgtctacata tttattgact ggtcgatgag acatgtcaca   2700
attcttgggc ttatttgttg gtctaataaa aggagtgctt attgaaagat caagacggag   2760
attcggtttt atataaataa actaaagatg acatattagt gtgttgatgt ctcttcagga   2820
taatttttgt ttgaaataat atggtaatgt cttgtctaaa tttgtgtaca taattcttac   2880
tgattttttg gattgttgga tttttataaa caaatctgtt aacagatctc ttctcccggg   2940
taactgtacc taaagaagga gtgcgtcgaa gcagatcgtt caaacatttg gcaataaagt   3000
ttcttaagat tgaatcctgt tgccggtctt gcgatgatta tcatataatt tctgttgaat   3060
tacgttaagc atgtaataat taacatgtaa tgcatgacgt tatttatgag atgggttttt   3120
atgattagag tcccgcaatt atacatttaa tacgcgatag aaaacaaaat atagcgcgca   3180
aactaggata aattatcgcg cgcggtgtca tctatgttac tagatc                  3226
```

<210> SEQ ID NO 335

<211> LENGTH: 3226
<212> TYPE: DNA
<213> ORGANISM: Artificial Sequence
<220> FEATURE:
<223> OTHER INFORMATION: PHP44789 amiRNA precursor expression construct

<400> SEQUENCE: 335
ccgggtgatt gcggttacat catgtacgga aaaataattc taatccttga tttaaatttg 60
aacttgacta tttatttatt ctttatttca ttttgtaaat cattttatgt atctcctggc 120
aagcaatttt atccaccttg caccaacacc ttcgggttcc ataatcaaac caccttaact 180
tcacaccatg ctgtaactca caccgcccag catctccaat gtgaaagaag ctaaaattta 240
ataaacaatc atacgaagca gtgacaaaat accagatggt attaatgctt cgataaaatt 300
aattggaaag tataaaatgg tagaaaataa taaattataa ttaatttaag taagataaaa 360
aataattaaa aactaaaatg ttaaaatttt aaaaaaatta ttttaaataa tatttaaaaa 420
cattaaaaat cattttaaaa aatttattta tagaacaatt aaataaatat ttcagctaat 480
aaaaaacaaa agcttaccta gccttagaag acaacttgtc caacaattag atgataccca 540
ttgcccttac gttttcttta acatcaatta ttgtttttgt caacaagcta tcttttagtt 600
ttattttatt ggtaaaaaat atgtcgcctt caagttgcat catttaacac atctcgtcat 660
tagaaaaata aaactcttcc ctaaacgatt agtagaaaaa atcattcgat aataaataag 720
aaagaaaaat tagaaaaaaa taacttcatt ttaaaaaaat cattaaggct atatttttta 780
aatgactaat tttatataga ctgtaactaa aagtatacaa tttattatgc tatgtatctt 840
aaagaattac ttataaaaat ctacggaaga atatcttaca aagtgaaaaa caaatgagaa 900
agaatttagt gggatgatta tgattttatt tgaaaattga aaaaataatt attaaagact 960
ttagtggagt aagaaagctt tcctattagt cttttcttat ccataaaaaa aaaaaaaaaa 1020
atctagcgtg acagcttttc catagatttt aataatgtaa aatactggta gcagccgacc 1080
gttcaggtaa tggacactgt ggtcctaact tgcaacgggt gcgggcccaa tttaataacg 1140
ccgtggtaac ggataaagcc aagcgtgaag cggtgaaggt acatctctga ctccgtcaag 1200
attacgaaac cgtcaactac gaaggactcc ccgaaatatc atctgtgtca taaacaccaa 1260
gtcacaccat acatgggcac gcgtcacaat atgattggag aacggttcca ccgcatatgc 1320
tataaaatgc ccccacaccc ctcgacccta atcgcacttc aattgcaatc aaattagttc 1380
attctctttg cgcagttccc tacctctcct ttcaaggttc gtagatttct tccgtttttt 1440
tttcttcttc tttattgttt gttctacatc agcatgatgt tgatttgatt gtgttttcta 1500
tcgtttcatc gattataaat tttcataatc agaagattca gcttttatta atgcaagaac 1560
gtccttaatt gatgatttta taaccgtaaa ttaggtctaa ttagagtttt tttcataaag 1620
attttcagat ccgtttacaa caagccttaa ttgttgattc tgtagtcgta gattaaggtt 1680
tttttcatga actacttcag atccgttaaa caacagcctt atttgttgat acttcagtcg 1740
tttttcaaga aattgttcag atccgttgat aaaagcctta ttcgttgatt ctgtatggta 1800
tttcaagaga tattgctcag gtcctttagc aactacctta tttgttgatt ctgtggccat 1860
agattaggat tttttttcac gaaattgctt cttgaaatta cgtgatggat tttgattctg 1920
atttatcttg tgattgttga ctctacagca gatcctaggt tctagctagc tagggtttgg 1980
gtagtgagtg taataaagtt gcaaagtttt tggttaggtt acgttttgac cttattatta 2040
tagttcaaag ggaaacatta attaaagggg attatgaaga tcttgtgtta aatcttcgtt 2100
tgaggatctt actgggtgaa ttgagctgct tagctatgga tcccacagtt ctacccatca 2160

```
ataagtgctt ttgtggtagt cttgtggctt ccatatctgg ggagcttcat ttgcctttat   2220

agtattaacc ttctacgaag agataacaca agatcaccct tctcttcttt tctctcataa   2280

taatttaaat ttgttataga ctctaaactt taaatgtttt ttttgaagtt tttccgtttt   2340

tctcttttgc catgatcccg ttcttgctgt ggagtaacct tgtccgaggt atgtgcatga   2400

ttagatccat acttaatttg tgtgcatcac gaaggtgagg ttgaaatgaa ctttgctttt   2460

ttgacctttt aggaaagttc ttttgttgca gtaatcaatt ttaattagtt ttaattgaca   2520

ctattacttt tattgtcatc tttgttagtt ttattgttga attgagtgca tatttcgtag   2580

gaaattctct tacctaacat tttttataca gatctatgct cttggctctt gcccttactc   2640

ttggccttgt gttggttatt tgtctacata tttattgact ggtcgatgag acatgtcaca   2700

attcttgggc ttatttgttg gtctaataaa aggagtgctt attgaaagat caagacggag   2760

attcggtttt atataaataa actaaagatg acatattagt gtgttgatgt ctcttcagga   2820

taatttttgt ttgaaataat atggtaatgt cttgtctaaa tttgtgtaca taattcttac   2880

tgatttttttg gattgttgga tttttataaa caaatctgtt aacagatctc ttctcccggg   2940

taactgtacc taaagaagga gtgcgtcgaa gcagatcgtt caaacatttg gcaataaagt   3000

ttcttaagat tgaatcctgt tgccggtctt gcgatgatta tcatataatt tctgttgaat   3060

tacgttaagc atgtaataat taacatgtaa tgcatgacgt tatttatgag atgggttttt   3120

atgattagag tcccgcaatt atacatttaa tacgcgatag aaaacaaaat atagcgcgca   3180

aactaggata aattatcgcg cgcggtgtca tctatgttac tagatc                 3226
```

```
<210> SEQ ID NO 336
<211> LENGTH: 3226
<212> TYPE: DNA
<213> ORGANISM: Artificial Sequence
<220> FEATURE:
<223> OTHER INFORMATION: PHP44790 amiRNA precursor expression construct

<400> SEQUENCE: 336

ccgggtgatt gcggttacat catgtacgga aaaataattc taatccttga tttaaatttg     60

aacttgacta tttatttatt ctttatttca ttttgtaaat cattttatgt atctcctggc    120

aagcaatttt atccaccttg caccaacacc ttcgggttcc ataatcaaac caccttaact    180

tcacaccatg ctgtaactca caccgcccag catctccaat gtgaaagaag ctaaaattta    240

ataaacaatc atacgaagca gtgacaaaat accagatggt attaatgctt cgataaaatt    300

aattggaaag tataaaatgg tagaaaataa taaattataa ttaatttaag taagataaaa    360

aataattaaa aactaaaatg ttaaaatttt aaaaaaatta ttttaaataa tatttaaaaa    420

cattaaaaat catttttaaaa aatttattta tagaacaatt aaataaatat ttcagctaat    480

aaaaaacaaa agcttaccta gccttagaag acaacttgtc caacaattag atgataccca    540

ttgcccttac gttttcttta acatcaatta ttgtttttgt caacaagcta tcttttagtt    600

ttattttatt ggtaaaaaat atgtcgcctt caagttgcat catttaacac atctcgtcat    660

tagaaaaata aaactcttcc ctaaacgatt agtagaaaaa atcattcgat aataaataag    720

aaagaaaaat tagaaaaaaa taacttcatt ttaaaaaaat cattaaggct atattttta    780

aatgactaat tttatataga ctgtaactaa aagtatacaa tttattatgc tatgtatctt    840

aaagaattac ttataaaaat ctacggaaga atatcttaca aagtgaaaaa caaatgagaa    900

agaatttagt gggatgatta tgattttatt tgaaaattga aaaaataatt attaaagact    960
```

```
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg    1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaagc agtttttttt gcttttgttt   2100
tgaggatctt actgggtgaa ttgagctgct tagctatgga tcccacagtt ctacccatca   2160
ataagtgctt ttgtggtagt cttgtggctt ccatatctgg ggagcttcat ttgcctttat   2220
agtattaacc ttctaacaaa acaaaaaaaa actgcaccct tctcttcttt tctctcataa   2280
taatttaaat ttgttataga ctctaaactt taaatgtttt ttttgaagtt tttccgtttt   2340
tctcttttgc catgatcccg ttcttgctgt ggagtaacct tgtccgaggt atgtgcatga   2400
ttagatccat acttaatttg tgtgcatcac gaaggtgagg ttgaaatgaa ctttgctttt   2460
ttgacctttt aggaaagttc ttttgttgca gtaatcaatt ttaattagtt ttaattgaca   2520
ctattacttt tattgtcatc tttgttagtt ttattgttga attgagtgca tatttcgtag   2580
gaaattctct tacctaacat tttttataca gatctatgct cttggctctt gcccttactc   2640
ttggccttgt gttggttatt tgtctacata tttattgact ggtcgatgag acatgtcaca   2700
attcttgggc ttatttgttg gtctaataaa aggagtgctt attgaaagat caagacggag   2760
attcggtttt atataaataa actaaagatg acatattagt gtgttgatgt ctcttcagga   2820
taatttttgt ttgaaataat atggtaatgt cttgtctaaa tttgtgtaca taattcttac   2880
tgattttttg gattgttgga tttttataaa caaatctgtt aacagatctc ttctcccggg   2940
taactgtacc taaagaagga gtgcgtcgaa gcagatcgtt caaacatttg gcaataaagt   3000
ttcttaagat tgaatcctgt tgccggtctt gcgatgatta tcatataatt tctgttgaat   3060
tacgttaagc atgtaataat taacatgtaa tgcatgacgt tatttatgag atgggttttt   3120
atgattagag tcccgcaatt atacatttaa tacgcgatag aaaacaaaat atagcgcgca   3180
aactaggata aattatcgcg cgcggtgtca tctatgttac tagatc                  3226
```

<210> SEQ ID NO 337
<211> LENGTH: 21

<212> TYPE: DNA
<213> ORGANISM: Nezara viridula

<400> SEQUENCE: 337
tggcgttgga catggtactt a 21

<210> SEQ ID NO 338
<211> LENGTH: 21
<212> TYPE: DNA
<213> ORGANISM: Nezara viridula

<400> SEQUENCE: 338
gggtggtcag ttattgtaat a 21

<210> SEQ ID NO 339
<211> LENGTH: 21
<212> TYPE: DNA
<213> ORGANISM: Nezara viridula

<400> SEQUENCE: 339
gggtggaaat atgtagtagg a 21

<210> SEQ ID NO 340
<211> LENGTH: 21
<212> TYPE: DNA
<213> ORGANISM: Nezara viridula

<400> SEQUENCE: 340
tgggagaaga tagaaggaat a 21

<210> SEQ ID NO 341
<211> LENGTH: 21
<212> TYPE: DNA
<213> ORGANISM: Nezara viridula

<400> SEQUENCE: 341
aagaattatt aatatacttt a 21

<210> SEQ ID NO 342
<211> LENGTH: 21
<212> TYPE: DNA
<213> ORGANISM: Nezara viridula

<400> SEQUENCE: 342
ttgtgtaagg gaagatagta a 21

<210> SEQ ID NO 343
<211> LENGTH: 21
<212> TYPE: DNA
<213> ORGANISM: Nezara viridula

<400> SEQUENCE: 343
atcttgtgtt atctcttcgt a 21

<210> SEQ ID NO 344
<211> LENGTH: 21
<212> TYPE: DNA
<213> ORGANISM: Nezara viridula

<400> SEQUENCE: 344
cagttttttt ttgttttgtt a 21

<210> SEQ ID NO 345

-continued

```
<211> LENGTH: 21
<212> TYPE: DNA
<213> ORGANISM: Artificial Sequence
<220> FEATURE:
<223> OTHER INFORMATION: attB34 primer

<400> SEQUENCE: 345

caactttgta tagaaaagtt g                                              21


<210> SEQ ID NO 346
<211> LENGTH: 21
<212> TYPE: DNA
<213> ORGANISM: Artificial Sequence
<220> FEATURE:
<223> OTHER INFORMATION: attB3 primer

<400> SEQUENCE: 346

caactttgta taataaagtt g                                              21
```